(12) United States Patent
Close et al.

(10) Patent No.: US 11,046,962 B2
(45) Date of Patent: Jun. 29, 2021

(54) LUX EXPRESSION IN CELLS AND METHODS OF USE

(71) Applicant: 490 BioTech, Inc., Knoxville, TN (US)

(72) Inventors: Daniel Close, Knoxville, TN (US); Steven Ripp, Knoxville, TN (US); Gary Sayler, Blaine, TN (US); Michael Conway, Medford, MA (US)

(*) Notice: Subject to any disclaimer, the term of this patent is extended or adjusted under 35 U.S.C. 154(b) by 0 days.

(21) Appl. No.: 16/888,639

(22) Filed: May 29, 2020

(65) Prior Publication Data
US 2020/0377896 A1 Dec. 3, 2020

Related U.S. Application Data

(60) Provisional application No. 62/854,758, filed on May 30, 2019.

(51) Int. Cl.
| | | |
|---|---|---|
| C12N 15/64 | (2006.01) | |
| C12N 15/85 | (2006.01) | |
| C12N 5/074 | (2010.01) | |
| C12Q 1/66 | (2006.01) | |
| G01N 33/50 | (2006.01) | |

(52) U.S. Cl.
CPC .......... *C12N 15/64* (2013.01); *C12N 5/0607* (2013.01); *C12N 15/85* (2013.01); *C12Q 1/66* (2013.01); *G01N 33/5014* (2013.01); *C12Y 105/0103* (2013.01); *C12Y 114/14003* (2013.01)

(58) Field of Classification Search
CPC ..................................................... C12N 15/64
See application file for complete search history.

(56) References Cited

U.S. PATENT DOCUMENTS

| | | |
|---|---|---|
| 5,229,285 A | 7/1993 | Kajiyama et al. |
| 5,571,722 A | 11/1996 | Rosson |
| 5,834,237 A | 11/1998 | Jacobs et al. |
| 6,329,160 B1 | 12/2001 | Schneider et al. |
| 7,300,792 B2 | 11/2007 | Gupta et al. |
| 8,980,603 B2 | 3/2015 | Tannous et al. |
| 9,746,485 B2 | 8/2017 | Matsumoto |
| 2003/0096322 A1 | 5/2003 | Giuliano et al. |
| 2004/0142356 A1* | 7/2004 | Patterson .............. C12N 9/0069 435/6.13 |
| 2013/0017570 A1 | 1/2013 | Ohashi |
| 2013/0031644 A1 | 1/2013 | Ripp et al. |
| 2014/0140959 A1* | 5/2014 | Szalay ................ A61K 41/0038 424/93.2 |

FOREIGN PATENT DOCUMENTS

| | | |
|---|---|---|
| CN | 101003792 | 7/2007 |
| CN | 103160528 | 6/2013 |
| EP | 1885874 | 2/2008 |
| EP | 2551343 | 1/2013 |
| JP | 3155098 | 6/1994 |
| WO | 200118195 | 3/2001 |
| WO | 200208451 | 1/2002 |
| WO | 2004042010 | 5/2004 |
| WO | 2004059294 | 7/2004 |
| WO | 2008144052 | 11/2008 |
| WO | 2009050657 | 4/2009 |

OTHER PUBLICATIONS

Ripp, S., G. Sayler and Dan M. Close. "Mammalian-Based Bioreporter Targets: Protein Expression for Bioluminescent and Fluorescent Detection in the Mammalian Cellular Background." Chapter 22 in Biosensors for Health, Environment and Biosecurity. pp. 469-498 (2011) (Year: 2011).*

Xu et al. ("Autobioluminescent Cellular Models for Enhanced Drug Discovery" Chapter 1 in InTechOpen. Nov. 2016, pp. 1-23). (Year: 2016).*

Liger et al., Crystal Structure and Functional Characterization of Yeast YLR011wp, an Enzyme with NAD(P)H-FMN and Ferric Iron Reductase Activities, J. Biol. Chem, vol. 279, No. 33, pp. 34890-34897, 2004.

Zhou et al., Transcript leader regions of two Saccharomyces cerevisiae mRNAs contain internal ribosome entry sites that function in living cells, Proc. Natl. Acad. Sci. USA, vol. 98, No. 4, pp. 1531-1536, 2001.

Daunert et al., Genetically Engineered Whole-Cell Sensing Systems: Coupling Biological Recognition with Reporter Genes, Chem. Rev., 100: 2705-2738, 2000.

D'Souza, S., Microbial biosensors, Biosensors & Bioelectronics, 16: 337-353, 2001.

Kohler et al., Reporter gene bioassays in environmental analysis, Fresenius J. Anal Chem, 366: 767-779, 2000.

Routledge, E. et al, Estrogenic Activity of Surfactants and Some of Their Degradation Products Assessed Using a Recombinant Yeast Screen, Environmental Toxicology and Chemistry, 15: 241-248, 1996.

Almashanu et al., Fusion of LuxA and LuxB and its Expression in *E. coli, S. cerevisiae and D. Melanoigaster*, J. Biolumin. Chemilumin., 5: 89-97, 1990.

Boylan et al., Fused Bacterial Luciferase Subunits Catalyze Light Emission in Eukaryotes and Prokaryotes, 264: 1915-1918, 1989.

(Continued)

*Primary Examiner* — Scott Long
(74) *Attorney, Agent, or Firm* — Bradley Arant Boult Cummings; Alexandra C. Lynn; Timothy L. Capria

(57) ABSTRACT

Cells, including stem cells, comprising an autobioluminescent phenotype, wherein the cells emit a luminescent signal in the absence of an exogenous luminescent stimulator, are provided. The luminescent signal may be constitutive, inducible, repressible, or tissue-specific. The cells express a synthetically engineered bacterial luciferase (lux) cassette, i.e., the luxCDABEfrp gene cassette. The cells may comprise luxA, luxB, luxC, luxD, luxE, and flavin reductase. The cells may each express a combined expression level of luxC, luxD, luxE, and flavin reductase that is from ten to forty times greater than a combined expression level of luxA and luxB. Further, methods of making and using the cells comprising an autobioluminescent phenotype are disclosed herein.

32 Claims, 19 Drawing Sheets
Specification includes a Sequence Listing.

(56) References Cited

OTHER PUBLICATIONS

Kirchner et al., Active bacterial luciferase from a fused gene: expression of a Vibrio harveyi luxAB translational fusion in bacteria, yeast and plant cells, Gene, 81: 349-354, 1989.
Olsson et al., Engineering of monomeric bacterial luciferase by fusion of luxA and luxB genes in Vibrio harveyi, 81: 335-347, 1989.
Hellen, C. et al., Internal ribosome entry sites in eukaryotic mRNA molecules, Genes & Development, 15: 1593-1612, 2001.
Baker, V., Endocrine disrupters—testing strategies to assess human hazard, Toxicology in Vitro, 15: 413-419, 2001.
Hollis, R.P. et al., Toxicity of the bacterial luciferase substrate, n-decyl aldehyde, to *Saccharomyces cerevisiae* and Caenorhabditis elegans, FEBS Lett., vol. 506, pp. 140-142, 2001.
Bessoule, J.J. et al., Localization of the synthesis of very-long-chain fatty acid in mitochondria from *Saccharomyces cerevisiae*, Eur J Biochem. 177, 207-211, 1988.
Meighen, E.A. et al., Physiological, Biochemical and Genetic Control of Bacterial Bioluminescence, Adv. Microb. Physiol., vol. 34, pp. 1-67, 1993.
Johnson, D.R. et al., Genetic Analysis of the Role of *Saccharomyces cerevisiae* Acyl-CoA Synthetase Genes in Regulating Protein N-Myristoylation, J. Biol. Chem., vol. 269, pp. 18037-18046, 1994.
Gan, W.N. et al., Internal Initiation of Translation Directed by the 5'-Untranslated Region of the mRNA for eIF4G, a Factor Involved in the Picornavirus-induced Switch from Cap-dependent to Internal Initiation, J. Biol. Chem., vol. 271, pp. 623-626, 1996.
Henstrand, J.M. et al., *Saccharomyces cerevisiae* chorismate synthase has a flavin reductase activity. Mol. Microbiol., vol. 22, pp. 859-866, 1996.
Gradi, A.H. et al., A Novel Functional Human Eukaryotic Translation Initiation Factor 4G, Mol. Cell. Biology, vol. 18, pp. 334-342, 1998.
Miller, C.A. et al., Assessment of aryl hydrocarbon receptor complex interactions using pBEVY plasmids: expression vectors with bi-directional promoters for use in *Saccharomyces cerevisiae*, Nuc. Acids Res., vol. 26, pp. 3577-3583, 1998.
Rajala, R.V.S. et al., N-myristoyltransferase, Mol. and Cell. Biochem., vol. 204, pp. 135-155, 2000.
Gunaratne R.S. et al., Characterization of N-myristoyltransferase from Plasmodium falciparum, Biochem. J., vol. 348, pp. 459-463, 2000.
Kozak, M., New Ways of Initiating Translation in Eukaryotes?, Mol. Cell. Biol., vol. 21, pp. 1899-1907, 2001.
Wang, H et al., Trafficking Mesenchymal Stem Cell Engraftment and Differentiation in Tumor-Bearing Mice by Bioluminescence Imaging, Stem Cells 27:1548-1558 (2009).
Yasunaga, M et al., Continuous long-term cytotoxicity monitoring in 3D spheroids of beetle luciferase-expressing hepatocytes by nondestructive bioluminescence measurement, BMC Biotechnology, 17:54 (2017).
Sambrook J, et al., Reporter Assays: CAT, Luciferase, and b-galactosidase. Molecular cloning: A laboratory manual Cold Spring Harbor, New York: Cold Spring Harbor Laboratory Press, pp. 17.30-17.32 (2001).
Costa S, et al., Expression of fused bacterial luciferase in mammalian cells. Bioluminescence and Chemiluminescence. Stanley PE, Kricka LJ, editors. pp. 31-34 (1991).
C.Gregor et al, Autonomous bioluminescence imaging of single mammalian cells with the bacterial bioluminescence system, PNAS, vol. 116, No. 52, Dec. 26, 2019.
S.Patterson, Optimization of Bacterial Luciferase for Expression in Mammalian Cells, PhD diss., University of Tennessee, Dec. 2003.
G.C. Flynn, Individual subunits of bacterial luciferase are molten globules and interact with molecular chaperones, Proc. Natl. Acad. Sci. USA, vol. 90, pp. 10826-10830, Nov. 1993.
A. Sharma et al, High-throughput screening of tyrosine kinase inhibitor cardiotoxicity with human induced pluripotent stem cells. Sci. Transl. Med. 9, eaaf2584 (PubMed ID: 28202772), Feb. 15, 2017.

A. Hotta et al. Isolation of human iPS cells using EOS lentiviral vectors to select for pluripotency. Nat Methods 6, 370-376 (PubMed ID: 19404254), Apr. 2009.
X. Lian et al. Robust cardiomyocyte differentiation from human pluripotent stem cells via temporal modulation of canonical Wnt signaling. PNAS (PubMed ID: 22645348), May 2012.
B. Class et al., High-Throughput Viability Assay Using an Autonomously Bioluminescent Cell Line with a Bacterial Lux Reporter, Journal of Laboratory Automation, pp. 1-11, 2014.
D. Close et al., Comparison of human optimized bacterial luciferase, firefly luciferase, and green fluorescent protein for continuous imaging of cell culture and animal models, Journal of Biomedical Optics 16(4), 047003, Apr. 2011.
G. Choy et al., Comparison of noninvasive fluorescent and bioluminescent small animal optical imaging, BioTechniques 35(5), 1022-1031, 2003.
E. Meighen, Molecular biology of bacterial bioluminescence, Microbiol. Rev. 55(1), 123-142, 1991.
H. Seliger et al., Spectral emission and quantum yield of firefly bioluminescence, Arch. Biochem. Biophys. 88(1), 136-141, 1960.
Y. Ando et al., Firefly bioluminescence quantum yield and colour change by pH-sensitive green emission, Nature Photon. 2(1), 44-47, 2007.
Promega, Technical Manual: pGL4 Luciferase, Promega Corporation 2009.
Y.Wang et al., Fluorescence proteins, live-cell imaging,and mechanobiology: seeing is believing, Annu. Rev. Biomed. Eng. 10(1), 1-38 (2008).
A. Crameri, et al., Improved green fluorescent protein by molecular evolution using DNA shuffling, Nat. Biotechnol. 14(3), 315-319 (1996).
T. Troy, et al. Quantitative comparison of the sensitivity of detection of fluorescent and bioluminescent reporters in animal models, Imaging 3(1), 9-23 (2004).
S. Hilderbrand et al., Near-infrared fluorescence: application to in vivo molecular imaging, Curr. Opin. Chem. Biol. 14(1), 71-79 (2009).
J. Burdette, In vivo imaging of molecular targets and their function in endocrinology, J. Mol. Endocrinol. 40(6), 253-261 (2008).
J. Qin, et al., Systematic Comparison of Constitutive Promoters and the Doxycycline-Inducible Promoter, PLoS One 5 (5), e10611 (2010).
G. Caceres et al., Imaging of luciferase and GFP transfected human tumours in nude mice, Luminescence 18(4), 218-223 (2003).
D. Welsh et al., Bioluminescence imaging in living organisms, Curr. Opin. Biotechnol. 16(1), 73-78 (2005).
Y. Inoue, et al., Comparison of subcutaneous and intraperitoneal injection of D-luciferin for in vivo bioluminescence imaging, Eur. J. Nucl. Med. Mol. Imaging 36(5), 771-779 (2009).
K. Lee, et al., Cell uptake and tissue distribution of radioiodine labelled D-luciferin: implications for luciferase based gene imaging, Nucl. Med. Commun. 24(9), 1003-1009 (2003).
S. Mohler, Tips on Buying and Working with Luciferin, Genetic Engineering and Biotechnology News 30(4), 20-21 (2010).
K. O'Neill et al., Bioluminescent imaging: a critical tool in pre-clinical oncology research, J. Pathol. 220(3), 317-327 (2010).
J. Kim, et al., Non-invasive detection of a small number of bioluminescent cancer cells in vivo, PLoS One 5(2), e9364 (2010).
S. Islam, et al., Integrated circuit biosensors using living whole-cell bioreporters, IEEE Transactions on Circuits and Systems 54(1), 89-98 (2007).
D. Close et al., Autonomous Bioluminescent Expression of the Bacterial Luciferase Gene Cassette (lux) in a Mammalian Cell Line, PLoS One, 5(8), Aug. 2010.
CH Contag et al., Advances in in vivo bioluminescence imaging of gene expression. Annu Rev Biomed Eng 4: 235-260 (2002).
M. Oshiro et al., Cooled CCD versus intensified cameras for low-light video—Applications and relative advantages. Methods in Cell Biology 56: 45-62 (1998).
RY Tsien, The green fluorescent protein. Annu Rev Biochem 67:509-544 (1998).

(56) References Cited

OTHER PUBLICATIONS

V. Kalchenko et al., Use of lipophilic near-infrared dye in whole-body optical imaging of hematopoietic cell homing. J Biomed Opt 11: Article #050507 (2006).
Bloch S, et al., Whole-body fluorescence lifetime imaging of a tumor-targeted near-infrared molecular probe in mice. J Biomed Opt 10: Article #054003 (2005).
Zhao H, et al., Emission spectra of bioluminescent reporters and interaction with mammalian tissue determine the sensitivity of detection in vivo. J Biomed Opt 10: Article #041210 (2005).
Baggett B, et al. Thermostability of firefly luciferases affects efficiency of detection by in vivo bioluminescence. Mol Imaging 3: 324-332 (2004).
Bhaumik S, et al. Optical imaging of Renilla luciferase reporter gene expression in living mice. Proc Natl Acad Sci U S A 99: 377-382 (2002).
Escher A, et al., Bacterial luciferase alpha-beta fusion protein is fully active as a monomer and highly sensitive in vivo to elevated temperature. Proc Natl Acad Sci U S A 86: 6528-6532 (1989).
Pazzagli M, et al., Use of bacterial and firefly luciferases as reporter genes in DEAE-dextran-mediated transfection of mammalian cells. Anal Biochem 204: 315-323 (1992).
Koncz C, et al., Expression and assembly of functional bacterial luciferase in plants. Proc Natl Acad Sci U S A 84: 131-135 (1987).
Contag CH, et al., Photonic detection of bacterial pathogens in a living host. Molec Micro 18: 593-603 (1995).
Patterson SS, et al., Codon optimization of bacterial luciferase (lux) for expression in mammalian cells. J Ind Microbiol Biotechnol 32: 115-123 (2005).
Westerlund-Karlsson A, et al., Generation of thermostable monomeric luciferases from Photorhabdus luminescens Biochem Biophys Res Commun 296: 1072-1076 (2002).
Gupta RK, et al. Expression of the Photorhabdus luminescens lux genes (luxA, B, C, D, and E) in *Saccharomyces cerevisiae*. FEMS Yeast Res 4: 305-313 (2003).
Barrett JW, et al. Optimization of codon usage of poxvirus genes allows for improved transient expression in mammalian cells. Virus Genes 33: 15-26 (2006).
Mechold U, et al., Codon optimization of the BirA enzyme gene leads to higher expression and an improved efficiency of biotinylation of target proteins in mammalian cells. J Biotechnol 116: 245-249 (2005).
Kim CH, et al., Codon optimization for high-level expression of human erythropoietin (EPO) in mammalian cells. Gene 199: 293-301 (1997).
Slimko EM, et al. Codon optimization of Caenorhabditis elegans GluCl ion channel genes for mammalian cells dramatically improves expression levels. J Neurosci Methods 124: 75-81 (2003).
Pestova TV, et al., Molecular mechanisms of translation initiation in eukaryotes. Proc Natl Acad Sci U S A 98: 7029-7036 (2001).
Dunn DK, et al., Conversion of aldehyde to acid in bacterial bioluminescent reaction. Biochemistry 12: 4911-4918 (1973).
Meighen EA, et al., Induction of fatty aldehyde dehydrogenase activity during development of bioluminescence in Beneckea harveyi. Biochem Biophys Res Commun 69: 423-429 (1976).
Szittner R, et al., Bright stable luminescent yeast using bacterial luciferase as a sensor. Biochem Biophys Res Commun 309:66-70 (2003).
Welham PA, et al., Mathematical model of the Lux luminescence system in the terrestrial bacterium Photorhabdus luminescens. Mol Biosyst 5: 68-76 (2009).
Vo-Dinh T, ed., Biomedical Photonics Handbook. Boca Raton, FL: CRC Press. 1872 p. (2003).
Colepicolo P, et al., Growth and luminescence of the bacterium Xehorhabdus luminescens from a human wound. Appl Environ Microbiol 55: 2601-2606 (1989).
D. Close et al., Expression of a Humanized Viral 2A—Mediated lux Operon Efficiently Generates Autonomous Bioluminescence in Human Cells, PLoS One, 9(5), May 2014.
Constance J, Molecular imaging markets. Kalorama Information Market Intelligence Report. New York, NY (2010).
De Wet J, et al., Cloning firefly luciferase. Methods in Enzymology 133: 3-14 (1986).
Lorenz W, et al., Isolation and expression of a cDNA encoding Renilla reniformis luciferase. Proceedings of the National Academy of Sciences of the United States of America 88: 4438-4442 (1991).
Verhaegen M, et al., Recombinant Gaussia luciferase. Overexpression, purification, and analytical application of a bioluminescent reporter for DNA hybridization. Anal Chem 74: 4378-4385 (2002).
Meighen EA, Biosynthesis of aliphatic aldehydes for the bacterial bioluminescent reaction stimulation by ATP and NADPH. Biochemical and Biophysical Research Communications 87: 1080-1086 (1979).
Vervoort J, et al., Bacterial luciferase: A C-13, N-15, and P-31 nuclear magnetic resonance investigation. Biochemistry 25: 8067-8075 (1986).
Meighen E, Enzymes and genes from the lux operons of bioluminescent bacteria. Annual Review of Microbiology 42: 151-176 (1988).
Sambrook J, et al., Molecular cloning: A laboratory manual. Cold Spring Harbor, New York: Cold Spring Harbor Laboratory Press (2001).
Szymczak AL, et al. Development of 2A peptide-based strategies in the design of multicistronic vectors. Expert Opinion on Biological Therapy 5:627-638 (2005).
Soto AM, et al.,The E-SCREEN assay as a tool to identify estrogens—an update on estrogenic environmental pollutants. Environmental Health Perspectives 103: 113-122 (1995).
Soto AM, et al. Strengths and weaknesses of in vitro assays for estrogenic and androgenic activity. Best Practice & Research Clinical Endocrinology & Metabolism 20: 15-33 (2006).
Legler J, et al., Development of a stably transfected estrogen receptor-mediated luciferase reporter gene assay in the human T47D breast cancer cell line. Toxicol Sci 48:55-66 (1999).
Wilson VS, et al., Development and characterization of a cell line that stably expresses an estrogen-responsive luciferase reporter for the detection of estrogen receptor agonist and antagonists. Toxicological Sciences 81: 69-77 (2004).
Tinikul R, et al., The fusion Vibrio campbellii luciferase as a eukaryotic gene reporter. Journal of Biotechnology 162: 346-353 (2012).
Szymczak AL, et al., Correction of multi-gene deficiency in vivo using a single 'self-cleaving' 2A peptide-based retroviral vector. Nature Biotechnology 22: 589-594 (2004).
Ibrahimi A, et al., Highly efficient multicistronic lentiviral vectors with peptide 2A sequences. Human Gene Therapy 20: 845-860 (2009).
Ryan MD, et al., Foot-and-mouth disease virus 2A oligopeptide mediated cleavage of an artificial polyprotein. EMBO Journal 13: 928-933 (1994).
Woltjen K, et al., piggyBac transposition reprograms fibroblasts to induced pluripotent stem cells. Nature 458: 766-U106 (2009).
Xu T, et al., Autonomously bioluminescent mammalian cells for continuous and real-time monitoring of cytotoxicity. Journal of Visualized Experiments 18: e50927 (2013).
Clontech, Tet-On® Advanced Inducible Gene Expression Systems User Manual. Mountain View, CA:Clontech Laboratories Inc. (Aug. 2009).
Gossen M, et al., Anhydrotetracycline, a novel effector for tetracycline controlled gene expression systems in eukaryotic cells. Nucleic Acids Research 21: 4411 (1993).
Yarranton G, Inducible vectors for expression in mammalian cells. Current Opinion in Biotechnology 3: 506-511 (1992).
Livak KJ, et al., Analysis of relative gene expression data using real-time quantitative PCR and the 2-DDCT method. Methods 25: 402-408 (2001).
Schmittgen TD, et al., Analyzing real-time PCR data by the comparative CT method. Nature Protocols 3: 1101-1108 (2008).
Hollis et al., "Toxicity of the bacterial luciferase substrate, n-decyl aldehyde, to *Saccharomyces cerevisiae* and Caenorhabditis elegans," 2001, FEBS Letters 506, p. 140-142.

(56) References Cited

OTHER PUBLICATIONS

Close et al., "Determining Toxicant Bioavailability Using a Constitutively Bioluminescent Human Cell Line," 2001, Proceedings of the 2011 Biomedical Sciences and Engineering Conference: Image Informatics and Analytics in Biomedicine.

Tehrani et al., Coexpression of luxA and luxB genes of Vibrio fischeri in NIH3T3 mammalian cells and evaluation of its bioluminescence activities, 2014, Luminescence: The Journal of Biological and Chemical Luminescence, vol. 29, p. 13-19.

Kotlobay et al., "Genetically encodable bioluminescent system from fungi," 2018, PNAS, vol. 115, No. 50, p. 12728-12732.

Mitiouchkina et al., "Plants with self-sustained luminescence," 2019, bioRxiv, available at: https://doi.org/10.1101/809376.

\* cited by examiner

Wild Type

IPSC: CBA-LUXAB and CBA-LUXCDEF

IPSC: tetO-LUXCDAEF and CBA-tTA iPSC::pNANOG-*neomycin*-pCBA-*LUXAB* and pNANOG-*zeocin*-pCBA-*LUXCDEF*.
Normal 46, XX karyotype.

iPSC::pNANOG-neomycin-tetO-*LUXCDABEF* and pNANOG-*zeocin*-CBA-*tTA*.
Normal 46, XX karyotype.

|  |  | RLU | Fold change |
|---|---|---|---|
| HEK293 | Single vector | $7.90 \times 10^5$ | 113 |
|  | Individual vectors | $8.91 \times 10^7$ |  |
| HCT116 | Single vector | $9.52 \times 10^4$ | 78 |
|  | Individual vectors | $7.40 \times 10^6$ |  |
| HeLa | Single vector | $4.74 \times 10^4$ | 264 |
|  | Individual vectors | $1.25 \times 10^7$ |  |
| HepG2 | Single vector | $2.81 \times 10^3$ | 1839 |
|  | Individual vectors | $5.17 \times 10^6$ |  |
| MCF7 | Single vector | $2.00 \times 10^3$ | 1203 |
|  | Individual vectors | $2.40 \times 10^6$ |  |

FIG. 13A    FIG. 13B    FIG. 13C
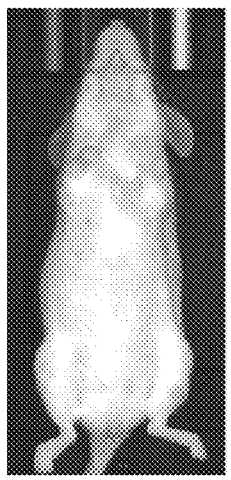 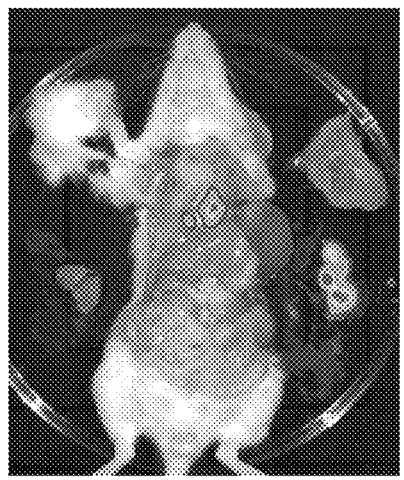 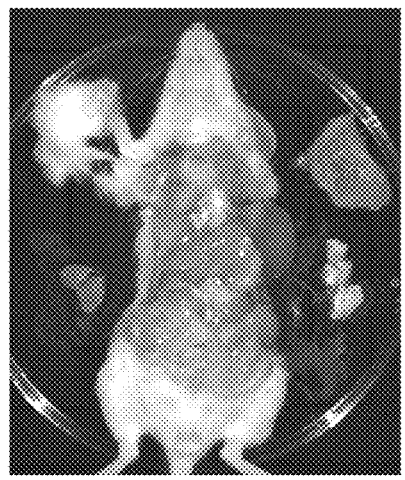
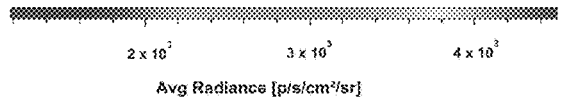

LUX EXPRESSION IN CELLS AND METHODS OF USE

CROSS-REFERENCE TO RELATED APPLICATION

This application cites the priority of currently U.S. 62/854,758 filed 30 May 2019. U.S. 62/854,758 is incorporated herein by reference in its entirety.

STATEMENT REGARDING FEDERALLY SPONSORED RESEARCH OR DEVELOPMENT

This invention was made with government support under grant numbers NIH NIGMS 2R42GM116622-02 and NIH NIEHS 1R43ES026269-01 awarded by the National Institutes of Health. The government has certain rights in the invention.

In this context "government" refers to the government of the United States of America.

This is a Nonprovisional patent application filed for an invention by Dr. Daniel Close, a citizen of the United States, residing in Knoxville, Tenn., Dr. Steven Ripp, a citizen of the United States, residing in Knoxville, Tenn., Dr. Michael Conway, a citizen of the United States, residing in Medford, Mass., and Dr. Gary Sayler, a citizen of the United States, residing in Blaine, Tennessee for the disclosure of "Lux Expression in Stem Cells and Methods of Use."

INCORPORATION-BY-REFERENCE OF SEQUENCE LISTING

The material in the accompanying sequence listing is hereby incorporated by reference in its entirety into this application. The accompanying file, named Sequences_218101_401002.txt, was created on and electronically submitted via EFS-Web on Aug. 10, 2020 and is 17.8 KB.

FIELD OF DISCLOSURE

The present disclosure pertains to cells comprising an autonomous luminescent phenotype. More specifically, the present disclosure is directed to expression of a synthetically engineered bacterial luciferase (lux) cassette, i.e., the luxCDABEfrp gene cassette in new ratios, in stem and specialized cells, and the methods of making and using said cells.

BACKGROUND OF THE DISCLOSURE

Regenerative medicine represents a shift in traditional medical treatment and therapeutic goals. Rather than merely treating a myriad of symptoms, regenerative medicine focuses on remediating the underlying cause of a disease state through the repair or regeneration of damaged cells. At the forefront of regenerative medicine is stem cell-based therapy. With their potential for self-renewal and capability to differentiate into other cell types, stem cells show considerable promise in revolutionizing regenerative medicine.

Presently, however, there are still a number of significant impediments facing the implementation of stem cell-based therapies in clinical practice. Specifically, stem cell migration and fate are often studied through methods that are either not clinically translatable, such as post-mortem analysis, or not universally accessible due to high costs, such as positron emission tomography and single photon emission computed tomography. Moreover, present in vivo imaging approaches are not conducive to frequent imaging sessions as these approaches generally require anesthetizing the subject and permitting subject recovery between imaging sessions. As a result, much of the information regarding stem cell viability, migration, and fate is lost between imaging sessions.

Therefore, there is a clear need for novel techniques for non-invasive guiding and verification of cell injection, the tracking of cell migration, and the monitoring of long-term integration and survival of stem cells, including under both in vitro and in vivo modalities. The development of such techniques is paramount to improved clinical implementation and utilization of stem cell-based therapies.

BRIEF SUMMARY

The problems described above, as well as others, are addressed by the following embodiments, although it is to be understood that not every embodiment of this disclosure will address each of the problems described above. Further advantages, features, and details of the embodiments can be gathered from the claims, the description of preferred embodiments below, as well as the drawings.

A stem cell comprising an autobioluminescent phenotype, also referred to as an autonomous luminescent phenotype, is disclosed. The autobioluminescent phenotype comprises emitting an autonomous bioluminescent signal, also referred to as an autobioluminescent signal, in the absence of an exogenous luminescent stimulator. The exogenous luminescent stimulator may be a fluorescent stimulation signal or a chemical luminescent activator. The chemical luminescent activator may, for example, comprise an aldehyde functional group.

The autobioluminescent signal emitted by the stem cell may either be constitutive, inducible, repressible, or tissue-specific. In embodiments wherein the autobioluminescent signal is constitutive, the stem cell continuously emits the autobioluminescent signal. In embodiments wherein the autobioluminescent signal is inducible, the stem cell emits the autobioluminescent signal when exposed to a stimulus (e.g., an analyte). In embodiments wherein the autobioluminescent signal is repressible, the stem cell ceases to emit the autobioluminescent signal when exposed to the stimulus. The autobioluminescent signal may be tissue-specific such that the autobioluminescent signal is only emitted when the stem cell differentiates into a tissue cell.

The stem cell may further comprise luxA, luxB, luxC, luxD, luxE, and flavin reductase proteins. The stem cell may further comprise nucleic acids encoding each of luxA, luxB, luxC, luxD, luxE, and flavin reductase.

In embodiments of the stem cell comprising nucleic acids encoding each of luxA, luxB, luxC, luxD, luxE, and flavin reductase, at least one of the luxA nucleic acid, luxB nucleic acid, luxC nucleic acid, the luxD nucleic acid, the luxE nucleic acid, and the flavin reductase nucleic acid may be operatively linked to at least one linker region. The at least one linker region may comprise a viral 2A peptide or an internal ribosomal entry site element.

In some embodiments of the stem cell, at least one of luxC, luxD, luxE, and flavin reductase is present at a level greater than a level of at least one of luxA and luxB. In some embodiments, luxC, luxD, luxE, and flavin reductase may be present at a combined level of from ten times to forty times greater than a combined level of luxA and luxB. In some embodiments, luxC, luxD, luxE, and flavin reductase may be present at a combined level of from twenty times to thirty times greater than a combined level of luxA and luxB.

In embodiments wherein the autobioluminescent signal is constitutive, the nucleic acids encoding each of luxA, luxB, luxC, luxD, and flavin reductase are operatively linked to at least one constitutive promoter. In some embodiments, each of the foregoing nucleic acids are operatively linked to a separate constitutive promoter. In other embodiments, the luxA nucleic acid and the luxB nucleic acid may be operatively linked to a first constitutive promoter, and the luxC nucleic acid, the luxD nucleic acid, the luxE nucleic acid, and the flavin reductase nucleic acid may be operatively linked to a second constitutive promoter. The first constitutive promoter and the second constitutive promoter may each comprise the chicken beta-actin promoter.

In embodiments wherein the autobioluminescent signal is inducible in response to the analyte, at least one of the nucleic acids encoding each of luxA, luxB, luxC, luxD, luxE, and flavin reductase may be operatively linked to at least one analyte-responsive response element. The analyte may be any analyte that may bind to, and therefore activate, the at least one analyte-responsive response element.

The stem cell may further comprise at least one analyte-responsive reverse transactivator. The at least one analyte-responsive reverse transactivator may be operatively linked to a constitutive promoter, such as the chicken beta-actin promoter. The at least one analyte-responsive reverse transactivator may activate the at least one analyte-responsive response element in the presence of the analyte.

In embodiments wherein the autobioluminescent signal is repressible in response to the analyte, the stem cell may comprise at least one analyte-responsive response element operatively linked to at least one of the nucleic acids encoding each of luxA, luxB, luxC, luxD, luxE, and flavin reductase. The stem cell may comprise at least one analyte-responsive transactivator. The at least one analyte-responsive transactivator may be operatively linked to a constitutive promoter, such as chicken beta-actin promoter. The analyte may be any analyte that may bind to the at least one analyte-responsive transactivator.

The at least one analyte-responsive transactivator may activate the at least one analyte-responsive response element. In the presence of the analyte, however, the at least one analyte-responsive transactivator no longer activates the at least one analyte-responsive response element.

In embodiments wherein the autobioluminescent signal is tissue-specific, at least one of the nucleic acids encoding luxA, luxB, luxC, luxD, luxE, and flavin reductase is operatively linked to a tissue-specific promoter. In some embodiments, the luxA nucleic acid and the luxB nucleic acid may be operatively linked to a tissue-specific promoter, such that luxA and luxB are only expressed if the stem cell differentiates into a type of tissue cell in which the tissue-specific promoter is active. The luxC nucleic acid, the luxD nucleic acid, the luxE nucleic acid, and the flavin reductase nucleic acid may be operatively linked to a first constitutive promoter, such as the chicken beta-actin promoter. In embodiments having a tissue-specific autobioluminescent signal, emission of the autobioluminescent signal coincides with the onset of differentiation into the type in which the tissue-specific promoter is expressed, i.e., the autobioluminescent signal is tissue-specific.

In another aspect, a stem cell-derived autonomously bioluminescent cell is disclosed. The stem cell-derived autonomously bioluminescent cell may be an autonomously bioluminescent eukaryotic cell differentiated from an autonomously bioluminescent stem cell. The autonomously bioluminescent stem cell may comprise any embodiment of a stem cell comprising an autonomously bioluminescent phenotype disclosed herein. The stem cell-derived autonomously bioluminescent cell may inherit the characteristics of any embodiment of a stem cell comprising an autonomous bioluminescent phenotype from which the stem cell-derived autonomously bioluminescent cell is derived.

The stem cell-derived autonomously bioluminescent cell and the autonomously luminescent stem cell may express an autobioluminescent signal in the absence of an exogenous luminescent stimulator, such as an aldehyde substrate. The stem cell-derived autonomously bioluminescent cell emits an autonomous bioluminescent signal via expression of luxA, luxB, luxC, luxD, luxE, and flavin reductase.

In another aspect, a method is disclosed for producing a stem cell comprising an autonomous luminescent phenotype, wherein the stem cell emits a constitutive autobioluminescent signal. The method comprises transfecting a stem cell with at least one vector comprising luxA nucleic acid, a luxB nucleic acid, a luxC nucleic acid, a luxD nucleic acid, a luxE nucleic acid, and a flavin reductase nucleic acid. One or more of the nucleic acids may be operatively linked to one or more constitutive promoters. One of more of the nucleic acids may be linked by a linker region to facilitate expression.

For example, the method may comprise transfecting the stem cell with multiple vectors. In some embodiments, each of the luxA nucleic acid, a luxB nucleic acid, a luxC nucleic acid, a luxD nucleic acid, a luxE nucleic acid, and a flavin reductase nucleic acid are present on different vectors (i.e., one per each vector for a total of six vectors). Each of the foregoing nucleic acids may be operatively linked to constitutive promoters. In such embodiments, the method may comprise transfecting the stem cell with six vectors.

In other embodiments, the lux operon is split across two vectors. In such embodiments, the method may comprise transfecting the stem cell with a first vector and a second vector. The first vector may comprise a luxA nucleic acid and a luxB nucleic acid. The luxA nucleic acid and the luxB nucleic acid may be linked by at least one linker region, such as an internal ribosomal entry site or a viral 2A peptide. The luxA nucleic acid and the luxB nucleic acid may be operatively linked to a first constitutive promoter.

The second vector may comprise a luxC nucleic acid, a luxD nucleic acid, a luxE nucleic acid, and a flavin reductase nucleic acid. One or more of the luxC nucleic acid, luxD nucleic acid, luxE nucleic acid, and flavin reductase nucleic acid may be linked by at least one linker region to facilitate expression, such as an internal ribosomal entry site or a viral 2A peptide. The luxC nucleic acid, luxD nucleic acid, luxE nucleic acid, and flavin reductase nucleic acid may be operatively linked to a second constitutive promoter.

The method may include transfecting the stem cell with an amount of the second vector that is from ten to forty times greater than an amount of the first vector or from twenty to thirty times greater than an amount of the first vector.

A kit is disclosed for producing a stem cell comprising an autonomous luminescent phenotype, wherein the stem cell emits a constitutive autobioluminescent signal. The kit comprises any vector disclosed above in the methods for producing a stem cell comprising an autonomous luminescent phenotype, wherein the stem cell emits a constitutive autobioluminescent signal. The kit may comprise any number of vectors (e.g., one, two, three, four, five, or six etc.) comprising any number of configurations of at least one of the nucleic acids encoding each of luxA, luxB, luxC, luxD, luxE, and flavin reductase. By way of example, a two vector system could comprise a first vector including nucleic acids encoding each of luxA and luxB and a second vector comprising each of luxC, luxD, luxE, and flavin reductase.

A method is disclosed for producing a stem cell comprising an autonomous luminescent phenotype, wherein the stem cell emits an inducible autobioluminescent signal when exposed to an analyte. The method comprises transfecting the stem cell with at least one vector. The at least one vector comprises at least one of the nucleic acids encoding each of luxA, luxB, luxC, luxD, luxE, and flavin reductase. One or more of the at least one of the nucleic acids are operatively linked to at least one analyte-responsive regulatory element.

The method may comprise transfecting the stem cell with any number of vectors. For example, in some embodiments, the method may comprise transfecting the stem cell with a single vector comprising all of the nucleic acids encoding each of luxA, luxB, luxC, luxD, luxE, and flavin reductase operatively linked to the at least one analyte-responsive response element.

In other embodiments, the method may comprise transfecting the stem cell with multiple vectors. For example, there may be six vectors, wherein each vector contains one of the nucleic acids encoding each of luxA, luxB, luxC, luxD, luxE, and flavin reductase (i.e., each of the foregoing is expressed from a unique vector). At least one of the nucleic acids may be linked to the at least one analyte-response response element. Any nucleic acid not linked to the at least one analyte-response response element may be linked to a constitutive promoter.

In alternative embodiments, the method may comprise transfecting the stem cell with a first vector and a second vector. The first vector may comprise at least one of the nucleic acids encoding each of luxA, luxB, luxC, luxD, luxE, and flavin reductase operatively linked to at least one analyte-responsive response element. The second vector may comprise at least one of the nucleic acids encoding each of luxA, luxB, luxC, luxD, luxE, and flavin reductase operatively linked to a constitutive promoter. The first vector may comprise the nucleic acids encoding each of luxA and luxB operatively linked to an analyte-responsive response element. The second vector may comprise the nucleic acids encoding each of luxC, luxD, luxE, and flavin reductase operatively linked to a constitutive promoter. In any of the embodiments, one of more of the nucleic acids may be linked by a linker region to facilitate expression. The at least one linker region may be an internal ribosomal entry site or a viral 2A peptide.

In any of the embodiments, the analyte may bind to, and thereby activate, the at least one analyte-responsive response element. The activated at least one analyte-responsive response element causes modulation (e.g., an upregulation) in transcription of the nucleic acids to which it is operatively linked. In embodiments where the modulation is upregulation, this leads to production of the corresponding proteins that generate the autobioluminescent signal.

The method may further comprise transforming the stem cell with a vector comprising an at least one analyte-responsive reverse transactivator. The at least one analyte-responsive reverse transactivator may be operatively linked to a constitutive promoter. The at least one analyte-responsive reverse transactivator may activate the at least one analyte-responsive response element in the presence of the analyte.

A kit for producing a stem cell having inducible autobioluminescence is disclosed. The kit comprises any vector disclosed above in the methods for producing a stem cell comprising an autonomous luminescent phenotype, wherein the stem cell emits an inducible autobioluminescent signal. The kit may comprise any number of vectors (e.g., one, two, three, etc.) comprising any number of configurations of at least one of the nucleic acids encoding each of luxA, luxB, luxC, luxD, luxE, and flavin reductase. At least one of the nucleic acids is operatively linked to at least one analyte-responsive response element.

The kit may further comprise a vector including an at least one analyte-responsive reverse transactivator. When exposed to the analyte, the at least one analyte-responsive reverse transactivator activates the at least one analyte-responsive response element. The at least one analyte-responsive reverse transactivator may be operatively linked to a constitutive promoter, such as the chicken beta-actin promoter.

The kit may comprise an amount of the analyte. The analyte may be any analyte that may bind to, and therefore activate, the at least one analyte-responsive response element, thereby causing the at least one analyte-responsive reverse transactivator to bind to the at least one analyte-responsive response element, resulting in an inducible autobioluminescent signal.

A method is disclosed for producing a stem cell comprising an autonomous luminescent phenotype, wherein the stem cell emits an autobioluminescent signal that is repressible through exposure to an analyte.

The method comprises transfecting the stem cell with at least one vector. The at least one vector comprises at least one of the nucleic acids encoding each of luxA, luxB, luxC, luxD, luxE, and flavin reductase, wherein at least one of the nucleic acids is operatively linked to at least one analyte-responsive regulatory element. When activated, the analyte-responsive response element initiates translation of the nucleic acids to which it is operatively linked. One of more of the nucleic acids may be linked by a linker region to facilitate expression. The at least one linker region may be an internal ribosomal entry site or a viral 2A peptide.

The method may comprise transfecting the stem cell with any number of vectors. For example, in some embodiments, the method may comprise transfecting the stem cell with a single vector comprising all of the nucleic acids encoding each of luxA, luxB, luxC, luxD, luxE, and flavin reductase operatively linked to the at least one analyte-responsive response element.

In some embodiments, the method may comprise transfecting the stem cell with multiple vectors. For example, there may be six vectors, wherein each vector contains one of the nucleic acids encoding each of luxA, luxB, luxC, luxD, luxE, and flavin reductase (i.e., each of the foregoing is expressed from a unique vector). At least one of the nucleic acids may be linked to the at least one analyte-response response element. Any nucleic acid not linked to the at least one analyte-response response element may be linked to a constitutive promoter.

In further embodiments, the method may comprise transfecting the stem cell with a first vector and a second vector. The first vector may comprise at least one analyte-responsive response element operatively linked to at least one of the nucleic acids encoding each of luxA, luxB, luxC, luxD, luxE, and flavin reductase. The second vector may comprise at least one of the nucleic acids encoding each of luxA, luxB, luxC, luxD, luxE, and flavin reductase operatively linked to a constitutive promoter. For example, in such embodiments, the first vector may comprise the nucleic acids encoding each of luxA and luxB operatively linked to an analyte-responsive response element. The second vector may comprise the nucleic acids encoding each of luxC, luxD, luxE, and flavin reductase operatively linked to a constitutive promoter.

In any of the above embodiments, the method may comprise transforming a stem cell with a vector comprising at least one analyte-responsive transactivator. The at least one analyte-responsive transactivator may be operatively linked to a constitutive promoter. The at least one analyte-responsive transactivator may activate the at least one analyte-responsive response element. In such embodiments, when the stem cell is exposed to the analyte, the analyte binds to the at least one analyte-responsive transactivator. As a result, the at least one analyte-responsive transactivator does not activate the at least one analyte-responsive response element. Thus, the at least one analyte-responsive response element fails to initiate transcription of the at least one nucleic acid to which it is operatively linked, thereby not expressing at least one of the nucleic acids encoding luxA, luxB, luxC, luxD, luxE, and flavin reductase. Consequently, the autobioluminescent signal may be repressed.

A kit for producing a stem cell having repressible autobioluminescence is disclosed. The kit comprises any vector disclosed above in the methods for producing a stem cell comprising an autonomous luminescent phenotype, wherein the stem cell emits a repressible autobioluminescent signal. The kit may comprise any number of vectors (e.g., one, two, three, etc.) comprising any number of configurations of at least one of the nucleic acids encoding each of luxA, luxB, luxC, luxD, luxE, and flavin reductase. At least one of the nucleic acids is operatively linked to at least one analyte-responsive response element.

In another aspect, a method is disclosed for producing a stem cell comprising a tissue-specific autonomous luminescent phenotype. The method comprises transfecting the stem cell with at least one vector. The at least one vector comprises at least one of the nucleic acids encoding each of luxA, luxB, luxC, luxD, luxE, and flavin reductase, wherein the at least one of the nucleic acids is operatively linked to a tissue-specific promoter. One or more of the nucleic acids may be linked by at least one linker region to any other nucleic acid on the same vector to facilitate expression. The at least one linker region may, for example, be an internal ribosomal entry site or a viral 2A peptide.

The method may comprise transfecting the stem cell with any number of vectors. For example, in some embodiments, the method may comprise transfecting the stem cell with a single vector comprising all of the nucleic acids encoding each of luxA, luxB, luxC, luxD, luxE, and flavin reductase operatively linked to the tissue-specific promoter. In such embodiments, after transfection with the single vector, the stem cell may produce an autobioluminescent signal when the stem cell is differentiated into a type of tissue cell (e.g., cardiac or neural) in which the tissue-specific promoter is active In further embodiments, the method may comprise transfecting the stem cell with multiple vectors. For example, there may be six vectors, wherein each vector contains one of the nucleic acids encoding each of luxA, luxB, luxC, luxD, luxE, and flavin reductase (i.e., each of the foregoing is expressed from a unique vector). At least one of the nucleic acids may be linked to the tissue-specific promoter. Any nucleic acid not linked to a tissue-specific promoter may be linked to a constitutive promoter.

In yet further embodiments, the method may comprise transfecting the stem cell with a first vector and a second vector. The first vector may comprise at least one of the nucleic acids encoding each of luxA, luxB, luxC, luxD, luxE, and flavin reductase, wherein the at least one of the nucleic acids is operatively linked to a tissue-specific promoter. The second vector may comprise at least one of the nucleic acids encoding each of luxA, luxB, luxC, luxD, luxE, and flavin reductase operatively linked to a constitutive promoter.

In some embodiments, the first vector may comprise the nucleic acids encoding each of luxA and luxB operatively linked to a tissue specific promoter, such as a TNNT2 promoter, that is specific for cardiomyocytes. In said embodiments, luxA and luxB are only expressed when the stem cell differentiates into a cardiomyocyte. The second vector may comprise the nucleic acids encoding each of luxC, luxD, luxE, and flavin reductase operatively linked to a constitutive promoter. Thus, there is a continuous expression of the nucleic acids encoding each of luxC, luxD, luxE, and flavin reductase. Therefore, for a TNNT2 promoter, upon differentiation of a stem cell into a cardiomyocyte, a tissue-specific autobioluminescent signal is emitted that may be imaged to bioindicate differentiation of the stem cell into a cardiomyocyte. This process can be used for detecting tissue-specific differentiation in other cell types and other tissue-specific promoters.

The method may comprise transforming the stem cell with an amount of the second vector that is from ten to forty times greater than an amount of the first vector. Preferably, the method may comprise transforming the stem cell with an amount of the second vector that is from twenty to thirty times greater than an amount of the first vector.

A kit for producing a stem cell comprising a tissue-specific autonomous luminescent phenotype is disclosed. A kit for producing a stem cell having repressible autobioluminescence is disclosed. The kit comprises any vector disclosed above in the methods for producing a stem cell comprising an autonomous luminescent phenotype, wherein the stem cell emits a tissue-specific autobioluminescent signal. The kit may comprise any number of vectors (e.g., one, two, three, etc.) comprising any number of configurations of at least one of the nucleic acids encoding each of luxA, luxB, luxC, luxD, luxE, and flavin reductase. At least one of the nucleic acids is operatively linked to at least tissue-specific promoter.

In another aspect, a method for producing a stem cell-derived autonomously luminescent cell from an autonomously luminescent stem cell is disclosed. The method comprises producing any embodiment of an autonomously luminescent stem cell disclosed herein. The method further comprises differentiating the autonomously luminescent stem cell into the stem cell-derived autonomously luminescent cell. The stem cell-derived autonomously luminescent cell may be any desired functional specialized cell. In such embodiments, the stem cell-derived autonomously luminescent cell emits a bioluminescent signal in the absence of an exogenous luminescent stimulator.

The stem cell-derived autonomously luminescent cell may produce a greater level of luxC, luxD, luxE, and flavin reductase than of luxA and luxB. The stem cell-derived autonomously luminescent cell may comprise a combined level of luxC, luxD, luxE, and flavin reductase that ranges from ten to forty times greater than a combined level of luxA and luxB. Preferably, the combined level of luxC, luxD, luxE, and flavin reductase range is from twenty to thirty times greater than the combined level of luxA and luxB.

In another aspect, methods for using a stem cell comprising an autonomous bioluminescent phenotype and methods for using a stem cell-derived autonomously luminescent cell are disclosed. The methods disclosed herein are highly scalable, thus accommodating low or high throughput applications. Further, the methods disclosed herein provide direct evidence of the stem cell's metabolic state in real-time. Moreover, the disclosed methods allow for continuous and automated analysis of the stem cell comprising an autonomous bioluminescent phenotype as well as the stem cell-derived autonomously bioluminescent cell.

In some aspects, methods for using at least one stem cell emitting a constitutive autobioluminescent signal are disclosed. For each such method, the method may comprise producing at least one stem cell emitting a constitutive luminescent signal. The at least one stem cell may be produced according to any of the methods disclosed herein for producing such a stem cell. Accordingly, the at least one stem cell will constitutively express luxA, luxB, luxC, luxD, luxE, and flavin reductase, such that the at least one stem cell autonomously emits a constitutive luminescent signal.

A method of real-time monitoring of cell population size of a population of at least one stem cell is disclosed. The method comprises measuring the constitutive luminescent signal emitted from the at least one stem cell. The method comprises assessing cell population size based on the measurement of the constitutive luminescent signal. In some embodiments, the method comprises measuring the cell population size over two or more points in time. The measurements may be taken at any number of time points.

In another aspect, a method of real-time monitoring of cell viability of at least one stem cell is provided. The method comprises measuring the constitutive luminescent signal emitted from the at least one stem cell. The method comprises assessing cell viability of the at least one stem cell based on the measurement of the constitutive luminescent signal. In some embodiments, the method comprises measuring the cell viability over two or more points in time. The measurements may be taken at any number of time points.

In another embodiment, a method for measuring an effect (e.g., cytotoxicity or therapeutic) of an agent in at least one stem cell is disclosed. The method comprises contacting the at least one stem cell with an agent. The agent may have a cytotoxic and/or therapeutic effect upon the at least one stem cell.

The method comprises measuring the constitutive luminescent signal emitted from the at least one stem cell after the at least one stem cell is exposed to the agent. In some embodiments, the method may comprise comparing the measurement of the constitutive luminescent signal emitted from the at least one stem cell to a constitutive luminescent signal emitted from a control population. In such embodiments, the method may comprise determining that a decrease in the measured constitutive luminescent signal emitted from the at least one stem cell relative to the constitutive luminescent signal emitted from the control population is indicative of a negative change in cell viability of the at least one stem cell resulting from contact with the agent. Further, in such embodiments, the method may comprise determining that the effect of the agent is cytotoxic. The method may comprise determining that the agent is fatal to the at least one stem cell when the at least one stem cell ceases production of the constitutive luminescent signal.

In other embodiments, the method may comprise determining that an increase in the measured constitutive luminescent signal emitted from the at least one stem cell relative to the constitutive luminescent signal emitted from the control population is indicative of a positive change in cell viability of the at least one stem cell resulting from contact with the agent. In such embodiments, the method may comprise determining that the effect of the agent is therapeutic.

The method may comprise subjecting the at least one stem cell to a range of concentrations of the agent. The method may comprise assessing the effect of the agent over two or more points in time. The method may comprise determining the agent's effect, such as when it stabilizes.

The method may comprise assessing an agent for drug discovery. That is, the cytotoxic and/or therapeutic results may contribute to ranking agents for consideration in drug discovery and to predict their fate and effects after administration to a living organism.

In another aspect, a method of reagent-free in vivo imaging of at least one stem cell is disclosed. The method comprises injecting the at least one stem cell constitutive luminescent signal into an organism. After injection of the at least one stem cell, the method comprises imaging the constitutive luminescent signal emitted from the at least one stem cell in the organism. In some embodiments, the method comprises measuring the constitutive luminescent signal and determining a total number of the at least one stem cell present in vivo.

The method may comprise, after the at least one stem cell is injected into the organism, tracking movement of the at least one stem cell within the organism. This may be performed by imaging the organism for location(s) of the autonomous luminescent signal, thereby determining migration of the at least one stem cell relative to site of injection. Alternatively, where, e.g., the autonomous luminescent signal is not sufficiently strong to penetrate from a deep tissue in vivo, tracking may be performed by sacrificing and dissecting the organism in order to be able to image the locations of the autonomous luminescent signal.

In other aspects, methods for using a stem cell emitting an inducible or repressible autobioluminescent signal when exposed to an analyte are also disclosed herein. The method comprises producing at least one stem cell comprising an autonomous luminescent phenotype, wherein the stem cell emits an inducible or repressible autobioluminescent signal when exposed to an analyte.

Methods for real-time monitoring of gene expression in at least one stem cell emitting an inducible or repressible autobioluminescent signal are disclosed. The method comprises contacting the at least one stem cell with an analyte. The analyte may be any suitable analyte that induces the stem cell to emit or repress the autobioluminescent signal. The method comprises measuring the autobioluminescent signal emitted from the at least one stem cell after the at least one stem cell is contacted with (e.g., exposed to) the analyte. The method may comprise comparing the measurement of the autobioluminescent signal emitted from the at least one stem cell to an autobioluminescent signal emitted from a control population.

In embodiments wherein the at least one stem cell emits an inducible autobioluminescent signal, an increase in the measured autobioluminescent signal emitted from the at least one stem cell relative to the autobioluminescent signal emitted from the control population is indicative of exposure to the analyte. Thus, in such embodiments, the method may include determining an activation of the nucleic acids encoding each of luxA, luxB, luxC, luxD, luxE, and flavin reductase in response to the analyte when the measured autobioluminescent signal is greater than the autobioluminescent signal emitted from the control population.

In embodiments wherein the at least one stem cell emits a repressible autobioluminescent signal, a reduction in the measured autobioluminescent signal emitted from the at least one stem cell relative to the autobioluminescent signal emitted from the control population is indicative of exposure to the analyte. Thus, in such embodiments, the method may include determining a repression of the nucleic acids encoding each of luxA, luxB, luxC, luxD, luxE, and flavin reductase in response to the analyte when the measured autobioluminescent signal is less than the autobioluminescent signal emitted from the control population.

In some embodiments, the method further comprises subjecting the at least one stem cell to a range of concentrations of the analyte.

The method may comprise assessing the effects of the analyte on gene expression over two or more points in time. Because the stem cell autonomously luminesces, the effects of the analyte can be continuously monitored.

In another aspect, a method of using at least one stem cell emitting an inducible or repressible autobioluminescent signal to determine a presence of an analyte in a sample is disclosed. The method comprises contacting the at least one stem cell with the sample. The method comprises measuring the autobioluminescent signal emitted from the at least one stem cell after the at least one stem cell is contacted with the sample. The method may comprise comparing the measurement of the autobioluminescent signal emitted from the at least one stem cell to an autobioluminescent signal emitted from a control population.

In embodiments wherein the at least one stem cell emits an inducible autobioluminescent signal, an increase in the measured autobioluminescent signal emitted from the at least one stem cell relative to the autobioluminescent signal emitted from the control population is indicative of contact with the analyte. Thus, in such embodiments, the method may comprise determining the presence of the analyte in the sample when the measured autobioluminescent signal is greater than the autobioluminescent signal emitted from the control population.

In embodiments wherein the at least one stem cell emits a repressible autobioluminescent signal, a reduction in the measured autobioluminescent signal emitted from the at least one stem cell relative to the autobioluminescent signal emitted from the control population is indicative of as a result of exposure to the analyte. Thus, in such embodiments, the method may comprise determining the presence of the analyte in the sample when the measured autobioluminescent signal is less than the autobioluminescent signal emitted from the control population.

In another aspect, a method of real-time differentiation reporting using at least one stem cell comprising a tissue-specific autonomous luminescent phenotype is disclosed. The method comprises providing at least one stem cell comprising a tissue-specific autonomous luminescent phenotype. The at least one stem cell may comprise any embodiment disclosed herein wherein the autobioluminescent signal is tissue-specific.

The method comprises measuring the bioluminescent signal emitted from the at least one tissue cell. The method may comprise tracking the differentiation of the at least one stem cell to the at least one tissue cell over two or more points in time. An emission of the bioluminescent signal may report an onset of the differentiation of the at least one stem cell to the tissue cell. The method may comprise assessing the cell population size of the at least one tissue cell based on the measurement of the bioluminescent signal.

In another aspect, methods are disclosed herein for using stem cell-derived autonomously bioluminescent cells. Each of said methods comprise producing at least one stem cell-derived autonomously bioluminescent cell that emits a constitutive bioluminescent signal. The at least one stem cell-derived autonomously bioluminescent cell may be produced according to any of the methods disclosed herein for producing such a cell. Accordingly, the at least one stem cell-derived autonomously bioluminescent cell may constitutively express luxA, luxB, luxC, luxD, luxE, and flavin reductase, such that said cell autonomously emits a constitutive bioluminescent signal.

A method of real-time monitoring of cell population size of a population of at least one stem cell-derived autonomously bioluminescent cell is provided. The method comprises measuring the constitutive luminescent signal emitted from the at least one stem cell-derived autonomously luminescent cell. The method comprises assessing cell population size based on the measurement of the constitutive bioluminescent signal. The method may comprise measuring the cell population size over two or more points in time. The measurement may be taken at any number of time points.

In another embodiment, a method of real-time monitoring of cell viability of at least one stem cell-derived autonomously luminescent cell is provided. The method comprises measuring the constitutive luminescent signal emitted from the at least one stem cell-derived autonomously luminescent cell. The method comprises assessing cell viability of the at least one stem cell-derived autonomously luminescent cell based on the measurement of the constitutive luminescent signal.

The method may comprise measuring the cell viability over two or more points in time. The measurement may be taken at any number of time points.

In another aspect, a method for measuring an effect of an agent using at least one a stem cell-derived autonomously luminescent cell is disclosed. The method comprises contacting the at least one stem cell-derived autonomously luminescent cell with an agent. In such embodiments, the agent may have a therapeutic and/or cytotoxic effect on the at least one stem cell. The method further comprises measuring the constitutive luminescent signal emitted from the at least one stem cell-derived autonomously luminescent cell after the at least one stem cell-derived autonomously luminescent cell is contacted with the agent.

In some embodiments, the method may comprise comparing the measurement of the constitutive luminescent signal emitted from the at least one stem cell-derived autonomously luminescent cell to a constitutive luminescent signal emitted from a control population. In such embodiments, the method may comprise determining that a decrease in the measured constitutive luminescent signal emitted from the at least one stem cell-derived autonomously luminescent cell relative to the constitutive luminescent signal emitted from the control population is indicative of a negative change in cell viability of the at least one stem cell-derived autonomously luminescent cell resulting from contact with the agent. In such embodiments, the method may comprise determining that the effect of the agent is cytotoxic. The method may comprise determining that the agent is fatal to the at least one stem cell-derived autonomously luminescent cell when the at least one stem cell-derived autonomously luminescent cell ceases production of the constitutive luminescent signal.

In other embodiments, the method may comprise determining that an increase in the measured constitutive luminescent signal emitted from the at least one stem cell-derived autonomously luminescent cell relative to the constitutive luminescent signal emitted from the control population is indicative of a positive change in cell viability of the at least one stem cell-derived autonomously luminescent cell resulting from contact with the agent. In such embodiments, the method may comprise determining that the effect of the agent is therapeutic.

The method may comprise subjecting the at least one stem cell-derived autonomously luminescent cell to a range of concentrations of the agent. The method may comprise assessing the effect of the agent over two or more points in time. The method may comprise assessing an agent for drug discovery.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present concepts in a simplified form as a prelude to the more detailed description that is presented later.

BRIEF DESCRIPTION OF THE DRAWINGS

FIG. 2A. Human induced pluripotent stem cells (iPSCs) transiently expressing the split lux operon (nanog-neo-CBA-luxAB and nanog-zeo-CBA-luxCDEF) at a 1:1 molar ratio compared to identical cells expressing the same amount of luxAB and an increasing amount of luxCDEF. Heat map image shown above each luxCDEF:luxAB ratio is representative of three replicates. FIG. 2B. Human adipose derived mesenchymal stem cells (hADMSCs) transiently expressing the split lux operon (nanog-neo-CBA-luxAB and nanog-zeo-CBA-luxCDEF) at a 1:1 molar ratio compared to identical cells expressing the same amount of luxAB and an increasing amount of luxCDEF. Heat map image shown above each luxCDEF:luxAB ratio is representative of three replicates. FIG. 2C. LN229 cells transiently expressing the split lux operon (nanog-neo-CBA-luxAB and nanog-zeo-CBA-luxCDEF) at a 1:1 molar ratio compared to identical cells expressing the same amount of luxAB (luciferase genes) and an increasing amount of luxCDEF (luciferin genes). FIG. 2D. U87 cells transiently expressing the split lux operon (nanog-neo-CBA-luxAB and nanog-zeo-CBA-luxCDEF) at a 1:1 molar ratio compared to identical cells expressing the same amount of luxAB (luciferase genes) but an increasing amount of luxCDEF (luciferin genes).

FIG. 3A is a schematic of a viral 2A segmented, polycistronic lux operon driven by the chicken beta-actin (CBA) promoter and flanked by sequence elements to facilitate transposon mediated genomic integration (TE). The nanog promoter (nanog) drives the neomycin resistance gene (neo) to provide G418 selection following integration. FIG. 3B and FIG. 3C show the polycistronic lux operon split between two separate vectors. FIG. 3B is a schematic of a vector comprising luxA and luxB separated by a single 2A element and operatively linked to the chicken beta-actin (CBA) promoter. The vector retains the nanog promoter driven neomycin resistance gene. FIG. 3C is a schematic of a vector comprising luxC, luxD, luxE, and luxF separated by at least one 2A element linker region and operatively linked to the chicken beta-actin (CBA) promoter. The vector utilizes a nanog promoter driven zeocin resistance gene (zeo). Both vectors may further comprise flanking TEs for genomic integration.

FIG. 5A. Wild type iPSCs cultured for approximately 3 months were fixed and immunohistochemically labeled for Nanog, Oct4, and Ssea-4. The red circle at 100× denotes the region shown at 400×. FIG. 5B. Transposon mediated genomic integration of the split lux operon (pNANOG-neomycin-pCBA-LUXAB and pNANOG-zeocin-pCBA-LUXCDEF) into an iPSC line then cloned and cultured for 11 passages (approximately 3 months) expresses markers of pluripotency similar to wild type. FIG. 5C. Pluripotency marker expression was also observed in the iPSC line with the tetracycline-repressible lux operon (pNANOG-neomycin-tetO-LUXCDABEF and pNANOG-zeocin-CBA-tTA).

FIG. 6A. Transposon mediated genomic integration of the split lux operon (pNANOG-neomycin-pCBA-LUMB and pNANOG-zeocin-pCBA-LUXCDEF) into an iPSC line then cloned and cultured for 11 passages (approximately 3 months) retained a normal 46, XX karyotype. FIG. 6B. Karyotype stability was also observed for an iPSC line treated like that in FIG. 6A except for genomic integration of the tetracycline-repressible lux operon (pNANOG-neomycin-tetO-LUXCDABEF and pNANOG-zeocin-CBA-tTA).

FIG. 7A. The fold change in autobioluminescence produced from six vector expression approach relative to that produced from single vector approach is plotted for all tested cell lines. FIG. 7B. The fold change values are shown for each cell line.

9A. iPSCs with the genomically integrated CBA-luxAB and CBA-luxCDEF were seeded at the indicated cell density and imaged 24 hours after seeding. Image is a representative from 6 replicates. FIG. 9B. The fold change in radiant autobioluminescence relative to background plotted against the initial seeding cell density ($R^2$=0.93). FIG. 9C. The fold change in radiant autobioluminescence relative to background plotted against the fold change in MTT absorbance (570 nm) relative to background ($R^2$=0.98).

FIG. 12A. Increasing numbers of hADMSCs with genomically integrated CBA-luxAB and CBA-luxCDEF split operon were injected intraperitoneally into FVB inbred mice at the locations indicated by the red circles (cell number injected at site is indicated below the red circle) and imaged after 10 minutes. FIG. 12B. The fold change in the resulting average radiant luminescence (p/s/cm²/sr) was plotted against the total cell number injected. The average radiant luminescence (p/s/cm²/sr) emitted from the hADMSCs correlated strongly with the injected cell number ($R^2$=0.99).

FIGS. 13A-13C. Autobioluminescent human adipose derived mesenchymal stem cells (hADMSCs), according to an embodiment of the disclosure, track to the lungs following tail vein injection. FIG. 13A. 2 million hADMSCs with genomically integrated CBA-luxAB and CBA-luxCDEF split operon were injected into the tail vein of FVB inbred mice and imaged 1 hour post injection. FIG. 13B. Autobioluminescence is observable in the lungs following sacrifice and dissection. FIG. 13C. Image shows dissected FVB inbred mice of FIG. 13B without imaging overlay.

FIG. 15A. Human induced pluripotent stem cells (iPSCs) bearing genomically integrated polycistronic lux operon (luxCDABEF) under control of the tetracycline responsive promoter (tet-luxCDABEF) and a separately integrated chicken beta-actin (CBA)-driven reverse transactivator (rtTA) were exposed to increasing amounts of doxycycline for 4 and 24 hours. Autobioluminescence measurements generally show an increase in autobioluminescent output in response to exposure to increasing amounts of doxycycline. FIG. 15B. Autobioluminescence measurements from an iPSC tet-luxCDABEF line integrated and expressing a CBA-driven transactivator (tTA) show a reduction in autobioluminescent output in response to exposure of 4.1 µg/mL doxycycline as compared to <0.1 µg/mL doxycycline.

FIG. 19A. Representative images showing the autobioluminescent signal from iPSCs with genomically integrated luxAB and luxCDEF (left) and cardiomyocytes (CM) differentiated from the same parent iPSC-luxAB/CDEF line (right) also showing autobioluminescent signal. FIG. 19B. The normalized average autobioluminescent radiance per plated cell for the iPSC-luxAB/CDEF and CM-luxAB/CDEF cell lines. FIG. 19C. The autobioluminescent CM-luxAB/CDEF line was treated with a range of doxorubicin (uM) concentrations, and autobioluminescent output was measured after 24 hours of treatment.

FIG. 20A. Autobioluminescence emitted by human induced pluripotent stem cell (iPSC)-derived cardiomyocytes expressing the CBA-luxAB and CBA-luxCDEF split operon was measured every 10 minutes over the course of 30 hours. After 5 hours of monitoring in the absence of treatment, increasing doses of the cardiotoxicant doxorubicin (uM) were added (white arrow) and monitoring continued. Data represent the average of at least 3 replicates. FIG. 20B. Representative heat maps of the autobioluminescent signal at 2.5 hour intervals over the time series shown in FIG. 20A. FIG. 20C. The $IC_{50}$ values were calculated over the experimental time course and plotted against time.

DETAILED DESCRIPTION

Figure 1:
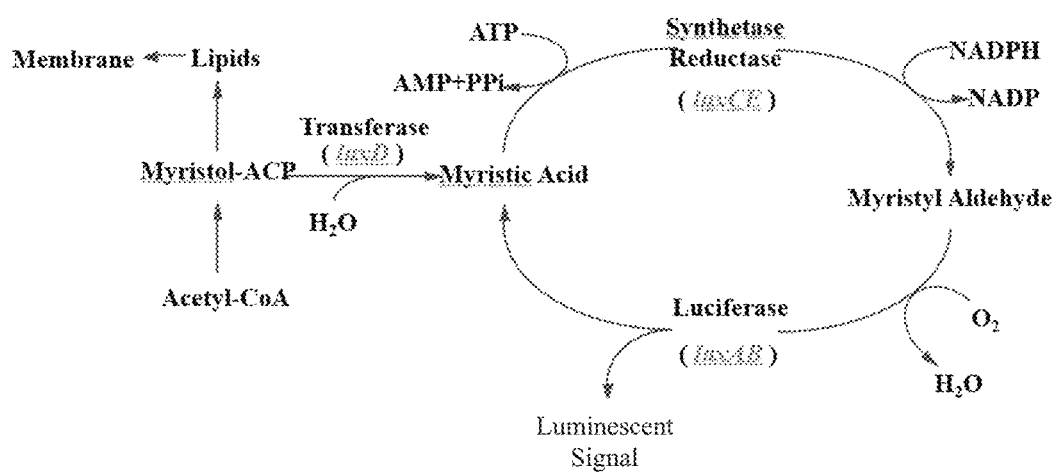
FIG. 1. Schematic showing production of luminescent signal via the lux cassette.

Reference now will be made in detail to the embodiments of the present disclosure. It is understood that the invention is not limited to the particular methodology, protocols, and reagents, etc., described herein, as these can be varied by one of ordinary skill in the art. It is also understood that the terminology used herein is used for the purpose of describing particular illustrative embodiments only and is not intended to limit the scope of the invention. It should be noted that the features illustrated in the drawings are not necessarily drawn to scale, and without departing from the scope of the disclosure, features of one embodiment may be employed with other embodiments as those of ordinary skill in the art would recognize, even if not explicitly stated herein. For instance, features illustrated or described as part of one embodiment, can be used with another embodiment to yield a further embodiment. Descriptions of well-known components and processing techniques may be omitted so as to not unnecessarily obscure the embodiments of the disclosure.

Thus, it is intended that the present disclosure covers such modifications and variations as come within the scope of the appended claims and their equivalents. Other objects, features, and aspects of the present disclosure are disclosed in or are apparent from the following detailed description. It is to be understood by one of ordinary skill in the art that the present disclosure is a description of exemplary embodiments only and is not intended as limiting the broader aspects of the present disclosure.

I. Definitions

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense, unless expressly so defined herein. Well-known functions or constructions may not be described in detail for brevity or clarity.

It is also noted that as used herein and in the appended claims, the singular forms "a," "an," and "the" include the plural reference unless the context clearly dictates otherwise. Thus, for example, a reference to "a cell" is a reference to one or more cells and equivalents thereof known to those of ordinary skill in the art.

The term "bioluminescent" and "luminescent" and similar phrases may be used interchangeably. Further, the term "autobioluminescent," "autonomously bioluminescent," and "autonomously luminescent," and similar phrases may be used interchangeably. A cell is autobioluminescent, or has autobioluminescence, when it self-synthesizes all of the substrates required for luminescent signal production, e.g., through expression of the luciferase (lux) cassette. That is, the mechanism for producing a luminescent signal (also referred to as bioluminescent signal), operates autonomously and in real-time to indicate cellular and molecular mechanisms coupled to bioluminescent signal output. Cells and methods of making and using cells having autobioluminescence are described in U.S. Pat. No. 7,300,792, which is incorporated by reference in its entirety.

The term "codon optimization" encompasses a strategy in which codons within a cloned gene—codons not generally used by the host cell translation system—are changed by mutagenesis, or any other suitable means, to the preferred codons of the host organism, without changing the amino acids of the synthesized protein.

The terms "encodes" and "encoding" refer to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system.

The term "expression" refers to the translation of a nucleic acid into a protein. Proteins may be expressed and remain intracellular, become a component of the cell surface membrane, or be secreted into the extracellular matrix or medium.

The term "lux cassette" refers to the bacterial luciferase (lux) gene cassette that comprises five genes: the luxC gene, the luxD gene, the luxA gene, the luxB gene, and the luxE gene. These five genes encode protein products that synergistically interact to generate bioluminescent light without the addition of an auxiliary substrate. Moreover, there is an additional gene, the flavin reductase gene (referred to as either "frp" or "F"), that functions as a flavin reductase to aid in cycling endogenous flavin mononucleotide into the $FMNH_2$ co-substrate required for the aforementioned bioluminescence reaction. These genes may be referred to in shorthand notation. For example, when referring to all five genes of the lux cassette, the shorthand notation may be luxCDABE. When referring to only a subset of said genes, the shorthand notation may be luxAB, luxCDE, or any other combination. Shorthand notation may also be employed to refer to the flavin reductase gene. For example, when referring to the flavin reductase gene with the lux cassette, the shorthand notation may be either luxCDABEfrp or luxCDABEF. The luxA gene, the luxB gene, the luxC gene, the luxD gene, the luxE gene, and frp may each have a wild type sequence, shown as SEQ ID NO: 1, SEQ ID NO: 2, SEQ ID NO: 3, SEQ ID NO: 4, SEQ ID NO: 5, and SEQ ID NO: 6, respectively, in the accompanying sequence listing. The luxA gene, the luxB gene, the luxC gene, the luxD gene, the luxE gene, and frp may each have a codon optimized sequence, shown as SEQ ID NO: 7, SEQ ID NO: 8, SEQ ID NO: 9, SEQ ID NO: 10, SEQ ID NO: 11, and SEQ ID NO: 12, respectively, in the accompanying sequence listing. Each of the foregoing genes may have sequences that include variations, derivations, and modifications of the wild type sequence and/or codon optimized sequence. Unless otherwise provided, references to the luxC gene, the luxD gene, the luxA gene, the luxB gene, the luxE gene, and frp encompass the wild type sequence and the codon optimized sequence (e.g., the wild type and codon optimized sequences provided in the accompanying sequence listing) and variations, derivations, and modifications thereof.

As generally used herein, "nucleic acid" refers to a polymer containing at least two nucleotides. The term nucleic acid includes deoxyribonucleic acid (DNA) and ribonucleic acid (RNA) and encompasses sequences that include any of the known base analogs of DNA and RNA. Nucleic acids can be linear, circular, or have higher orders of topology (e.g., supercoiled plasmid DNA). DNA can be in the form of antisense, plasmid DNA, parts of a plasmid DNA, vectors (P1, PAC, BAC, YAC, and artificial chromosomes), expression cassettes, chimeric sequences, chromosomal DNA, or derivatives of these groups. RNA can be in the form of oligonucleotide RNA, tRNA (transfer RNA), snRNA (small nuclear RNA), rRNA (ribosomal RNA), mRNA (messenger RNA), antisense RNA, (interfering) double-stranded and single-stranded RNA, ribozymes, chimeric sequences, or derivatives of these groups. Nucleic acid can be single (ssDNA,) double (dsDNA,) triple (tsDNA,) or quadruple (qsDNA) stranded DNA. RNA can be single stranded RNA (ssRNA) or double stranded RNA (dsRNA.) The term nucleic acid encompasses double- or triple-stranded nucleic acid, as well as single-stranded molecules.

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications, backbone modifications, unusual base pairing combinations, and the like.

A nucleic acid can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

As used herein, the expression "operatively linked" and similar phrases, when used in reference to nucleic acids, refer to the operational linkage of nucleic acid sequences placed in functional relationships with each other. For instance, if a promoter helps initiate transcription of the coding sequence, the coding sequence can be referred to as operatively linked to (or under control of) the promoter. There may be intervening sequence(s) between the promoter and coding region so long as this functional relationship is maintained.

The term "promoter" refers to a nucleotide sequence, usually upstream (5 prime) of the nucleotide sequence of interest, which directs and/or controls expression of the nucleotide sequence of interest by providing for recognition by RNA polymerase and other factors required for proper transcription. As used herein, the term "promoter" includes (but is not limited to) a promoter that is a short DNA sequence comprised of a TATA-box and other sequences that serve to specify the site of transcription initiation, to which regulatory, or response, elements are added for control of expression. The term "promoter" also refers to a nucleotide sequence that includes a promoter plus regulatory, or response, elements that are capable of controlling the expression of a coding sequence or functional RNA. This type of promoter sequence consists of proximal and more distal upstream elements, the latter elements often referred to as enhancers. The term "enhancer" refers to a DNA sequence that can stimulate promoter activity and can be an innate element of the promoter or a heterologous element inserted to enhance the level or tissue specificity of a promoter. Enhancers are capable of operating in both orientations (normal or flipped) and are capable of functioning even when moved either upstream or downstream of the promoter. Both enhancers and other upstream promoter elements bind sequence-specific DNA-binding proteins that mediate their effects.

A promoter can be derived in its entirety from a native gene, or be composed of different elements derived from different promoters found in nature, or even be comprised of synthetic DNA segments. A promoter also can contain DNA sequences that are involved in the binding of protein factors that control the effectiveness of transcription initiation in response to physiological or developmental conditions. Specific promoters used in accordance with the present disclosure can include, for example and without limitation, chicken beta-actin ("CBA") promoters, cytomegalovirus ("CMV") promoters, Rous sarcoma virus ("RSV") promoters, and neuron-specific enolase ("NSE") promoters.

A "constitutive" promoter drives expression continuously under most environmental conditions and states of development or cell differentiation. A constitutive promoter may be any suitable promoter that allows for continual transcription of the nucleic acids to which the promoter is operatively linked. A constitutive promoter may comprise a cell-type specific promoter or a promoter that is expressed independent of cell type. For example, constitutive promoters can include, the CBA promoter, the CMV promoter, the EF-1a promoter, or combinations thereof.

Alternatively, a promoter can be an "inducible" promoter (e.g. chemically or physically regulated promoter). A chemically regulated promoter can, for example, be regulated by the presence of alcohol, tetracycline, a steroid, or a metal. A physically regulated promoter can, for example, be regulated by environmental factors, such as temperature and light.

As used herein, "protein" means any peptide-linked chain of amino acids, regardless of length or post-translational modification, e.g., glycosylation or phosphorylation.

As used herein, the term "stem cell" refers to a relatively undifferentiated cell that actively divides and cycles, giving rise upon proper stimulation to a lineage of mature, differentiated, and functional cells. The stem cell may be any type of stem cell, for example, an adult stem cell (e.g., a tissue-specific stem cell), an embryonic (or pluripotent) stem cell, and an induced pluripotent stem cell (iPSC). The term "stem cell" also includes any progeny. It is understood that all progeny may not be identical to the parental cell since there may be mutations that occur during replication.

As used herein, the expression "selectable marker" refers to a marker that, when present in a cell, results in an attribute or phenotype that allows selection or segregation of those cells from other cells that do not express the selectable marker trait. A variety of genes are used as selectable markers, e.g., genes encoding drug resistance or auxotrophic rescue are widely known. For example, kanamycin (neomycin) resistance can be used as a trait to select bacteria that have taken up a plasmid carrying a gene encoding for bacterial kanamycin resistance (e.g., the enzyme neomycin phosphotransferase II). Non-transfected cells will eventually die off when the culture is treated with neomycin or similar antibiotics.

A cell, tissue, or organism into which has been introduced a foreign nucleic acid, such as a vector, is considered "transformed," "transfected," or "transgenic." A "transgenic" or "transformed" cell or organism (e.g., a stem cell) also includes progeny of the cell or organism. For example, a stem cell transgenic for luxA, luxB, luxC, luxD, or luxE is one in which a luxA, luxB, luxC, luxD, or luxE nucleic acid has been introduced, respectively.

Moreover, as used herein, the terms "transforming," "transfecting," and the like are used broadly to define a method of inserting a vector or other nucleic acids into a target cell. This can be accomplished, for example, by transfecting the vector into a target cell. Transfection methods are routine, and a number of transfection methods find use with the invention. These include but are not limited to calcium phosphate precipitation, electroporation, lipid-based methods, cationic polymer transfections, direct nucleic acid injection, biolistic particle injection, and viral transduction using engineered viral carriers (termed transduction, using e.g., engineered herpes simplex virus, adenovirus, adeno-associated virus, vaccinia virus, Sindbis virus), and sonoporation. Any of these methods find use with the disclosure.

Transfections can be divided into two categories: stable and transient transfections. Stable transfections result in the vector being permanently introduced into the cell and can be accomplished through the use of selectable marker, e.g., antibiotic resistance. Transient transfections result in the vector being introduced temporarily to the cell. Alternatively, if the vector is a viral vector, it can be transfected into a host cell to produce virus, and the virus can be harvested and used to transduce the vector into the target cell. Transfection and transduction protocols are known in the art.

As used herein, the term "vector" is used in reference to any recombinant polynucleotide molecule that can be propagated and used to transfer nucleic acid segment(s) to an organism. Vectors generally comprise parts which mediate vector propagation and manipulation (e.g., one or more origin of replication, genes imparting drug or antibiotic resistance, a multiple cloning site, operatively linked promoter/enhancer elements which enable the expression of a cloned gene, etc.). Vectors may comprise a marker gene that can confer a selectable phenotype, e.g., antibiotic resistance, on a cell. This marker product is used to determine if the gene has been delivered to the cell and once delivered is being expressed. Examples of suitable selectable markers include, but are not limited to, dihydrofolate reductase (DHFR), thymidine kinase, neomycin, neomycin analog G418, hygromycin, blasticidin, and puromycin. When such selectable markers are successfully transferred into a stem cell, the transformed stem cell can survive if placed under selective pressure.

A vector can be a linear molecule, or in circular form, depending on type of vector or type of application. Some circular nucleic acid vectors can be intentionally linearized prior to delivery into a cell. Vector is defined to include any virus, plasmid, cosmid, phage, or binary vector in double or single stranded linear or circular form that may or may not be self-transmissible or mobilizable, and that can transform eukaryotic host cells either by integration into the cellular genome or by existing extrachromosomally (e.g., autonomous replicating plasmid with an origin of replication). One type of vector is an episome, i.e., a nucleic acid capable of extra-chromosomal replication. Another type of vector is one that integrates within the host cell genome. Vectors may be capable of autonomous replication and/or expression of nucleic acids to which they are linked. Protocols for obtaining and using such vectors are known to those in the art.

As used herein, the term "at least one vector" may comprise one or more vectors corresponding to aspects of each of luxA, luxB, luxC, luxD, luxE, and flavin reductase (e.g., six vectors, wherein each of the foregoing genes are expressed from different vectors) or the lux cassette (e.g., five vectors). Any particular vector may comprise nucleic acids for one or more of luxA, luxB, luxC, luxD, luxE, and flavin reductase, in addition to any other nucleic acids. The vector(s) may not include any nucleic acids other than the nucleic acids for one or more of luxA, luxB, luxC, luxD, luxE, and flavin reductase.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

II. Stem Cell Comprising an Autobioluminescent Phenotype

A means of traversing the limitations imposed by the present limited techniques for examining, for example, stem cell viability, migration, and fate is the implementation of bioluminescent reporter genes into stem cells to enable non-invasive optical imaging of the bioluminescent stem cells. Most bioluminescent reporter systems, however, require administration of a substrate to activate light production, such as firefly, *Renilla*, or *Gaussia* luciferase. As a result, these systems are significantly limited in their potential for data acquisition due to variations in substrate quality, uptake rates, or exposure times. Moreover, in in vivo analysis of such systems, the required injections of activating substrate negatively impacts animal welfare, which makes exploration of potential therapeutics difficult if not impossible.

Accordingly, a stem cell comprising an autobioluminescent phenotype, also referred to as an autonomous bioluminescent phenotype, is disclosed. The autobioluminescent phenotype comprises emitting a bioluminescent signal, also referred to as an autobioluminescent signal, in the absence of an exogenous luminescent stimulator, i.e., the signal is produced "autonomously." The exogenous luminescent stimulator may be a fluorescent stimulation signal. The exogenous luminescent stimulator may be a chemical luminescent activator. In some embodiments, the chemical luminescent activator may comprise a luciferin or luciferin analog. For example, in some embodiments, the chemical may comprise, at least, an aldehyde functional group. In other embodiments, the chemical luminescent activator may comprise, for example, D-luciferin (2-(4-hydroxybenzothiazol-2-yl)-2-thiazoline acid), 3-hydroxy-hispidin, coelenterazine, or any other luciferin substrate.

The stem cell may be any type of stem cell, for example, an adult stem cell (e.g., a tissue-specific stem cell), an embryonic (or pluripotent) stem cell, and an induced pluripotent stem cell (iPSC).

The stem cell may comprise the bacterial luciferase (lux) cassette system, i.e., the luxCDABE gene cassette. The bacterial luciferase (lux) cassette system is capable of autonomously producing both its luciferase and associated luciferin generating protein products without exogenous investigator interaction. The stem cell may comprise luxA, luxB, luxC, luxD, luxE, and flavin reductase proteins. Moreover, mutant forms of these proteins or variant forms of these proteins might be used. Examples of variants include, but are not limited to, fragments, analogs, derivatives, and homologs of each of luxA, luxB, luxC, luxD, luxE, and flavin reductase. Recombinant forms of luxA, luxB, luxC, luxD, luxE, and flavin reductase may also be used.

The stem cell may comprise nucleic acids encoding each of luxA, luxB, luxC, luxD, luxE, and flavin reductase. The nucleic acids encoding each of luxA, luxB, luxC, luxD, luxE, and flavin reductase may be derived from any organism or strain. For example, luxA, luxB, luxC, luxD, and luxE may be derived from *P. luminescens, Vibrio harveyi, Xenorhabdus luminescens*, Photobac terium phosphoreum, Photobacterium leiognathi, and/or *Shewanella hanedai*. Further, flavin reductase may be derived from, for example, *Vibrio harveyi, Vibrio fischeri, Escherichia coli*, and/or *Helicobacter pylori*. Any one of the nucleic acids may be in the form of RNA or in the form of DNA, including cDNA, genomic DNA, and synthetic DNA. The DNA may be double-stranded or single stranded. Any one of the nucleic acids may encode mutant forms and/or variants of luxA, luxB, luxC, luxD, luxE, and/or flavin reductase. By way of example, the nucleic acids herein may comprise a nucleotide sequence that differs in one or more bases from native luxA, luxB, luxC, luxD, luxE, and/or flavin reductase. In such embodiments, said nucleotide sequences may include a deletion, addition, or substitution of one or more nucleotide bases as compared to native luxA, luxB, luxC, luxD, luxE, and/or flavin reductase.

The nucleic acids encoding each of luxA, luxB, luxC, luxD, luxE, and flavin reductase may be chromosomally integrated nucleic acids. Chromosomal integration may result in long-term stability of gene expression. To integrate nucleic acids encoding luxA, luxB, luxC, luxD, luxE, and flavin reductase into a stem cell chromosome, a number of methods may be employed. The nucleic acids encoding each of luxA, luxB, luxC, luxD, luxE, and flavin reductase may be expressed from any number of expression vectors (e.g., one, two, three, four, five or six vectors). For example, each of the foregoing may be expressed on separate expression vectors, or some nucleic acids may be provided on a single expression vector. Methods for inserting nucleic acids into stem cells are known in the art.

By way of example, a stem cell comprising nucleic acids encoding each of luxA, luxB, luxC, luxD, luxE, and flavin reductase autonomously produces a bioluminescent signal, via luxA, luxB, luxC, luxD, luxE, and flavin reductase working synergistically with endogenous myristic acid, endogenous flavin mononucleotide, and molecular oxygen to generate the bioluminescent signal (FIG. 1). Specifically, luxA and luxB form a heterodimeric luciferase component, whereas luxC, luxD, and luxE are, respectively, a reductase, a transferase, and a synthase that form a fatty acid reductase complex that regenerates an aldehyde substrate through the conversion of intracellular compounds. The flavin reductase helps cycle endogenous flavin mononucleotide into the required $FMNH_2$ co-substrate. Along with molecular oxygen, these components supply the enzyme with all the required products to produce a bioluminescent signal at about 490 nm. The luciferase enzyme catalyzes the oxidation of the aldehyde substrate in the presence of $FMNH_2$ and oxygen, thereby generating light at a peak wavelength of about 490 nm as a byproduct. The overall reaction can be summarized as: $FMNH_2+RCHO+O_2 \rightarrow FMN+H_2O+RCOOH+hv490$ nm.

Oxygen and $FMNH_2$ are naturally occurring within the cell, and the fatty acid reductase complex resulting from luxC, luxD, and luxE results in an in vivo generation of the aldehyde substrate. Therefore, the co-expression of luxA, luxB, luxC, luxD, luxE, and flavin reductase allows the stem cell to generate a bioluminescent signal in a fully autonomous fashion (that is, without the addition of an exogenous reagent). As a result, in some embodiments, the stem cell comprising an autonomous bioluminescent phenotype emits a bioluminescent signal at a peak wavelength of 490 nm.

Furthermore, it may be beneficial for bioluminescence production for there to be an increased abundance of luxA, luxB, luxC, luxD, luxE, and/or flavin reductase. Thus, in some embodiments, one or more of the nucleic acids may be codon optimized for expression in the stem cell. For example, one or more of the nucleic acids may be changed by mutagenesis to the preferred codons of the stem cell, without changing the amino acids of the protein synthesized from the one or more nucleic acids. Such codon optimization is advantageous in that it may lead to an increased quantity of luxA, luxB, luxC, luxD, luxE, and/or flavin reductase encoded by the one of more codon optimized nucleic acids.

Furthermore, in some embodiments, one or more of the nucleic acids encoding luxA, luxB, luxC, luxD, luxE and flavin reductase are operatively linked to one or more regulatory elements to promote and/or facilitate transcription. Operatively linked nucleic acid sequences can be contiguous and, where necessary to join two protein coding regions, in reading frame. Operatively linked nucleic acid sequences can also be non-contiguous. Examples of regulatory elements include promoters, enhancers, initiation sites, polyadenylation (polyA) tails, response elements, and termination signals.

In all embodiments disclosed herein, one or more of the luxA nucleic acid, the luxB nucleic acid, the luxC nucleic acid, the luxD nucleic acid, the luxE nucleic acid, and the flavin reductase nucleic acid may be operatively linked to at least one linker region. The presence of the at least one linker region is advantageous in that may facilitate expression of the at least one nucleic acid to which it is operatively linked. Specifically, the at least one linker region may allow multiple proteins to be translated from a single transcript, which is believed to increase functionality. The at least one linker region may link together individual genes for pseudo-polycistronic expression.

The at least one linker region may comprise an internal ribosomal entry site (IRES) element. An IRES element is advantageous in that it permits ribosomes to bind directly at an AUG start codon. Moreover, an IRES may result in an internal initiation of translation, such that a monocistronic mRNA essentially becomes multicistronic. Thus, operatively linking at least one IRES element to the nucleic acids encoding each of luxA, luxB, luxC, luxD, luxE, and flavin reductase may facilitate polycistronic synthesis of luxA, luxB, luxC, luxD, luxE, and flavin reductase.

In some embodiments, the at least one linker region comprises a viral 2A peptide. Examples of suitable viral 2A peptides include TSA (Seq. GluGlyArgGlySerLeuLeuThrCysGlyAspValGluGluAsnProGlyPro), P2A (AlaThrAsnPheSerLeuLeuLysGlnAlaGlyAspValGluGluAsnProGlyPro), E2A (GlnCysThrAsnTyrAlaLeuLeuLysLeuAlaGlyAspValGluSerAsnProGlyPro), and/or F2A (ValLysGlnThrLeuAsnPheAspLeuLeuLysLeuAlaGlyAspValGluSerAsnProGlyPro). Optionally, a GlySerGly sequence may be added to the N-terminal of the viral 2A peptides. Like the IRES element, the viral 2A peptide allows multiple proteins to be translated from a single transcript. However, as compared to an IRES element, the viral 2A peptide may result in increased transcriptional efficiency. It is believed that this is because the viral 2A peptide uses a mechanism of action that is more amenable to humanized polycistronic expression. Specifically, the steric hindrance imparted on the exit tunnel of the ribosome by the 2A peptide sequence results in a skip of the last peptide bond at the C-terminus of the 2A peptide sequence. The ribosome, however, is able to continue translation, thereby creating a second, independent protein product. Further, because the viral 2A peptide does not rely on secondary structure formation, it is shorter than the IRES element. Consequently, the viral 2A peptide is not as likely to suffer from a reduction in transcription and translation efficiency.

In any of the above embodiments wherein the stem cell comprises nucleic acids encoding each of luxA, luxB, luxC, luxD, luxE, and flavin reductase, the autobioluminescent signal emitted by the stem cell may either be constitutive, inducible, repressible, or tissue-specific, as further disclosed below.

1. Constitutive Autobioluminescent Signal

In embodiments wherein the autobioluminescent signal is constitutive, the stem cell continuously emits the autobioluminescent signal. In such embodiments, the nucleic acids encoding each of luxA, luxB, luxC, luxD, and flavin reductase are operatively linked to at least one constitutive promoter. Any constitutive promoter described herein (including the first constitutive promoter and the second constitutive promoter addressed below) may comprise any suitable promoter that allows for continual transcription at sufficient levels for production of the constitutive luminescent signal. For example, a constitutive promoter may comprise any promoter that functions in stem cells, including but not limited to, chicken beta-actin, cytomegalovirus, Rous sarcoma virus, human elongation factor 1α, simian virus 40 early, human β-actin, and neuron-specific enolase promoters.

In some embodiments, each of the luxA nucleic acid, the luxB nucleic acid, the luxC nucleic acid, the luxD nucleic acid, the luxE nucleic acid, and the flavin reductase nucleic acid may be operatively linked to a constitutive promoter. That is, in such embodiments, the foregoing nucleic acids are operatively linked to six constitutive promoters. The six constitutive promoters may be the same promoter or different promoters.

In other embodiments, the luxA nucleic acid and the luxB nucleic acid may be operatively linked to a first constitutive promoter. Additionally, the luxC nucleic acid, the luxD nucleic acid, the luxE nucleic acid, and the flavin reductase nucleic acid may be operatively linked to a second constitutive promoter. An advantage of having the nucleic acids under the operation of two separate constitutive promoters is that this configuration allows for easy implementation of varying ratios of luxA and luxB nucleic acids to luxC, luxD, luxE, and flavin reductase nucleic acids.

The first constitutive promoter and the second constitutive promoter may be the same promoter or different promoters. For example, the first constitutive promoter and the second constitutive promoter may each comprise the chicken beta-actin promoter. The chicken beta-actin promoter is advantageous in that it remains functional across a variety of stem cell types and imparts strong transcriptional activity as well as is capable of driving expression of long transcriptional units (see discussion below in Working Example 1).

By way of example, in embodiments wherein the nucleic acids encoding each of luxA, luxB, luxC, luxD, and flavin reductase are operatively linked to at least one constitutive promoter (including embodiments having the first constitutive promoter and the second constitutive promoter), there may be continuous expression of the nucleic acids to which each constitutive promoter is operatively linked. Thus, there is continuous production of each of luxA, luxB, luxC, luxD, luxE, and flavin reductase. This continuous production in turn results in emission of the constitutive bioluminescent signal. Moreover, this constitutive luminescent signal is fully self-generated and self-directed by the stem cell; thus, no exogenously added substrate (e.g., substrates having an aldehyde functional group) is necessary to generate the luminescent signal.

2. Inducible Autobioluminescent Signal

In embodiments wherein the autobioluminescent signal is inducible, the stem cell emits the autobioluminescent signal when exposed to an external stimulus. The external stimulus may, for example, comprise an analyte, an environmental condition (e.g., temperature and/or light), or transcriptional activation and/or deactivation of one of more nucleic acids.

In embodiments wherein the external stimulus comprises an analyte, at least one of the nucleic acids encoding each of luxA, luxB, luxC, luxD, luxE, and flavin reductase may be operatively linked to at least one analyte-responsive response element. The at least one analyte-responsive response element may, for example, comprise a modular enhancer unit or response element. The at least one analyte-responsive response element may be any response element capable of being regulated by the presence of an analyte. Examples of an at least one analyte-responsive response element include, but are not limited to, the estrogen response element, the androgen response element, the metal response element, the aromatic hydrocarbon response element, the electrophile response element, the retinoic acid and retinoid X response elements, the antioxidant response element, the glucocorticoid response element, the calcium-response element, the thyroid hormone response element, and the growth hormone response element.

The analyte may be any analyte that may bind to, and thereby activate, the at least one analyte-responsive response element. By way of example, if the at least one analyte-responsive response element comprises a hormone response element (e.g., estrogen- or androgen-responsive), the analyte may comprise a suitable environmental or natural hormone, such as estrogen or androgen, that may activate the hormone response element. Similarly, if the at least one analyte-responsive response element comprises the aromatic hydrocarbon response element, the analyte may comprise an endocrine-disruptor, such as dioxin or benzpyrene.

In some embodiments, the at least one analyte-responsive response element may be operatively linked to all of the nucleic acids encoding each of luxA, luxB, luxC, luxD, luxE, and flavin reductase. In such embodiments, exposure of the stem cell to the analyte causes the at least one analyte-responsive response element to upregulate transcription of each of the nucleic acids to which it is operatively linked. In other words, activation of the at least one analyte-responsive response element leads to production of each of the corresponding proteins necessary for generating the autobioluminescent signal.

In other embodiments, the at least one analyte-responsive response element is operatively linked to at least one of the nucleic acids encoding each of luxA, luxB, luxC, luxD, luxE, and flavin reductase. That is, a subset of at least one of the nucleic acids necessary for production of the autobioluminescent signal may be operatively linked to the at least one analyte-responsive response element. For example, in some embodiments, the at least one analyte-responsive response element may be operatively linked to only a single nucleic acid. In other embodiments, only the nucleic acids encoding each of luxA and luxB may be operatively linked to the at least one analyte-responsive response element. Thus, in said embodiments, when the stem cell is exposed to the analyte, the at least one analyte-responsive response element activates and initiates transcription of the nucleic acids encoding each of luxA and luxB.

The remaining at least one nucleic acid not linked to the at least one analyte-responsive response element may be operatively linked to a constitutive promoter such that the at least one nucleic acid is constitutively expressed. For example, continuing the above example wherein the nucleic acids encoding luxA and luxB are operatively linked to the at least one analyte-responsive response element, the remaining nucleic acids (i.e., the nucleic acids encoding each of luxC, luxD, luxE, and flavin reductase) may be operatively linked to a constitutive promoter. That is, in such embodiments, luxC, luxD, luxE, and flavin reductase are continuously produced, and luxA and luxB are only produced in response to the presence of the analyte in the stem cell's environment. Thus, when the stem cell is exposed to the analyte, each of the proteins necessary for generating autobioluminescence will be produced, and consequently, the stem cell will emit the autobioluminescent signal. Therefore, in each of the above embodiments, presence of the autobioluminescent signal indicates presence of the analyte in the stem cell's environment.

Moreover, the stem cell may comprise a regulatory mechanism allowing for control of lux expression by an exogenous effector molecule. The regulatory mechanism may, for example, be a tetracycline-controlled expression system capable of inducing expression, such as Tet-On. The regulatory mechanism is advantageous in that it may generate a greater genetic induction of the autobioluminescent signal.

In embodiments wherein at least one of the nucleic acids encoding each of luxA, luxB, luxC, luxD, luxE, and flavin reductase are operatively linked to at least one analyte-responsive response element, the stem cell may comprise an at least one analyte-responsive reverse transactivator. The at least one analyte-responsive reverse transactivator may be operatively linked to a constitutive promoter, such as the chicken beta-actin promoter. The at least one analyte-responsive reverse transactivator may bind to, and thereby activate, the at least one analyte-responsive response element in the presence of the analyte. Once activated, the at least one analyte-responsive response element initiates transcription of the at least one nucleic acid that is operatively linked to the at least one analyte-responsive response element.

By way of example, in any of the embodiments described herein, the at least one analyte-responsive response element may comprise a tetracycline responsive element (TRE), and the at least one analyte-responsive reverse transactivator may comprise a reverse tetracycline-controlled transactivator. In such embodiments, the TRE may be linked to at least one of the nucleic acids encoding each of luxA, luxB, luxC, luxD, luxE, and flavin reductase.

The reverse tetracycline-controlled transactivator may bind to the TRE in the presence of tetracycline, or one of its analogs like doxycycline, thereby activating the TRE. This activation initiates transcription of the at least one nucleic acid operatively linked to the TRE. For example, in embodiments wherein all of the nucleic acids encoding luxA, luxB, luxC, luxD, luxE, and flavin reductase are operatively linked to the TRE, each of the corresponding proteins are produced. As a result, the stem cell will emit the autobioluminescent signal. Thus, in such an embodiment, the stem cell emits the autobioluminescent signal in response to the presence of tetracycline or one of its analogs in the stem cell's environment.

3. Repressible Autobioluminescent Signal

In embodiments wherein the autobioluminescent signal is repressible, the stem cell ceases to emit the autobioluminescent signal when exposed to an external stimulus. The external stimulus may, for example, comprise an analyte, an environmental condition (e.g., temperature, radiation, and/or light), or transcriptional activation and/or deactivation of one of more nucleic acids.

In embodiments wherein the external stimulus comprises an analyte, the stem cell may comprise a regulatory mechanism allowing for control of lux expression by an exogenous effector molecule. The regulatory mechanism may, for example, be a tetracycline-controlled expression system capable of inducing expression, such as Tet-Off. The regulatory mechanism is advantageous in that it may generate a repressible autobioluminescent signal.

In some embodiments, the stem cell may comprise at least one analyte-responsive response element. As detailed above, the at least one analyte-responsive response element may be operatively linked to at least one of the nucleic acids encoding each of luxA, luxB, luxC, luxD, luxE, and flavin reductase. For example, the at least one analyte-responsive response element may be operatively linked to all of said nucleic acids. In other embodiments, the at least one analyte-responsive response element may be operatively linked to a subset of at least one of the nucleic acids encoding each of luxA, luxB, luxC, luxD, luxE, and flavin reductase (i.e., one, two, three, etc. of the foregoing nucleic acids). At least one of said nucleic acids not linked to the at least one analyte-responsive response element may be operatively linked to a constitutive promoter such that the at least one nucleic acid is constitutively expressed. For example, if the luxA and luxB nucleic acids are linked to at least one analyte-responsive response element, then the luxC, luxD, luxE, and flavin reductase nucleic acids may be linked to a constitutive promoter.

The stem cell may comprise at least one analyte-responsive transactivator capable of binding to, and thereby activating, the at least one analyte-responsive response element. The at least one analyte-responsive transactivator may be operatively linked to a constitutive promoter, e.g., the chicken beta-actin promoter, such that there is continuous production of the at least one analyte-responsive transactivator. In such embodiments, the at least one analyte-responsive transactivator activates the at least one analyte-responsive response element, which then initiates transcription of the at least one nucleic acid that is operatively linked to the at least one analyte-responsive response element. Any at least one nucleic acid not operatively linked to the at least one analyte-responsive response element may be linked to a constitutive promoter. Thus, in such embodiments, the stem cell may emit an autobioluminescent signal through expression of the nucleic acids encoding each of encoding each of luxA, luxB, luxC, luxD, luxE, and flavin reductase.

In the presence of the analyte, however, the at least one analyte-responsive transactivator no longer binds to, and thereby activates, the at least one analyte-responsive response element. Instead, the at least one analyte-responsive transactivator binds to the analyte. The analyte may be any suitable analyte that may bind to the at least one analyte-responsive transactivator, thus preventing the at least one analyte-responsive transactivator from binding to, and thereby activating, the at least one analyte-responsive response element.

Thus, in the presence of the analyte, the at least one analyte-responsive transactivator fails to activate the at least one analyte-responsive response element. Consequently, the at least one analyte-responsive response element does not initiate transcription of the at least one nucleic acid that is operatively linked to the at least one analyte-responsive response element. As a result, at least one of the nucleic acids encoding luxA, luxB, luxC, luxD, luxE, and flavin reductase is not expressed. Consequently, the autobioluminescent signal may be repressed. That is, the stem cell may emit a less robust or no autobioluminescent signal in the presence of the analyte.

By way of example, in any of the above embodiments, the at least one analyte-responsive response element may comprise a tetracycline responsive element (TRE), and the at least one analyte-responsive transactivator comprises a tetracycline-controlled transactivator. In such embodiments, the tetracycline-controlled transactivator binds to, and thereby activates, the TRE. In some embodiments, all of the nucleic acids encoding each of luxA, luxB, luxC, luxD, luxE, and flavin reductase may be operatively linked to the TRE. Thus, activation of the TRE initiates transcription of each of the nucleic acids operatively linked to the TRE, which ultimately results in constitutive production of each of luxA, luxB, luxC, luxD, luxE, and flavin reductase. As a result, the stem cell may emit the autobioluminescent signal. In other embodiments, only a subset (i.e., one, two, three etc.) of the foregoing nucleic acids are operatively linked to the TRE, and in such cases, activation of the TRE initiates transcription of only the nucleic acids to which the TRE is operatively linked.

However, in the presence of tetracycline or one of its analogs, the tetracycline-controlled transactivator binds to the tetracycline or one of its analogs, rather than the TRE. As a result, there is reduced transcription of the nucleic acids that are operatively linked to the TRE, thereby resulting in a reduced autobioluminescent signal. Thus, in such an embodiment, the autobioluminescent signal may be repressed in the presence of tetracycline or one of its analogs.

4. Tissue-Specific Autobioluminescent Signal

In embodiments wherein the autobioluminescent signal is tissue-specific, the autobioluminescent signal is only emitted when the stem cell differentiates into a tissue cell. A tissue cell is a specialized (i.e., differentiated) cell that has tissue-specific structures that allow it to perform specialized functions, e.g., a muscle, nerve, or bone cell. The tissue cell may comprise, for example, any myocyte, neuron, neuroglia, osteoclast, osteocyte, or osteoblast.

In said embodiments, at least one of the nucleic acids encoding luxA, luxB, luxC, luxD, luxE, and flavin reductase is operatively linked to a tissue-specific promoter. The tissue-specific promoter may be any promoter that controls gene expression in a tissue-dependent manner, i.e., the promoter is only active in certain tissue cell types. For example, the tissue-specific promoter may comprise the cardiomyocyte-specific promoter TNNT2, the human adipose-tissue-specific promoter hAP2, or any other tissue-specific promoter.

In said embodiments, the at least one nucleic acid to which the tissue-specific promoter is operatively linked is only expressed when the stem cell is differentiated into a type of tissue cell in which the tissue-specific promoter is active. That is, there may be tissue-specific transcription of the at least one nucleic acid. Any of the at least one nucleic acids encoding luxA, luxB, luxC, luxD, luxE, and flavin reductase that is not operatively linked to the tissue-specific promoter may be operatively linked to a constitutive promoter such that the at least one nucleic acid is operatively is continuously expressed.

For example, in some embodiments of a stem cell capable of emitting a tissue-specific autobioluminescent signal, the luxA nucleic acid and the luxB nucleic acid may be operatively linked to a tissue-specific promoter. Thus, luxA and luxB are only expressed when the stem cell is differentiated into a type of tissue cell in which the tissue-specific promoter is active. Such a configuration may result in tissue-specific transcription of the luxA nucleic acid and the luxB nucleic acid, such that there is tissue-specific expression of the luciferase component necessary for autobioluminescence.

The tissue-specific promoter may comprise, for example, a TNNT2 promoter, which is a cardiomyocyte-specific promoter. Prior to differentiation of the stem cell, the TNNT2 promoter remains inactive, and luxA and luxB are not expressed. If the stem cell is differentiated into a cardiomyocyte cell, the TNNT2 promoter becomes active, thereby initiating transcription of the luxA nucleic acid and the luxB nucleic acid. As a result, luxA and luxB are expressed.

In said embodiments, the luxC nucleic acid, the luxD nucleic acid, the luxE nucleic acid, and the flavin reductase nucleic acid may be operatively linked to a constitutive promoter. Thus, in said embodiments, there is a continuous expression of the nucleic acids encoding each of luxC, luxD, luxE, and flavin reductase, thereby resulting in continuous production of the luciferin component and the $FMNH_2$ co-substrate for the chemical reaction resulting in autobioluminescence.

Thus, in such embodiments, when the tissue-specific promoter is activated, there is expression of luxA and luxB. As a result, there is expression of all proteins needed to emit the autobioluminescent signal. However, without the activation of the tissue-specific promoter, only expression of luxC, luxD, luxE, and flavin reductase occurs, which is insufficient to emit an autobioluminescent signal. As a result, emission of the autobioluminescent signal coincides with the onset of differentiation into the type of tissue cell in which the tissue-specific promoter is expressed, i.e., the autobioluminescent signal is tissue-specific.

Ultimately, the above embodiments of a stem cell emitting a constitutive, inducible, repressible, or tissue-specific autobioluminescent signal via the lux system may enable substrate-free autobioluminescent imaging of stem cells under in vitro and/or in vivo modalities in, for example, a high-throughput manner. The autobioluminescent signal is emitted in real-time to bioindicate cellular and molecular mechanisms coupled to bioluminescent outputs. Moreover, due to the autobioluminescent phenotype, the stem cells may be continuously interrogated without investigator interaction to initiate bioluminescence, thus allowing for the assessment of both signal duration and intensity dynamics from a single sample. Further, the autobioluminescent phenotype of the stem cells may enable non-invasive continuous optical imaging in a variety of applications, including but not limited to, real-time, non-invasive, continuous, and substrate-free tracking, identifying, and/or measuring the stem cells' viability, migration, fate, and/or lineage-specific differentiation. Moreover, new capabilities for the eukaryotic bacterial luciferase system may also be enabled, such as single cell imaging (see C. Gregor et al., "Autonomous bioluminescence imaging of single mammalian cells with the bacterial bioluminescence system," Proc. Natl. Acad. Sci., Vol 116, No. 52, 2019), organelle tagging, use of bioluminescence for sorting cells using flow cytometery, and visualizing smaller numbers of cells in animal models. Thus, the disclosed embodiments may effectively remedy many of the significant impediments hindering the implementation of stem cell-based therapies in clinical practice and would be a significant asset to the regenerative medicine field.

III. Specialized Cell Comprising an Autobioluminescent Phenotype

A stem cell-derived autonomously bioluminescent cell is disclosed. The stem cell-derived autonomously bioluminescent cell comprises an autonomously bioluminescent eukaryotic cell differentiated from an autonomously bioluminescent stem cell.

The stem cell-derived autonomously bioluminescent cell may comprise any cell that is becoming, or has become, specialized for a particular function. For example, cells that are specialized for a particular function include, for example, cells that have acquired one or more morphological characteristics and/or functions that differ from those of the initial cell type. The stem cell-derived autonomously bioluminescent cell emits a constitutive autobioluminescent signal.

The autonomously bioluminescent stem cell may comprise any embodiment of a stem cell comprising an autonomously bioluminescent phenotype disclosed herein. Moreover, the stem cell-derived autonomously bioluminescent cell may inherit the characteristics of any embodiment of a stem cell comprising an autonomous bioluminescent phenotype from which the stem cell-derived autonomously bioluminescent cell is derived.

Both the stem cell-derived autonomously bioluminescent cell and the autonomously bioluminescent stem cell from which it is derived express an autobioluminescent signal in the absence of an exogenous luminescent stimulator, such as an aldehyde substrate. The stem cell-derived autonomously bioluminescent cell emits an autonomous bioluminescent signal via production of luxA, luxB, luxC, luxD, luxE, and flavin reductase through the chemical reaction disclosed herein.

The stem cell-derived autonomously bioluminescent cells may emit an approximately similar level of autobioluminescent signal as a level of autobioluminescent signal emitted from the autonomously bioluminescent stem cell from which the stem cell-derived autonomously bioluminescent cell is derived.

A stem cell-derived autonomously bioluminescent cell is advantageous in that it may enable substrate-free autobioluminescent imaging of specialized, or differentiating/differentiated, cells under in vitro and/or in vivo conditions in, for example, a high-throughput manner. Given the ability of the stem cell-derived autonomously bioluminescent cell to produce bioluminescence without the need for an investigator to add an exogenous substrate, the cell has applications in, for example, real-time, non-invasive, continuous, and substrate-free tracking, identifying, and/or measuring the cells' viability, migration, and/or fate.

IV. Cells Comprising an Overexpression of luxC, luxD, luxE, and Flavin Reductase In some embodiments of a stem cell comprising an autonomous phenotype, at least one of luxC, luxD, luxE, and flavin reductase may be present at a level greater than a level of at least one of luxA and luxB. In some embodiments, luxC, luxD, luxE, and flavin reductase may be present at a combined level of from ten times to forty times greater than a combined level of luxA and luxB. In some embodiments, luxC, luxD, luxE, and flavin reductase may be present at a combined level of from twenty times to thirty times greater than a combined level of luxA and luxB. In some embodiments, luxC, luxD, luxE, and flavin reductase may be present at a combined level of from fifteen times to twenty times greater than a combined level of luxA and luxB.

Advantageously, each of these embodiments generates an overproduction of luxC, luxD, luxE, and flavin reductase relative to luxA and luxB. Indeed, it was surprisingly and unexpectedly discovered that in order to maximize the bioluminescent signal of a stem cell comprising an autonomous phenotype, it is necessary to overexpress the nucleic acids encoding each of luxC, luxD, luxE, and flavin reductase (the luciferin production portion of the lux cassette) relative to the nucleic acids encoding each of luxA and luxB (the luciferase production portion of the lux cassette) (see Working Example 1).

Figure 2A:
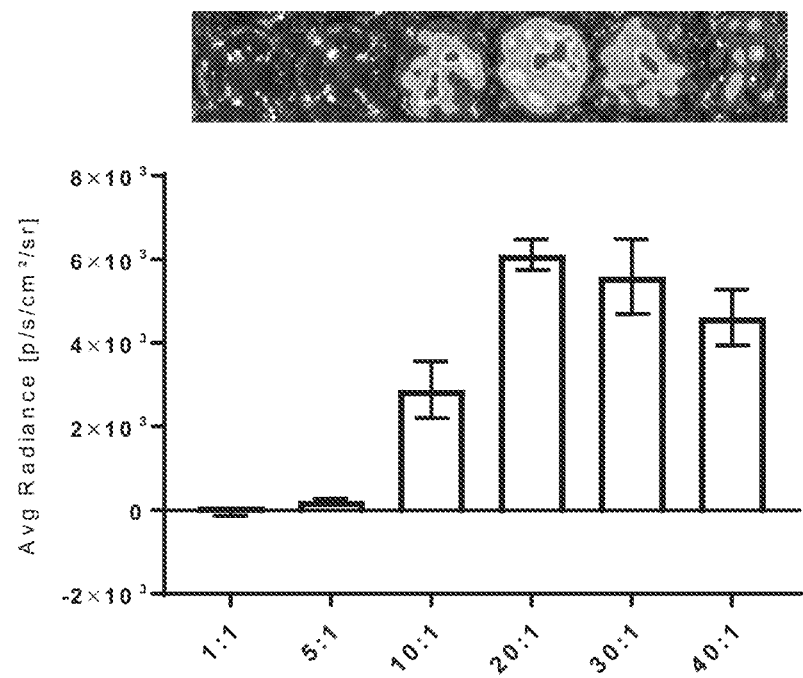
FIGS. 2A-2D. Varying molar ratios of luxCDEF to luxAB results in autobioluminescent output in tested cell types.
Figure 2B:
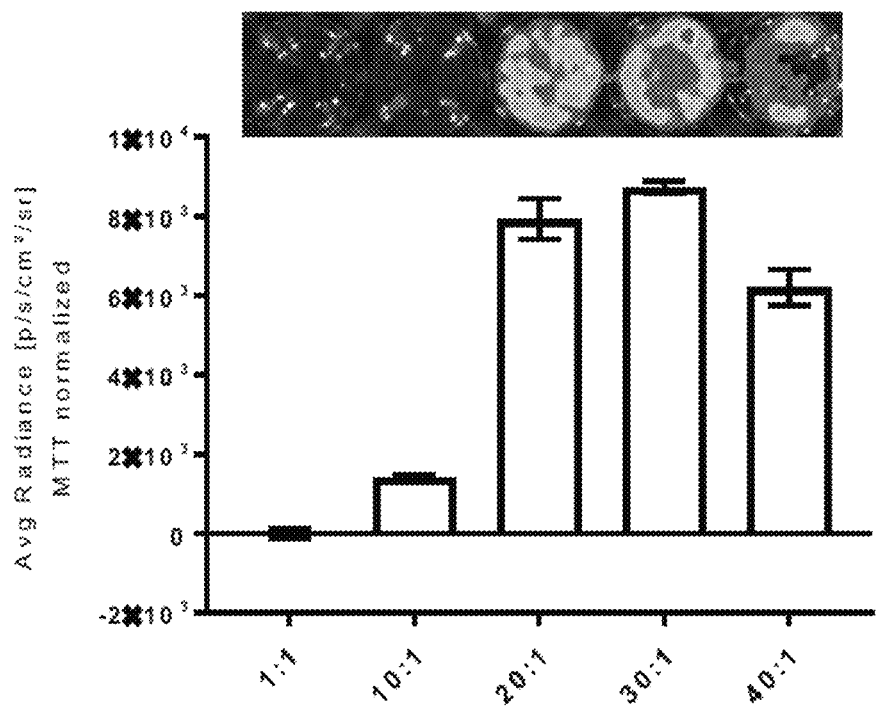

Moreover, it was unexpectedly discovered that a common ratio of overexpression of the nucleic acids encoding each of luxC, luxD, luxE, and flavin reductase relative to the nucleic acids encoding each of luxA and luxB consistently produced the highest level of autonomous luminescent output. That is, an approximate 20:1-30:1 ratio maximizes autonomous luminescent output in induced pluripotent stem cells and human adipose derived mesenchymal stem cells (FIGS. 2A-2B, respectively). Such a result is surprising and unexpected given the differences in the physiology and metabolic activity between cell types. It would be expected that this ratio would necessarily greatly differ for every cell type, given that each cell type has a different basal oxidation states and availability to the metabolic resources required for luciferin generation.

The benefits of overexpressing the nucleic acids encoding each of luxC, luxD, luxE, and flavin reductase relative to the nucleic acids encoding each of luxA and luxB is counterintuitive and unexpected for at least two reasons. First, the luciferin compound produced by the system is a long chain aldehyde that is cytotoxic at elevated levels. An overexpression of the luciferin production portion of the lux cassette may result in an accumulation of the long chain aldehyde, thereby increasing the risk of cytotoxic effects. These effects may, in turn, negatively impact the health of the stem cell, which would cause a reduction of autobioluminescence.

Second, the luxC, luxD, luxE, and flavin reductase genes re-route metabolites from both metabolic and oxidation/reduction processes within the cell. Therefore, it would be expected that an overexpression of the nucleic acids encoding each of luxC, luxD, luxE, and flavin reductase relative to the nucleic acids encoding each of luxA and luxB would negatively impact cellular health, growth, and physiology due to either cytotoxicity resulting from an accumulation of the long chain aldehyde and/or interference with metabolic activity. Reduced cellular health would then in turn result in reduced autonomous luminescent output.

Therefore, there is no reason to expect that an overexpression of the nucleic acids encoding each of luxC, luxD, luxE, and flavin reductase would produce the most robust bioluminescent output. Surprisingly, however, a stem cell comprising an autonomous phenotype demonstrating overproduction of luxC, luxD, luxE, and flavin reductase relative to luxA and luxB unexpectedly emitted increased autonomous luminescence while continuing to present normal physiology and metabolic activity levels (See Working Example 1).

Thus, embodiments of a stem cell comprising the disclosed overproduction of luxC, luxD, luxE, and flavin reductase to luxA and luxB may produce a robust autobioluminescent signal, which may be beneficial for detecting, imaging, measuring, and/or quantifying the signal. Such embodiments may emit a bioluminescent signal of at least 5 times, at least 10 times, at least 20 times, at least 50 times, at least 100 times, at least 200 times, at least 500 times, and/or at least 1000 times greater than a bioluminescent signal emitted from autobioluminescent cell(s) not overexpressing luxA and luxB relative to luxC luxD, luxE, and flavin reductase.

V. Cells Comprising the Lux Cassette Expressed from Distinct Vectors

In some embodiments of a cell comprising an autonomous phenotype, each of luxA, luxB, luxC, luxD, luxE, and flavin reductase are expressed independently from separate vectors, such as six distinct plasmids. In such embodiments, each of the vectors may have a promoter, whether inducible or constitutive, that drives expression of the gene present on the vector. In said embodiments, the stem cell may beneficially overexpress luxC, luxD, luxE, and flavin reductase relative to luxA and luxB, as discussed above.

Advantageously, the expression of each of luxA, luxB, luxC, luxD, luxE, and flavin reductase from six vectors results in a robust autobioluminescent phenotype. Indeed, it was surprisingly and unexpectedly discovered that expressing each of the aforementioned genes independently from separate plasmids results in a significantly increased bioluminescent signal for the autobioluminescent cells disclosed herein. Indeed, as further detailed in Working Example 1, the six vector approach results in a significant increase in light production as compared to either expressing multiple genes from a single plasmid or multiple genes from a single promoter when the full set of genes are expressed across multiple plasmids.

The success of the six vector approach is counterintuitive and unexpected. Indeed, literature directly teaches away from expressing, at least, luxA and luxB from separate plasmids or separate promoters. Specifically, previous work has shown that expression of the luxA and luxB genes from either (1) different plasmids, (2) different promoters on the same plasmid, or (3) fused to form a single protein under the control of a single promoter all reduced light production relative to unfused co-expression from a single promoter in human cells (See, e.g., S. Patterson, "Optimization of Bacterial Luciferase for Expression in Mammalian Cells," PhD diss., University of Tennessee, 2003.). It has long been explained that these aforementioned strategies failed to produce as much light output because the luxA and luxB polypeptides transition through a molten globule form during folding and require one another as co-scaffolds to correctly assemble into a functional heterodimer (See G. C. Flynn, "Individual subunits of bacterial luciferase are molten globules and interact with molecular chaperones" Proc. Natl. Acad. Sci. USA, Vol. 90, pp. 10826-10830, November 1993.). Further, literature states that when the luxA and luxB polypeptides are not co-expressed from the same promoter, their polypeptide sequences do not begin the folding process at the same time and space within the cell. Id. Once the polypeptide sequences have folded independently, the two cannot form a functional luciferase, and they cannot re-fold to the correct orientation. Id. Therefore, there was no reason to expect that the six vector approach would produce a highly robust bioluminescent output.

Nonetheless, in contradiction to long-standing literature, it has been found that expression of luxA and luxB from separate plasmids does, in fact, produce robust light production exceeding that of expressing the two from the same plasmid (see Working Example 1). Thus, embodiments of a stem cell comprising each of luxA, luxB, luxC, luxD, luxE, and flavin reductase expressed independently from separate vectors are disclosed herein. Furthermore, the six vector approach easily facilitates implementing the aforementioned beneficial ratio of an overexpression of the nucleic acids encoding each of luxC, luxD, luxE, and flavin relative to the nucleic acids encoding each of luxA and luxB (the luciferase production portion of the lux cassette). Ultimately, the increase in light production resulting from gene expression on individual plasmids in the advantageous ratio enables new capabilities for the eukaryotic bacterial luciferase system, such as single cell imaging (see C. Gregor et al., Autonomous bioluminescence imaging of single mammalian cells with the bacterial bioluminescence system, Proc. Natl. Acad. Sci. USA, Vol 116, No. 52, 2019), organelle tagging, use of bioluminescence for sorting cells using flow cytometery, and visualizing smaller numbers of cells in animal models.

VI. Methods and Kits for Producing a Stem Cell Comprising an Autonomous Luminescent Phenotype Disclosed herein are methods and kits for producing a stem cell comprising an autonomous luminescent phenotype. The stem cell may be any type of stem cell. For example, the stem cell may be an adult stem cell (e.g., a tissue-specific stem cell), an embryonic (or pluripotent) stem cell, or an induced pluripotent stem cell (iPSC). It is understood that all progeny may not be identical to the parental cell since there may be mutations that occur during replication.

1. Constitutive Autobioluminescent Signal

Methods are disclosed for producing a stem cell comprising an autonomous luminescent phenotype, wherein the stem cell emits a constitutive autobioluminescent signal.

The methods comprise transfecting a stem cell with a luxA nucleic acid, a luxB nucleic acid, a luxC nucleic acid, a luxD nucleic acid, a luxE nucleic acid, and a flavin reductase nucleic acid. After the stem cell is transfected with said nucleic acids, the stem cell constitutively produces luxA, luxB, luxC, luxD, luxE, and flavin reductase, such that the stem cell emits a constitutive luminescent signal.

In some embodiments, the method comprises transfecting the stem cell with at least one vector comprising at least one of the nucleic acids encoding each of luxA, luxB, luxC, luxD, luxE, and flavin reductase. That is, the method may comprise transfecting the stem cell with any number of vectors comprising any configuration of at least one of the nucleic acids encoding each of luxA, luxB, luxC, luxD, luxE, and flavin reductase.

For example, in some embodiments, the method comprises transfecting a stem cell with six vectors, wherein each of the vectors comprises one of the luxA nucleic acid, the luxB nucleic acid, the luxC nucleic acid, the luxD nucleic acid, the luxE nucleic acid, and the flavin reductase nucleic acid (i.e., one per vector). Each nucleic acid may be operatively linked to a constitutive promoter. Such an embodiment may result in continual transcription of each of the aforementioned nucleic acids, such that there is constitutive expression of the components necessary for the chemical reaction resulting in autobioluminescence.

In alternative embodiments, the method comprises transfecting a stem cell with a first vector and a second vector. In such embodiments, the first vector may comprise a luxA nucleic acid and a luxB nucleic acid. The luxA nucleic acid and the luxB nucleic acid may be operatively linked to a first constitutive promoter. As a result, there may be continual transcription of the luxA nucleic acid and the luxB nucleic acid, such that there is constitutive expression of the luciferase component necessary for the chemical reaction resulting in autobioluminescence.

In said embodiments, the second vector may comprise a luxC nucleic acid, a luxD nucleic acid, a luxE nucleic acid, and a flavin reductase nucleic acid. The nucleic acids encoding each of luxC, luxD, luxE, and flavin reductase may be operatively linked to a second constitutive promoter. The first constitutive promoter and the second constitutive promoter may comprise the same promoter or different promoters. Such a configuration may result in continuous transcription of the nucleic acids encoding each of luxC, luxD, luxE, and flavin reductase, such that there is continuous expression of the aldehyde substrate and the $FMNH_2$ co-substrate required for autobioluminescence.

Post-transfection, the stem cell may constitutively express the nucleic acids encoding each of luxA, luxB, luxC, luxD, luxE, and flavin reductase, which may result in continuous self-synthesizing of all the substrates required for luminescent signal production. This production may operate autonomously and in real-time. Consequently, the stem cell may emit a constitutive autobioluminescent signal that may be imaged to bioindicate cellular and molecular mechanisms coupled to bioluminescent outputs.

The six vector and two vector systems disclosed herein are highly advantageous for generating a robust autobioluminescent signal. First, with respect to the lux cassette, it is believed that transcriptional activity is lower for nucleic acids positioned distal to a promoter. Thus, separating the lux nucleic acids onto more than one independent vector mitigates the issue, as it necessarily lessens the distance between some of the nucleic acids and the promoter as compared to positioning all of the nucleic acids onto a single vector.

Second, the six vector and two vector systems allow for varying the ratio of luxA and luxB nucleic acids to luxC, luxD, luxE, and flavin reductase nucleic acids, the advantages of which are disclosed earlier herein. Accordingly, in some embodiments, the methods may comprise transfecting the stem cell with an amount of the nucleic acids encoding luxC, luxD, luxE, and flavin reductase that is from ten to forty times greater than an amount of the nucleic acids encoding luxA and luxB. Preferably, the methods may comprise transfecting the stem cell with an amount of the nucleic acids encoding luxC, luxD, luxE, and flavin reductase that is from twenty to thirty times greater than an amount of the nucleic acids encoding luxA and luxB. For example, in the disclosed two vector system, the method may preferably comprise transfecting an amount of the second vector that is from twenty to thirty times of an amount of the first vector. Transfecting the nucleic acids in these amounts will achieve the aforementioned advantageous ratio of luxA and luxB nucleic acids to luxC, luxD, luxE, and flavin reductase nucleic acids, thereby resulting in a robust autonomous luminescent phenotype.

A kit for producing a stem cell emitting a constitutive autobioluminescent signal is disclosed. The kit is used in reference to a combination of articles that facilitate a process, method, assay, analysis, or manipulation of a sample. The kit comprises at least one vector comprising at least one of the nucleic acids encoding each of luxA, luxB, luxC, luxD, luxE, and flavin reductase. The kit may comprise any number of vectors comprising any number of configurations of at least one of the nucleic acids encoding each of luxA, luxB, luxC, luxD, luxE, and flavin reductase For example, in some embodiments, the kit may comprise six vectors in accordance with the six vector system or two vectors in accordance with the two vector system. In some embodiments, the vector(s) having the nucleic acids encoding luxC, luxD, luxE, and flavin reductase are present in the kit at an amount of from ten to forty times greater than an amount of the vector(s) having the nucleic acids encoding luxA and luxB. More preferably, the vector(s) having the nucleic acids encoding luxC, luxD, luxE, and flavin reductase may be present at an amount of from twenty to thirty times greater than an amount of the vector(s) having the nucleic acids encoding luxA and luxB. As detailed herein, such a ratio is advantageous for producing a maximal luminescent signal. Therefore, a kit comprising said amounts would be particularly advantageous in that a user of the kit could develop a stem cell emitting a robust autobioluminescent signal.

In some embodiments, the kit may comprise chemical reagents or enzymes required for the method, primers and probes, as well as any other components. For example, the kit may comprise necessary reagents and tools for transforming a stem cell with the at least one vector, such that the user may produce a stem cell comprising an autonomous luminescent phenotype. In such embodiments, once transfected with the at least one vector, the stem cell may express the nucleic acids encoding each of luxA, luxB, luxC, luxD, luxE, and flavin-reductase, such that the stem cell produces an autonomous constitutive bioluminescent signal in the absence of an exogenously added substrate, such as aldehyde.

The kit may also contain written instructions describing how to use the kit. For example, the instructions may pertain to methods of using the kit, including methods for transforming a stem cell with the at least one vector. Such instructions are advantageous in that they may increase the ease with which a user may use the kit.

2. Inducible Autobioluminescent Signal

Methods are disclosed for producing a stem cell comprising an autonomous luminescent phenotype, wherein the stem cell emits an inducible autobioluminescent signal when exposed to an analyte. The method comprises transfecting the stem cell with at least one vector. The at least one vector comprises at least one of the nucleic acids encoding each of luxA, luxB, luxC, luxD, luxE, and flavin reductase, wherein at least one of the nucleic acids is operatively linked to at least one analyte-responsive regulatory element.

The at least one analyte-responsive regulatory element may be any response element capable of being regulated by the presence of an analyte. Examples of an analyte-responsive regulatory element include, but are not limited to, the estrogen response element, the androgen response element, the metal response element, the aromatic hydrocarbon response element, the electrophile response element, the retinoic acid and retinoid X response elements, the antioxidant response element, the glucocorticoid response element, the calcium-response element, the thyroid hormone response element, and the growth hormone response element. The analyte may be any analyte that may bind to, and thereby activate, the analyte-responsive response element.

The method may comprise transfecting the stem cell with any number of vectors. For example, in some embodiments, the method may comprise transfecting the stem cell with a single vector comprising all of the nucleic acids encoding each of luxA, luxB, luxC, luxD, luxE, and flavin reductase operatively linked to the at least one analyte-responsive response element. In such embodiments, once transfected with the single vector, the stem cell may produce an autobioluminescent signal in the presence of the analyte. That is, the analyte may bind to, and thereby activate, the analyte-responsive response element. The activated analyte-responsive response element causes an upregulation in transcription of the nucleic acids to which it is operatively linked, i.e., those encoding each of luxA, luxB, luxC, luxD, luxE, and flavin reductase. This leads to production of the corresponding proteins that ultimately generate the autobioluminescent signal.

In other embodiments, for example, the method may comprise transfecting the stem cell with multiple vectors. For example, there may be six vectors, wherein each vector contains one of the nucleic acids encoding each of luxA, luxB, luxC, luxD, luxE, and flavin reductase (i.e., each of the foregoing is expressed from a unique vector). At least one of the nucleic acids may be linked to the at least one analyte-response response element. Any nucleic acid not linked to the at least one analyte-response response element may be linked to a constitutive promoter.

In other embodiments, the method may comprise transfecting the stem cell a first vector and a second vector. For example, in such embodiments, the first vector may comprise the nucleic acids encoding each of luxA and luxB operatively linked to an analyte-responsive response element. The second vector may comprise the nucleic acids encoding each of luxC, luxD, luxE, and flavin reductase operatively linked to a constitutive promoter. Once the stem cell is transfected with the first vector and the second vector, luxD, luxE, and flavin reductase are continuously produced, and luxA and luxB are only produced in response to the presence of the analyte in the stem cell's environment. Thus, when the stem cell is exposed to the analyte, the proteins necessary for generating autobioluminescence will be produced, and consequently, the stem cell will emit the autobioluminescent signal.

Moreover, the method may comprise transfecting a stem cell with a regulatory mechanism allowing for control of lux expression by an exogenous effector molecule. In some embodiments, the regulatory mechanism may be a tetracycline-controlled expression system capable of inducing expression, for example, Tet-On. Such a regulatory mechanism is advantageous in that it may generate a greater genetic induction of the autobioluminescent signal.

In any of the above embodiments, the method may comprise transfecting a stem cell with a vector comprising at least one analyte-responsive reverse transactivator. The at least one analyte-responsive reverse transactivator may be capable of activating the at least one analyte-responsive response element in the presence of the analyte. Once activated, the at least one analyte-responsive response element initiates transcription of the at least one nucleic acid that is operatively linked to the at least one analyte-responsive response element. The at least one analyte-responsive reverse transactivator may be operatively linked to a constitutive promoter, such as the chicken beta-actin promoter, to ensure continuous production of the at least one analyte-responsive reverse transactivator.

As an example, the at least one analyte-responsive response element may comprise a tetracycline responsive element (TRE), and the at least one analyte-responsive reverse transactivator may comprise a tetracycline-controlled reverse transactivator. In some embodiments, the nucleic acids encoding each of luxA, luxB, luxC, luxD, luxE, and flavin reductase are operatively linked to the TRE. In such embodiments, the reverse tetracycline-controlled transactivator binds to, and thereby activates, the TRE in the presence of tetracycline, or one of its analogs like doxycycline. This activation initiates transcription of the nucleic acids operatively linked to the TRE, which ultimately results in production of the autobioluminescent signal. Thus, in such an embodiment, the stem cell emits the autobioluminescent signal in the presence of tetracycline or one of its analogs.

A kit for producing a stem cell having inducible autobioluminescence is likewise disclosed. The kit is used in reference to a combination of articles that facilitate a process, method, assay, analysis, or manipulation of a sample.

The kit comprises any vector(s) disclosed above in the methods for producing a stem cell comprising an autonomous luminescent phenotype, wherein the stem cell emits an inducible autobioluminescent signal. The kit may comprise any number of vectors (e.g., one, two, three, etc.) comprising any number of configurations of at least one of the nucleic acids encoding each of luxA, luxB, luxC, luxD, luxE, and flavin reductase.

In some embodiments, the kit may comprise an amount of the analyte. The analyte may be any analyte that may bind to, and therefore activate, the analyte-responsive response element. The analyte may be any analyte that may bind to the analyte-responsive reverse transactivator, thereby causing it to bind to the analyte-responsive response element, thereby resulting in an inducible autobioluminescent signal.

In some embodiments, the kit may comprise chemical reagents or enzymes required for the method, primers and probes, as well as any other components. For example, the kit may comprise necessary reagents and tools for transforming the stem cell with the vector(s), such that the user may produce a stem cell that emits an autobioluminescent signal in the presence of the analyte, i.e., an inducible signal. The kit may also contain written instructions describing how to use the kit. For example, the instructions may pertain to methods of using the kit, including methods for transforming a stem cell with a vector. Such instructions are advantageous in that they may increase the ease with which a user may use the kit.

3. Repressible Autobioluminescent Signal

Methods are disclosed for producing a stem cell comprising an autonomous luminescent phenotype, wherein the stem cell emits an autobioluminescent signal that is repressible through exposure to an analyte. The method comprises transfecting the stem cell with at least one vector. The at least one vector comprises at least one of the nucleic acids encoding each of luxA, luxB, luxC, luxD, luxE, and flavin reductase, wherein at least one of the nucleic acids is operatively linked to at least one analyte-responsive regulatory element. When activated, the analyte-responsive response element initiates translation of the nucleic acids to which it is operatively linked. As disclosed above, the at least one analyte-responsive regulatory element may be any response element capable of being regulated by the presence of an analyte.

The method may comprise transfecting the stem cell with any number of vectors. For example, in some embodiments, the method may comprise transfecting the stem cell with a single vector comprising all of the nucleic acids encoding each of luxA, luxB, luxC, luxD, luxE, and flavin reductase operatively linked to the at least one analyte-responsive response element.

In some embodiments, the method may comprise transfecting the stem cell with multiple vectors. For example, there may be six vectors, wherein each vector contains one of the nucleic acids encoding each of luxA, luxB, luxC, luxD, luxE, and flavin reductase (i.e., each of the foregoing is expressed from a unique vector). At least one of the nucleic acids may be linked to the at least one analyte-response response element. Any nucleic acid not linked to the at least one analyte-response response element may be linked to a constitutive promoter.

In embodiments employing multiple vectors, the method may comprise transfecting the stem cell with a first vector and a second vector. For example, the first vector may comprise at least one analyte-responsive response element operatively linked to at least one of the nucleic acids encoding each of luxA, luxB, luxC, luxD, luxE, and flavin reductase. The second vector may comprise at least one of the nucleic acids encoding each of luxA, luxB, luxC, luxD, luxE, and flavin reductase operatively linked to a constitutive promoter. For example, in such embodiments, the first vector may comprise the nucleic acids encoding each of luxA and luxB operatively linked to an analyte-responsive response element. The second vector may comprise the nucleic acids encoding each of luxC, luxD, luxE, and flavin reductase operatively linked to a constitutive promoter.

In any of the above embodiments, the method comprises transfecting a stem cell with a regulatory mechanism allowing for reduction in lux expression by an exogenous effector molecule. The regulatory mechanism may, for example, be a tetracycline-controlled expression system capable of repressing expression, such as Tet-Off.

In such embodiments, the method may comprise transforming a stem cell with a vector comprising at least one analyte-responsive transactivator. The at least one analyte-responsive transactivator may be capable of binding to, and thereby activating, the at least one analyte-responsive response element. The at least one analyte-responsive transactivator may be operatively linked to a constitutive promoter, such as the chicken beta-actin promoter, to ensure continuous production of the at least one analyte-responsive transactivator.

In such embodiments, however, presence of the analyte impacts the binding of the at least one analyte-responsive transactivator to the at least one analyte-responsive response element. That is, when the stem is exposed to the analyte, the analyte binds to the at least one analyte-responsive transactivator, preventing it from activating the at least one analyte-responsive response element. Thus, in the presence of the analyte, the at least one analyte-responsive transactivator fails to activate the at least one analyte-responsive response element. Consequently, the at least one analyte-responsive response element does not initiate transcription of the at least one nucleic acid to which it is operatively linked. As a result, at least one of the nucleic acids encoding luxA, luxB, luxC, luxD, luxE, and flavin reductase is not expressed. Consequently, the autobioluminescent signal may be repressed. That is, the stem cell may emit a less robust or no autobioluminescent signal in the presence of the analyte.

By way of example, in any of the above embodiments, the at least one analyte-responsive response element may comprise a tetracycline responsive element (TRE), and the at least one analyte-responsive transactivator may comprise a tetracycline-controlled transactivator. In some embodiments, the nucleic acids encoding each of luxA, luxB, luxC, luxD, luxE, and flavin reductase are operatively linked to the TRE.

In such embodiments, the tetracycline-controlled transactivator binds to the TRE, thereby activating the TRE. This activation initiates transcription of the nucleic acids operatively linked to the TRE, which ultimately results in production of the autobioluminescent signal. However, in the presence of tetracycline or one of its analogs, the tetracycline-controlled transactivator binds to the tetracycline or one of its analogs, rather than the TRE. As a result, when such embodiments are exposed to tetracycline or one of its analogs like doxycycline, there is reduced transcription of the nucleic acids encoding each of luxA, luxB, luxC, luxD, luxE, and flavin reductase, resulting in a reduced autobioluminescent signal.

Moreover, a kit for producing a stem cell having repressible autobioluminescence is likewise disclosed. The kit is used in reference to a combination of articles that facilitate a process, method, assay, analysis, or manipulation of a sample.

The kit comprises any vector(s) disclosed above in the methods for producing a stem cell comprising an autonomous luminescent phenotype, wherein the stem cell emits a repressible autobioluminescent signal. The kit may comprise any number of vectors (e.g., one, two, three, etc.) comprising any number of configurations of at least one of the nucleic acids encoding each of luxA, luxB, luxC, luxD, luxE, and flavin reductase.

In some embodiments, the kit may further comprise an amount of the analyte. The analyte may be any analyte that may bind to, and thereby activate, the at least one analyte-responsive transactivator, thereby resulting in a repressible autobioluminescent signal.

In some embodiments, the kit may comprise chemical reagents or enzymes required for the method, primers and probes, as well as any other components. For example, the kit may comprise necessary reagents and tools for transforming a stem cell with vector(s), such that the user may produce a stem cell that emits a repressible autobioluminescent signal in the presence of the analyte. The kit may also contain written instructions describing how to use the kit. For example, the instructions may pertain to methods of using the kit, including methods for transforming a stem cell with vector(s). Such instructions are advantageous in that they may increase the ease with which a user may use the kit.

4. Tissue-Specific Autobioluminescent Signal

Methods are disclosed for producing a stem cell comprising an autonomous luminescent phenotype, wherein the emitted autobioluminescent signal is tissue-specific. That is, the autobioluminescent signal is only emitted when the stem cell differentiates into a tissue cell. A tissue cell is a specialized (i.e., differentiated) cell that has tissue-specific structures that allow it to perform specialized functions, e.g., a muscle, nerve, or bone, cell. The tissue cell may comprise, for example, any myocyte, neuron, neuroglia, osteoclast, osteocyte, or osteoclast.

The method comprises transfecting the stem cell with at least one vector. The at least one vector comprises at least one of the nucleic acids encoding each of luxA, luxB, luxC, luxD, luxE, and flavin reductase, wherein the at least one of the nucleic acids is operatively linked to a tissue-specific promoter. The tissue-specific promoter controls gene expression in a tissue-dependent manner, i.e., it is only active in certain types of tissue cells. Thus, the at least one nucleic acid to which it is operatively linked is only expressed when the stem cell is differentiated into a type of tissue cell in which the tissue-specific promoter is active. That is, in such embodiments, there may be tissue-specific transcription of the at least one nucleic acids.

The method may comprise transfecting the stem cell with any number of vectors. For example, in some embodiments, the method may comprise transfecting the stem cell with a single vector comprising all of the nucleic acids encoding each of luxA, luxB, luxC, luxD, luxE, and flavin reductase operatively linked to the tissue-specific promoter. In such embodiments, once transfected with the single vector, the stem cell may produce an autobioluminescent signal when the stem cell is differentiated into a type of tissue cell in which the tissue-specific promoter is active.

In other embodiments, the method may comprise transfecting the stem cell with multiple vectors. For example, there may be six vectors, wherein each vector contains one of the nucleic acids encoding each of luxA, luxB, luxC, luxD, luxE, and flavin reductase (i.e., each of the foregoing is expressed from a unique vector). At least one of the nucleic acids may be linked to the tissue-specific promoter. Any nucleic acid not linked to a tissue-specific promoter may be linked to a constitutive promoter.

In still other embodiments, the method may comprise transfecting the stem cell with a first vector and a second vector. For example, in some embodiments, the first vector may comprise the nucleic acids encoding each of luxA and luxB operatively linked to a tissue specific promoter, such as the TNNT2 promoter, which is a cardiomyocyte-specific promoter. Thus, luxA and luxB are only expressed when the stem cell differentiates into a cardiomyocyte. Such a configuration may result in tissue-specific transcription of the luxA nucleic acid and the luxB nucleic acid, such that there is tissue-specific expression of the luciferase component necessary for autobioluminescence.

In said two vector embodiments, the second vector may comprise the nucleic acids encoding each of luxC, luxD, luxE, and flavin reductase operatively linked to a constitutive promoter. Thus, in said embodiments, there is a continuous expression of the nucleic acids encoding each of luxC, luxD, luxE, and flavin reductase, thereby resulting in continuous production of the luciferin component and the $FMNH_2$ co-substrate for the chemical reaction resulting in autobioluminescence.

By way of example, post-transfection, the stem cell may emit a tissue-specific autobioluminescent signal. Prior to differentiation of the stem cell, the TNNT2 promoter remains inactive, and nucleic acids encoding each of luxA and luxB are not expressed. However, if the stem cell is differentiated into a cardiomyocyte cell, the TNNT2 promoter will become active, thereby initiating transcription of the luxA nucleic acid and the luxB nucleic acid. As a result, luxA and luxB are produced.

Taking the two vector system as an illustrative example, there is a continuous expression of luxC, luxD, luxE, and flavin reductase because their expression is driven by a constitutive promoter. Thus, when the tissue-specific promoter is activated such that there are luxA and luxB, the stem cell may emit a tissue-specific autobioluminescent signal through the chemical reaction disclosed herein. In such embodiments, the tissue-specific bioluminescent signal is produced autonomously and in real-time.

However, when the tissue-specific promoter is inactive, only luxC, luxD, luxE, and flavin reductase are produced, which is insufficient to emit an autobioluminescent signal. As a result, emission of the autobioluminescent signal bioindicates the onset of differentiation into the type of tissue cell in which the tissue-specific promoter is expressed, i.e., the autobioluminescent signal is tissue-specific.

The two vector system disclosed herein is advantageous for generating a robust autobioluminescent signal, although not as robust as the six vector system. First, with respect to the lux cassette, it is believed that transcriptional activity is lower for nucleic acids positioned distal to a promoter. Thus, separating the lux nucleic acids onto two independent vectors, i.e., the first vector and the second vector, mitigates the issue, as it necessarily lessens the distance between some of the nucleic acids and the promoter as compared to positioning all of the nucleic acids onto a single vector. Second, the two vector system allows for varying the ratio of luxA and luxB nucleic acids relative to luxC, luxD, luxE, and flavin reductase nucleic acids. This strategy is advantageous as it was unexpectedly discovered that a ratio of approximately 20:1 to 30:1 of luxC, luxD, luxE, and flavin-reductase nucleic acids to luxA and luxB nucleic acids results in a robust autonomous luminescent phenotype (FIGS. 2A-2D). Experimental testing indicated that, across all tested cell types, this aforementioned ratio resulted in a strong luminescent signal. As detailed herein, such a discovery is surprising as an overexpression of the nucleic acids encoding each of luxC, luxD, luxE, and flavin-reductase relative to the nucleic acids encoding each of luxA and luxB would be expected to result in a reduced luminescent signal as well as damage to cellular growth and physiology. Nonetheless, this ratio results in an unexpectedly robust autobioluminescent signal.

As discussed earlier herein, an overexpression of luxC, luxD, luxE, and flavin-reductase relative to luxA and luxB is desirable for producing a robust autobioluminescent phenotype. Accordingly, in some embodiments, the methods may comprise transfecting the stem cell with an amount of the nucleic acids encoding luxC, luxD, luxE, and flavin reductase that is from ten to forty times greater than an amount of the nucleic acids encoding luxA and luxB. Preferably, the methods may comprise transfecting the stem cell with an amount of the nucleic acids encoding luxC, luxD, luxE, and flavin reductase that is from twenty to thirty times greater than an amount of the nucleic acids encoding luxA and luxB. For example, in the disclosed two vector system, the method may preferably comprise transfecting an amount of the second vector that is from twenty to thirty times of an amount of the first vector. Transfecting the nucleic acids in these amounts will achieve the aforementioned advantageous ratio, thereby resulting in a strong light output.

A kit for producing a stem cell comprising a tissue-specific autonomous luminescent phenotype is disclosed. The kit is used in reference to a combination of articles that facilitate a process, method, assay, analysis, or manipulation of a sample.

The kit comprises any vector disclosed above in the methods for producing a stem cell comprising an autonomous luminescent phenotype, wherein the stem cell emits a tissue-specific autobioluminescent signal. The kit may comprise any number of vectors (e.g., one, two, three, etc.) comprising any number of configurations of at least one of the nucleic acids encoding each of luxA, luxB, luxC, luxD, luxE, and flavin reductase. In such embodiments, once transfected with the vector(s), the stem cell may produce a tissue-specific autobioluminescent signal. In some embodiments, vector(s) expressing luxC, luxD, luxE, and flavin reductase may be present in the kit at an amount of from ten to forty times greater than an amount of vector(s) expressing luxA and luxB. More preferably, vector(s) expressing luxC, luxD, luxE, and flavin reductase may be present at an amount of from twenty to thirty times greater than an amount of vector(s) expressing luxA and luxB. As detailed herein, such a ratio is advantageous for producing a maximal luminescent signal. Therefore, a kit comprising said amounts of vector(s) would be particularly advantageous in that a user of the kit could develop a stem cell emitting a robust autobioluminescent signal.

In some embodiments, the kit may comprise chemical reagents or enzymes required for the method, primers and probes, as well as any other components. For example, the kit may comprise necessary reagents and tools for transforming a stem cell with vector(s) such that the user may produce a stem cell comprising a tissue-specific autonomous luminescent phenotype. The kit may also contain written instructions describing how to use the kit. For example, the instructions may pertain to methods of using the kit, including methods for transforming a stem cell with vector(s). Such instructions are advantageous in that they may increase the ease with which a user may use the kit.

VII. Methods for Producing a Specialized Cell Comprising an Autonomous Luminescent Phenotype Methods are disclosed for producing a stem cell-derived autonomously bioluminescent cell from an autonomously bioluminescent stem cell.

The method may comprise producing a stem cell comprising an autobioluminescent phenotype by any method disclosed herein. The method may comprise differentiating the stem cell comprising an autobioluminescent phenotype into the stem cell-derived autonomously bioluminescent cell, which may be any desired functional specialized cell. That is, the stem cell-derived autonomously bioluminescent cell may comprise, for example, a nerve, muscle, or bone cell.

Differentiation refers to a developmental process whereby cells become specialized for a particular function, for example, where cells acquire one or more morphological characteristics and/or functions differently from that of the initial cell type. Differentiation includes both lineage commitment and terminal differentiation processes. States of undifferentiation or differentiation may be assessed, for example, by monitoring the presence or absence of lineage markers, using FACS analysis, immunohistochemistry or other procedures known to a worker skilled in the art. Moreover, differentiation may be performed by any suitable process, including, for example, small molecule method, signal inhibition, the addition of growth factors, co-culture environments, or other procedures known to a worker skilled in the art.

Moreover, the stem cell-derived autonomously bioluminescent cell may inherit the characteristics of any embodiment of a stem cell comprising an autonomous bioluminescent phenotype from which the stem cell-derived autonomously bioluminescent cell is derived. That is, the stem cell-derived autonomously luminescent cell inherits the capability of producing luxA, luxB, luxC, luxD, luxE, and flavin reductase such that the stem cell-derived autonomously luminescent cell self-synthesizes all of the substrates for bioluminescent signal production.

When the stem cell-derived autonomously luminescent cell is derived from a stem cell comprising an autobioluminescent phenotype, wherein the stem cell produces luxC, luxD, luxE, and flavin reductase at a greater combined production level than a combined production level of luxA and luxB, the stem cell-derived autonomously luminescent cell may likewise produce a greater combined production level of luxC, luxD, luxE, and flavin reductase than a combined production level of luxA and luxB. In such embodiments, the stem cell-derived autonomously luminescent cell may, for example, comprise a combined production level of luxC, luxD, luxE, and flavin reductase that ranges from ten to forty times greater than a combined production level of luxA and luxB. Preferably, the combined production level of luxC, luxD, luxE, and flavin reductase range is from twenty to thirty times greater than the combined production level of luxA and luxB. Such a ratio would result in a robust bioluminescent signal.

A stem cell-derived autonomously bioluminescent cell is advantageous in that may enable substrate-free autobioluminescent imaging of specialized, or differentiating/differentiated, cells under in vitro and/or in vivo conditions in, for example, a high-throughput manner. Given the ability of the stem cell-derived autonomously bioluminescent cell to produce bioluminescence without the need for an investigator to add an exogenous substrate, the cell has applications in, for example, real-time, non-invasive, continuous, and substrate-free tracking, identifying, and/or measuring the cells' viability, migration, and/or fate.

VIII. Methods for Using a Stem Cell Comprising an Autonomous Bioluminescent Phenotype Disclosed herein are methods for using a stem cell comprising an autonomous bioluminescent phenotype according to any of the embodiments disclosed herein. For all of the methods of use disclosed herein, due to the autonomous nature of the bioluminescent signal, the methods may comprise assaying or interrogating the stem cells repeatedly or continuously without destruction. Advantageously, this may reduce the cells that must be prepared for each method and may reduce sample-to-sample variability.

The methods disclosed herein are likewise highly scalable, with visualization possible in all plate formats. For all of the methods of using a stem cell comprising an autobioluminescent phenotype disclosed herein, the methods may comprise seeding the stem cell into at least one well of a multi-well plate, ranging from, for example, a 6-well to 1536-well, that is, a 6-well plate, a 12-well plate, a 24-well plate, a 96-well plate, etc. Such scalability is highly advantageous in that it permits an investigator to be able to apply each method in a low or high throughput manner.

1. Constitutive Autobioluminescent Signal

Disclosed herein are methods for using a stem cell comprising an autonomous luminescent phenotype, wherein the stem cell emits a constitutive autobioluminescent signal. Each of said methods may comprise producing at least one stem cell comprising an autonomous bioluminescent phenotype, wherein the stem cell emits a constitutive luminescent signal. The at least one stem cell emitting a constitutive bioluminescent signal may be produced according to any of the methods disclosed herein for producing such a stem cell. Accordingly, the at least one stem cell will constitutively produce luxA, luxB, luxC, luxD, luxE, and flavin reductase, such that the at least one stem cell autonomously emits a constitutive bioluminescent signal.

i. Measuring Cell Population Size and Viability

A method of real-time monitoring of cell population size is disclosed. The method may comprise detecting, measuring, and/or quantifying the constitutive autobioluminescent signal emitted from the at least one stem cell by a photo counter-imaging device, a charge-coupled device camera-based equipment, a scintillation counter, a luminometer, a plate reader, or photographic film. Such devices include, for example, a CCD-based IVIS Lumina imaging system (PerkinElmer) or a PMT-based Synergy2 plate reader (BioTek). The detection, measurement, and/or quantification may occur at one or more time points.

The method may comprise assessing cell population size based on the detection, measurement, and/or quantification of the constitutive bioluminescent signal. Advantageously, the measurement of the constitutive luminescent signal emitted by a population of at least one stem cells comprising an autonomous bioluminescent phenotype strongly correlates to the total number of the at least one stem cells ($R^2$=0.93) (see FIG. 9B and discussion in Working Example 2). Thus, this correlation may allow for an accurate assessment of cell population size.

In some embodiments, the method comprises measuring the cell population size over two or more points in time. As the constitutive bioluminescent signal is fully self-generated and self-directed by the at least one stem cell, measuring the cell population size over two or more points in time may produce an accurate longitudinal representation of proliferation or death of the at least one stem cell.

In some embodiments, the method may comprise real-time monitoring and/or assessing cell viability of the at least one stem cell based on the detection, measurement, and/or quantification of the constitutive bioluminescent signal. Advantageously, it is believed that the lux cassette is directly linked to endogenous cell metabolism. Accordingly, this method may beneficially enable kinetic monitoring of the viability of the at least one stem cell.

In some embodiments, the method comprises measuring the cell viability over two or more points in time. As the constitutive luminescent signal is fully self-generated and self-directed by the at least one stem cell in real-time, measuring the cell viability over time may beneficially produce an accurate longitudinal representation of proliferation or death of the at least one stem cell.

Advantageously, these methods for measuring cell population size and viability are the first methods for using continuous, exogenous substrate independent, self-generated bioluminescent signal in stem cells to report cell population size and viability.

ii. Measuring an Effect of an Agent

A method for measuring an effect of an agent on at least one stem cell is disclosed. The method comprises contacting the at least one stem cell with an agent. In some embodiments, the agent may be a compound with known toxicity. For example, in said embodiments, the agent may comprise a chemotherapeutic agent, an antibiotic, an insecticide, a pesticide, an herbicide, a fertilizer, or any other compound. In other embodiments, the agent may be a compound with a known therapeutic effect. The at least one stem cell may be contacted with the agent by any suitable mechanism. For example, the at least one stem cell may be exposed to the agent in a dish, a flask, or a culture plate.

The method may comprise detecting, measuring, and/or quantifying the constitutive bioluminescent signal emitted from the at least one stem cell after the at least one stem cell is contacted with the agent by any device disclosed herein for detecting, measuring, and/or quantifying the bioluminescent signal. The detection, measurement, and/or quantification may occur at one or more time points.

Figure 10:
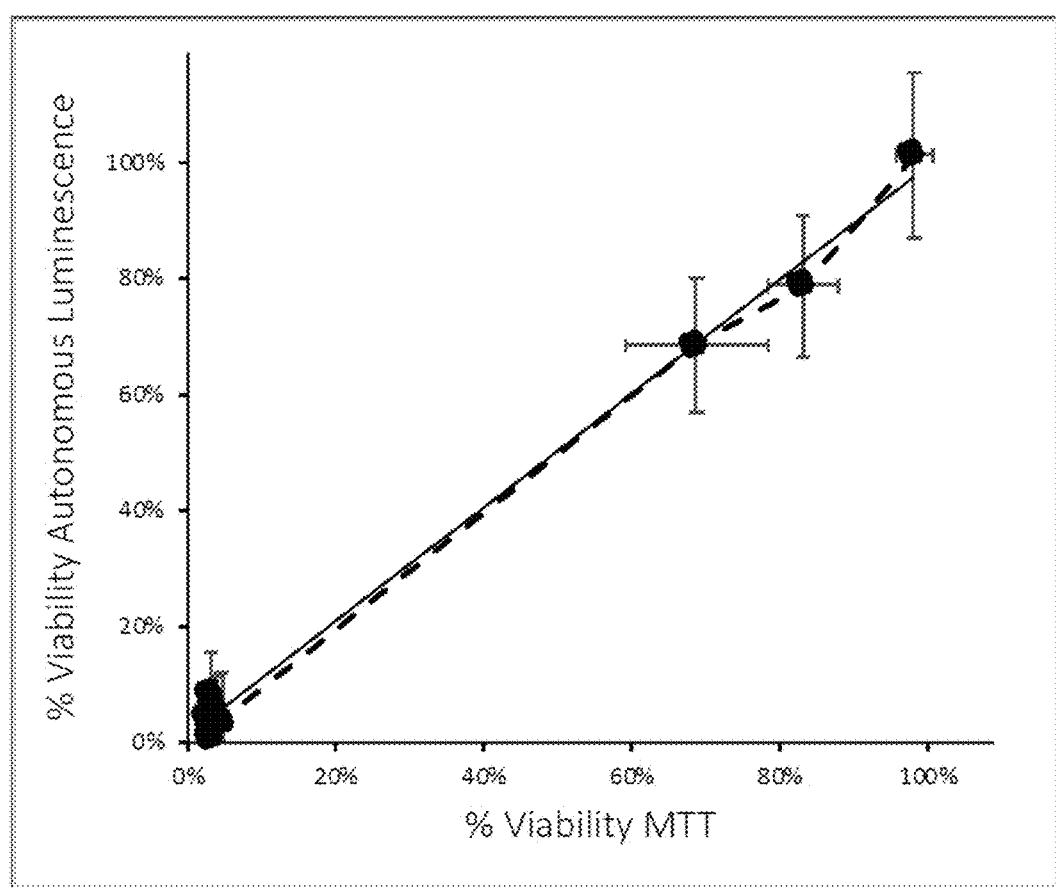
FIG. 10. Treatment of the iPSC-luxAB/CDEF line with a range of doxorubicin concentrations resulted in dose dependent changes to cell viability. Viability measurements made using the autonomous luminescent signal output indicative of changing cellular viabilities correlated strongly with the same measurements made using changes in MTT absorbance (570 nm) ($R^2$=0.99).

In some embodiments, the method may comprise assessing the cell viability of the at least one stem cell based on the detection, measurement, and/or quantification of the constitutive bioluminescent signal. Advantageously, a stem cell comprising an autonomous bioluminescent phenotype is also capable of reporting changes in cellular viability resulting from contact with an agent as the autonomous bioluminescent signal changes in response to negative or positive cell health. Specifically, the constitutive bioluminescent signal emitted from the at least one stem cell strongly correlates to the cell viability of the at least one stem cell (FIG. 10). Consequently, the post-contact measurement of the constitutive bioluminescent signal emitted from the at least one stem cell may be used to accurately assess the cell viability of the at least one stem cell.

In some embodiments, the method may comprise producing a control population comprising at least one control stem cell comprising an autonomous bioluminescent phenotype, wherein the stem cell emits a constitutive luminescent signal. The control population is not contacted with the agent, but is otherwise treated similarly, or substantially similarly, to the at least one stem cell that is contacted with the agent.

In said embodiments, the method may comprise comparing the measurement of the constitutive bioluminescent signal emitted from the at least one stem cell to a constitutive bioluminescent signal emitted from the control population. The control population may increase the ease and accuracy of determining a negative or a positive change in cell viability.

For example, in such embodiments, the method may comprise determining that a decrease in the measured constitutive bioluminescent signal emitted from the at least one stem cell relative to the constitutive bioluminescent signal emitted from the control population is indicative of a negative change in the cell viability of the at least one stem cell resulting from contact with the agent. In said embodiments, the method may comprise determining that the effect of the agent is cytotoxic. The method may comprise determining that the agent is fatal to the at least one stem cell when the at least one stem cell ceases production of the constitutive bioluminescent signal. Advantageously, this method allows for a valuable assessment of the cytotoxic effect of the agent.

In other embodiments, the method may comprise determining that an increase in the measured constitutive bioluminescent signal emitted from the at least one stem cell relative to the constitutive bioluminescent signal emitted from the control population is indicative of a positive change in the cell viability of the at least one stem cell resulting from contact with the agent. In said embodiments, the method may comprise determining that the effect of the agent is therapeutic. Thus, this method results in a valuable assessment of the beneficial effect of the agent on the at least one stem cell.

In some embodiments, the method may comprise subjecting the at least one stem cell to a range of concentrations of the agent. This is advantageous in that a range of concentrations may allow for an assessment of dose dependent changes in the at least one stem cell. A charting of the dose dependent changes is valuable in that it is a necessary part of understanding the relationship between agent exposure and cell viability. For example, when the agent is cytotoxic, the dose dependent changes may elucidate the agent's toxicity (e.g., determining $EC_{50}$, $IC_{50}$, $LD_{50}$, $LC_{50}$, and other similar measures of cytotoxicity).

In some embodiments, the method may comprise assessing the effect of the agent in real time. Advantageously, as there is no delay for the synthesis, excretion, and extracellular collection of a reporter protein, direct evidence of the agent's effect may be assessed in real time.

In some embodiments, the method may comprise assessing the effect of the agent over two or more points in time. Advantageously, the at least one stem cell may be immediately interrogated after contacting it with the agent to determine the agent's effect across any timescale from minutes to days. Further, because the stem cell autonomously bioluminesces and said bioluminescence correlates with cell viability, the effect of an agent may be continuously monitored based on the cell viability, which provides valuable information regarding the onset of the effect of the agent as well as the duration of said effects. Greater knowledge of the agent's effect, such as when the effect stabilizes, may enable a more confident assessment of the toxicity and/or therapeutic capability of the agent.

In some embodiments, the method may comprise assessing an agent for drug discovery based on assessing the effect of the agent. Assessing the cytotoxic and/or therapeutic effect of an agent is particularly valuable for drug discovery. Said assessment may advantageously contribute to ranking agents for consideration in drug discovery and to predict their fate after administration into the human body.

The methods disclosed herein for measuring the effect of an agent in at least one stem cell comprising an autonomous bioluminescent phenotype lead to a better contextual understanding of the toxic and/or therapeutic effects of an agent. These methods of measuring an agent's effect may beneficially provide a means of assessing an agent's cytotoxic and/or therapeutic effect in, for example, a real time, high-throughput assay.

iii. In Vivo Imaging

A method of reagent-free in vivo imaging of at least one stem cell is disclosed. The method includes injecting the at least one stem cell into an organism. An organism includes, but is not limited to, a human or a non-human animal, such as a non-human primate, a cow, a horse, a sheep, a goat, a pig, a dog, a cat, a rabbit, a mouse, a rat, a gerbil, a frog, a toad, an insect, a fruit fly (e.g., *Drosophila melanogaster*), a fish (e.g., *Danio rerio*), a roundworm (e.g., *Caenorhabditis elegans*), and any transgenic species thereof. The term "organism" covers every stage of life of an organism (e.g., from prenatal development to advanced adulthood, including every stage in between). For example, the term includes but is not limited to an embryo (including zygote, blastocyte, etc.), a fetus, a neonate, an infant, an adolescent, and an adult. The terms may specify male or female or both, or exclude male or female.

The at least one stem cell may be injected into the organism in any manner, e.g., intraperitoneally, intravenously, intradermally, or subcutaneously, into the organism. After injection of the at least one stem cell, the method comprises imaging the constitutive bioluminescent signal emitted from the at least one stem cell in the organism. The constitutive bioluminescent signal may be imaged by any suitable device disclosed herein for detecting, measuring, and/or quantifying the bioluminescent signal. The detection, measurement, and/or quantification may occur at one or more time points.

Figure 12A:
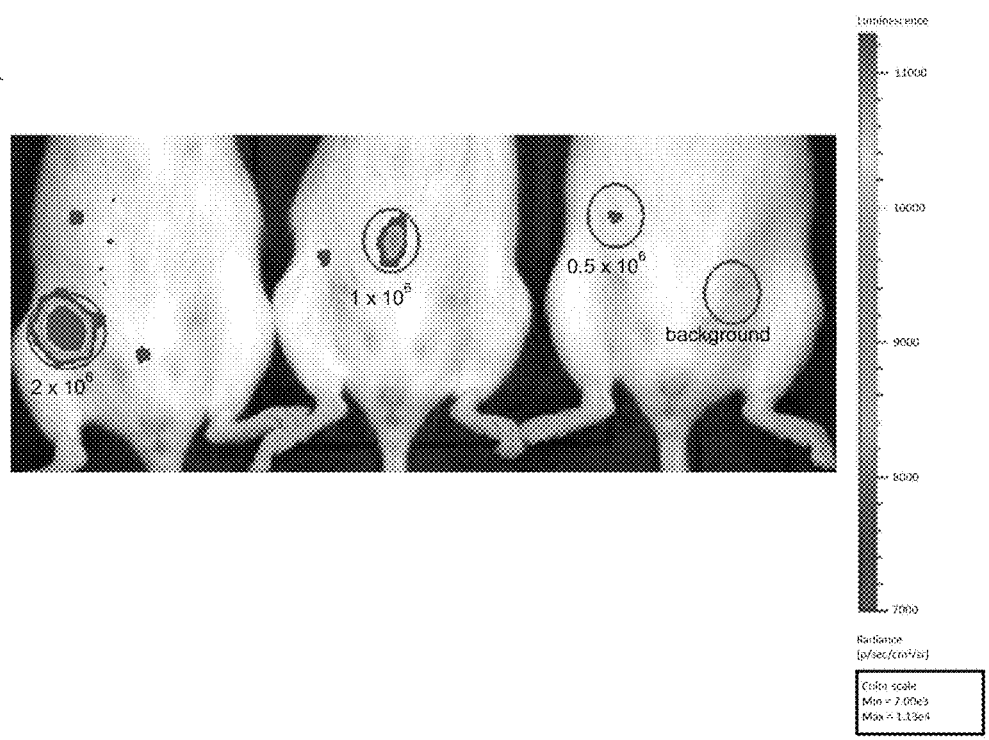
FIGS. 12A-12B. In vivo imaging of autobioluminescent human adipose derived mesenchymal stem cells (hADMSCs).
Figure 12B:
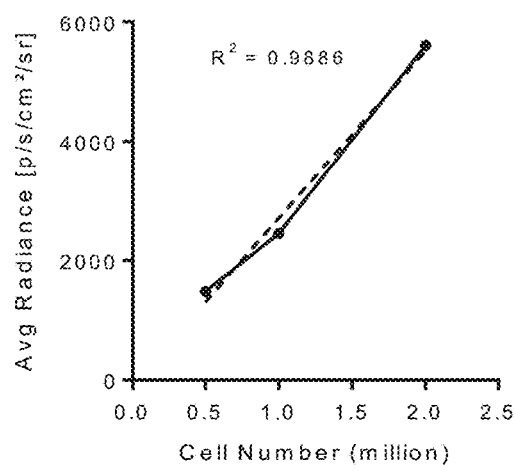

In some embodiments, the method may comprise measuring the constitutive bioluminescent signal and determining a total number of the at least one stem cell present in vivo. Advantageously, the emitted constitutive luminescent signal strongly correlates with injected cell number (FIG. 12B). Accordingly, this correlation may be employed in accurately determining a total number of the at least one stem cell present in vivo. This method may beneficially reveal the proliferation or death of the at least one stem cell in vivo.

The method may comprise tracking movement of the at least one stem cell within the organism. In such embodiment, the method may comprise imaging the organism for at least one location of the autonomous bioluminescent signal emitted from the at least one stem cell, thereby determining migration of the at least one stem cell relative to site of injection. As the at least one stem cell may establish in more than one location within the organism, it may be beneficial to image the organism for more than one location of the autonomous bioluminescent signal in order to determine all the locations to which the at least one stem cell migrated.

Advantageously, this method allows for reagent-free in vivo imaging in an organism. Such a method improves organism welfare and obviates concerns over stress responses and injection site inflammation by allowing for data acquisition without repetitive needle sticks. The method may allow for non-invasive optical imaging to occur continuously over the lifetime of the organism. The method, therefore, offers a significant advantage over current bioluminescent imaging technologies that are only able to capture intermittent snapshots of in vivo stem cell activity. Indeed, no other present method is currently capable of substrate-free, continuous imaging in vivo. Ultimately, this method may offer such advantages as non-invasive guiding and verification of cell injection, tracking of cell migration, and monitoring of long-term integration and survival of grafted stem cells.

2. Inducible or Repressible Autobioluminescent Signal

Disclosed herein are methods for using a stem cell emitting an inducible or repressible autobioluminescent signal when exposed to an analyte.

In each of said methods, the method may comprise producing at least one stem cell comprising an autonomous luminescent phenotype, wherein the stem cell emits an inducible or repressible autobioluminescent signal when exposed to an analyte. In some embodiments, the at least one stem cell emits an inducible autobioluminescent signal when exposed to an analyte. The at least one stem cell emitting an inducible autobioluminescent signal when exposed to an analyte may be produced according to any of the methods disclosed herein for producing such a stem cell. In said embodiments, when exposed to the analyte, the at least one stem cell may produce luxA, luxB, luxC, luxD, luxE, and flavin reductase, such that the at least one stem cell emits an autobioluminescent signal. Thus, in such embodiments, exposure to the analyte may directly induce gene expression.

In other embodiments, the stem cell emits a repressible autobioluminescent signal when exposed to an analyte. The at least one stem cell emitting a repressible autobioluminescent signal when exposed to an analyte may be produced according to any of the methods disclosed herein for producing such a stem cell. In said embodiments, when exposed to the analyte, the at least one stem cell may reduce expression of the nucleic acids encoding each of luxA, luxB, luxC, luxD, luxE, and flavin reductase, such that the at least one stem cell emits a repressible autobioluminescent signal. Thus, in such embodiments, exposure to the analyte may directly repress gene expression.

i. Monitoring Gene Expression

Specifically, disclosed is a method for real-time monitoring of gene expression in at least one stem cell. The method comprises producing at least one stem cell comprising an autonomous bioluminescent phenotype, wherein the stem cell emits an inducible or repressible autobioluminescent signal when exposed to an analyte.

The method may comprise contacting the at least one stem cell with an analyte. The analyte may be any suitable analyte that induces the stem cell to emit or repress the autobioluminescent signal. That is, selection of the analyte may be driven by the composition of the at least one stem cell. For example, if the at least one stem cell emits the autobioluminescent signal in the presence of tetracycline or one of its analogs, then the analyte may be tetracycline or one of its analogs.

The at least one stem cell may be contacted with the analyte by any suitable mechanism. For example, the at least one stem cell may be present in a dish, a flask, or a culture plate. The at least one stem cell may be contacted with the analyte while in the dish, the flask, or culture plate.

The method may comprise detecting, measuring, and/or quantifying the autobioluminescent signal emitted from the at least one stem cell after the at least one stem cell is contacted with the analyte by any device disclosed herein for detecting, measuring, and/or quantifying the bioluminescent signal. The detection, measurement, and/or quantification may occur at one or more time points.

In some embodiments, the method may comprise producing a control population comprising at least one control stem cell comprising an autonomous bioluminescent phenotype, wherein the stem cell emits an inducible or repressible luminescent signal. The control population is not contacted with the agent, but is otherwise treated similarly, or substantially similarly, to the at least one stem cell that is contacted with the agent.

The method may comprise comparing the measurement of the autobioluminescent signal emitted from the at least one stem cell to an autobioluminescent signal emitted from a control population. In embodiments wherein the at least one stem cell emits an inducible autobioluminescent signal, an increase in the measured autobioluminescent signal emitted from the at least one stem cell relative to the autobioluminescent signal emitted from the control population is indicative of exposure to the analyte. In some embodiments, the method may further include determining an activation of transcription of the nucleic acids encoding each of luxA, luxB, luxC, luxD, luxE, and flavin reductase in response to the analyte when the measured autobioluminescent signal is greater than the autobioluminescent signal emitted from the control population.

In other embodiments, wherein the at least one stem cell emits a repressible autobioluminescent signal, a reduction in the measured autobioluminescent signal emitted from the at least one stem cell relative to the autobioluminescent signal emitted from the control population is indicative of exposure to the analyte. In some embodiments, the method may further include determining a repression of luxA, luxB, luxC, luxD, luxE, and flavin reductase in response to the analyte when the measured autobioluminescent signal is less than the autobioluminescent signal emitted from the control population. The control population is advantageous in that it may increase the ease and accuracy of determining a change in the autobioluminescent signal as a result of contact with the analyte.

In some embodiments, the method further comprises subjecting the at least one stem cell to a range of concentrations of the analyte. This is advantageous in that a range of concentrations may allow for an assessment of dose dependent changes in the at least one stem cell. A charting of dose dependent changes is valuable in that it is a necessary part of understanding the relationship between analyte exposure and gene expression.

The method may comprise assessing the impact of the analyte on gene expression over two or more points in time. Advantageously, there is no, or very little, delay for the synthesis, excretion, and extracellular collection of a reporter protein, thereby allowing the method to provide direct evidence of the impact of the analyte on gene expression in real-time. The stem cell may be contacted with the analyte and then immediately interrogated to determine the effect of the analyte across any timescale from minutes to days. Because the stem cell autonomously luminesces, impact of the analyte may be continuously monitored, which provides valuable information regarding the onset of gene expression or repression as well as the duration of said effects.

ii. Determining Presence of an Analyte

A method of determining a presence of an analyte in a sample is disclosed. The method comprises producing at least one stem cell comprising an autonomous bioluminescent phenotype, wherein the stem cell emits an inducible or repressible autobioluminescent signal when exposed to an analyte.

The method may comprise contacting the at least one stem cell with a sample. The at least one stem cell may be contacted with the sample by any suitable mechanism. For example, the at least one stem cell may be present in a container, such as a dish, a flask, or a culture plate. The at least one stem cell may be contacted with the sample while in the container. The sample may, or may not, contain a concentration of the analyte. The analyte may comprise any compound or functional group that causes an induction or repression of the autobioluminescent signal of the at least one stem cell that emits an inducible or repressible signal, respectively.

The method may comprise detecting, measuring, and/or quantifying the autobioluminescent signal emitted from the at least one stem cell after the at least one stem cell is contacted with the sample by any device disclosed herein for detecting, measuring, and/or quantifying the bioluminescent signal. The detection, measurement, and/or quantification may occur at one or more time points.

In some embodiments, the method may comprise producing a control population comprising at least one control stem cell comprising an autonomous bioluminescent phenotype, wherein the stem cell emits an inducible or repressible luminescent signal. The control population is not contacted with the sample, but is otherwise treated similarly, or substantially similarly, to the at least one stem cell that is contacted with the sample.

In such embodiments, the method may comprise comparing the measurement of the autobioluminescent signal emitted from the at least one stem cell to an autobioluminescent signal emitted from a control population. In embodiments wherein the at least one stem cell emits an inducible autobioluminescent signal, an increase in the measured autobioluminescent signal emitted from the at least one stem cell relative to the autobioluminescent signal emitted from the control population is indicative of contact with the analyte. In some embodiments, the method may comprise determining the presence of the analyte in the sample when the measured autobioluminescent signal is greater than the autobioluminescent signal emitted from the control population.

In yet another embodiment, wherein the at least one stem cell emits a repressible autobioluminescent signal, a reduction in the measured autobioluminescent signal emitted from the at least one stem cell relative to the autobioluminescent signal emitted from the control population is indicative of contact with the analyte. In some embodiments, the method may comprise determining the presence of the analyte in the sample when the measured autobioluminescent signal is less than the autobioluminescent signal emitted from the control population. The presence of the control population is advantageous in that it may increase the ease and accuracy of determining a change in the autobioluminescent signal as a result of contact, or lack of contact, with the analyte.

The method may be a valuable tool in rapidly screening numerous samples for the presence of an analyte. Advantageously, there is no delay for the synthesis, excretion, and extracellular collection of a reporter protein; thus, there is direct evidence of the impact of the sample on the at least one stem cell in real-time. The effect of the sample on the at least one stem cell may be observed across any timescale from minutes to days.

3. Tissue-Specific Autobioluminescent Signal

Figure 18:
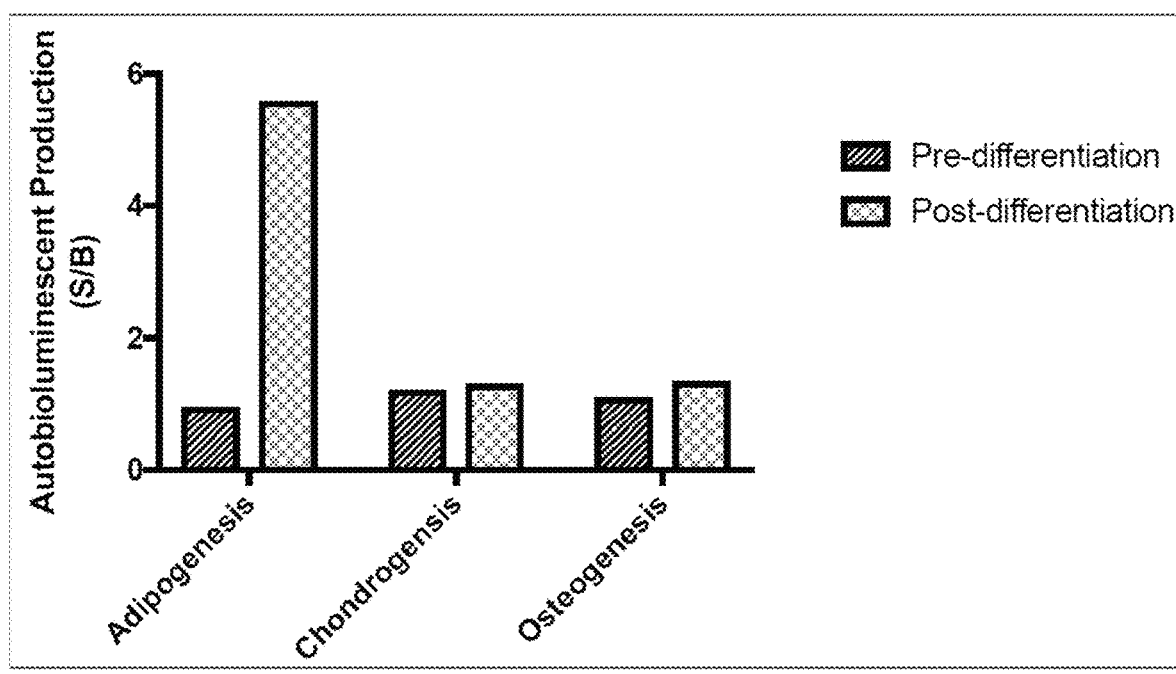
FIG. 18. Human mesenchymal stem cells (MSCs) bearing the luxCDABEF operon under the control of the adipose-tissue-specific human AP2 promoter were assayed for autobioluminescent production relative to background light detection (S/B) before differentiation and following differentiation into adipocytes (adipogenesis), chondrocytes (chondrogenesis), or osteocytes (osteogenesis). The tissue-specific promoter initiated autobioluminescent production without external stimulation only upon differentiation into the adipose tissue type. No significant autobioluminescent signal was detected following differentiation into non-target lineages, suggesting that differentiation reporting was highly specific.

A method of real-time differentiation reporting using at least one stem cell comprising a tissue-specific autonomous luminescent phenotype is disclosed. That is, lux expression may be tied to a tissue-specific promoter such that emission of an autobioluminescent signal may coincide with expression of a tissue-specific promoter (FIG. 18).

The method comprises providing at least one stem cell comprising a tissue-specific autonomous luminescent phenotype. The at least one stem cell may comprise any embodiment disclosed herein wherein the autobioluminescent signal is tissue-specific, i.e., any embodiment wherein the autobioluminescent signal is only emitted when the at least one stem cell differentiates into at least one tissue cell. If the at least one stem cell differentiates into at least one tissue cell in which the tissue-specific promoter is expressed, the at least one tissue-specific cell emits an autonomous bioluminescent signal.

The method may comprise detecting, measuring, and/or quantifying the autobioluminescent signal emitted from the at least one stem cell and/or the at least one tissue cell by any device disclosed herein for detecting, measuring, and/or quantifying the bioluminescent signal. The detection, measurement, and/or quantification may occur at one or more time points.

In some embodiments, the method may comprise tracking the differentiation of the at least one stem cell to the at least one tissue cell over two or more points in time. Advantageously, the emission of the autobioluminescent signal may coincide with onset of differentiation of the at least one stem cell to the at least one tissue cell. Thus, this method provides direct information regarding a differentiation status of the at least one stem cell.

In some embodiments, the method may comprise detecting, measuring, and/or quantifying the autobioluminescent signal from the at least one stem cell and/or the at least one tissue cell at two or more time points. Advantageously, as the bioluminescent signal is fully self-generated and self-directed by the at least one tissue cell, detecting, measuring, and/or quantifying the bioluminescent signal at two or more time points may produce an accurate longitudinal representation of the differentiation of the at least one stem cell to the at least one tissue cell. The method may provide direct information regarding the time point at which the at least one stem cell differentiates into the at least one tissue cell.

The method may comprise assessing cell population size of the at least one tissue cell based on the detection, measurement, and/or quantification of the autobioluminescent signal. Advantageously, the measurement and/or quantification of the tissue-specific bioluminescent signal emitted from the at least one tissue cell correlates with a total number of the at least one tissue cell (FIG. 18 and Working Example 7). Thus, a cell population size of the at least one tissue cell may be assessed using this correlation. Such an assessment may provide information regarding a proportion of a population of the at least one stem cell that has differentiated into the at least one tissue-specific cell.

This method represents the first method of using autobioluminescence to track stem cell differentiation in real-time.

IX. Methods for Using a Specialized Cell Comprising an Autonomous Bioluminescent Phenotype Methods are disclosed herein for using stem cell-derived autonomously bioluminescent cell(s). Each of said methods may comprise producing at least one stem cell-derived autonomously bioluminescent cell that emits a constitutive bioluminescent signal. The at least one stem cell-derived autonomously bioluminescent cell may be produced according to any of the methods disclosed herein for producing such a cell. Accordingly, the at least one stem cell-derived autonomously bioluminescent cell may constitutively express luxA, luxB, luxC, luxD, luxE, and flavin reductase, such that said cell autonomously emits a constitutive bioluminescent signal.

1. Measuring Cell Population Size and Viability

A method of real-time monitoring of cell population size of a population of at least one stem cell-derived autonomously bioluminescent cell is provided. The method may comprise detecting, measuring, and/or quantifying the autobioluminescent signal emitted from the at least one stem cell-derived autonomously luminescent cell by any device disclosed herein for detecting, measuring, and/or quantifying the bioluminescent signal. The detection, measurement, and/or quantification may occur at one or more time points.

Figure 9A:
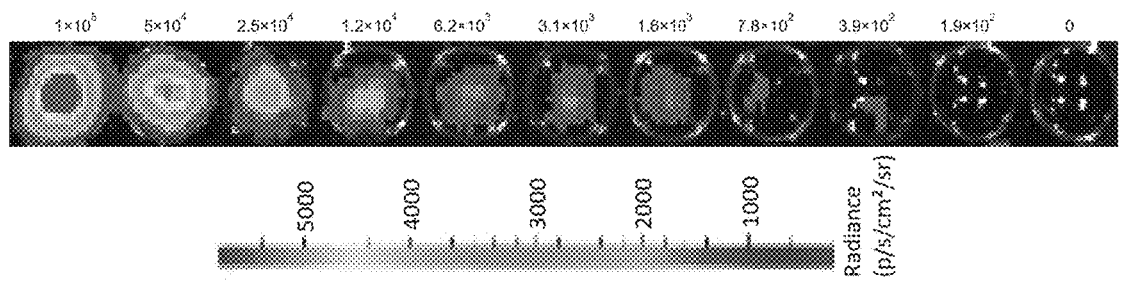
FIGS. 9A-9C. Constitutive autobioluminescence emitted from human induced pluripotent stem cells (iPSCs), according to an embodiment of the disclosure, expressing the integrated CBA-luxAB and CBA-luxCDEF split operon correlated strongly with cell number and MTT assay. FIG.
Figure 9B:
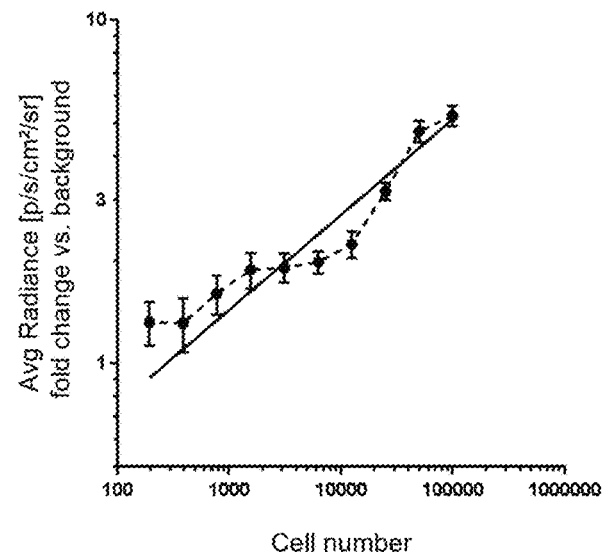

The method may comprise assessing cell population size based on the measurement of the autobioluminescent signal. Advantageously, the autobioluminescent signal emitted by a population of stem cells comprising an autobioluminescent phenotype, wherein the autonomous luminescent phenotype comprises emitting a constitutive luminescent signal, strongly correlates to the size of the population ($R^2=0.93$), as seen in FIG. 9B. Moreover, when said stem cells are differentiated into specialized cells, the specialized cells preserve the autobioluminescent phenotype. Indeed, the specialized cells produce approximately similar levels of autobioluminescent light (FIG. 19B) as stem cells comprising an autonomous bioluminescent phenotype, suggesting that the autobioluminescent phenotype is not radically altered by the change in cell type. Thus, it is believed that the average bioluminescent signal emitted by a population of stem cell-derived autonomously bioluminescent cells likewise strongly correlates to the size of the population. Therefore, the cell population size of the at least one stem cell-derived autonomously bioluminescent cell may be quickly and easily assessed using said correlation.

In some embodiments, the method may comprise detecting, measuring, and/or quantifying the cell population size over two or more points in time. The detection, measurement, and/or quantification may be taken two or more time points. Advantageously, as the autobioluminescent signal is fully self-generated and self-directed by the at least one stem cell-derived autonomously bioluminescent cell, measuring the cell population size over time may produce an accurate longitudinal representation of proliferation or death of the at least one stem cell-derived autonomously luminescent cell.

In some embodiments, the method comprises real-time monitoring of cell viability of the at least one stem cell-derived autonomously bioluminescent cell based on the detection, measurement, and/or quantification of the autobioluminescent signal. Advantageously, expression of the lux cassette is directly linked to endogenous cell metabolism. Accordingly, the ability of the at least one stem cell-derived autonomously luminescent cell to emit a constitutive bioluminescent signal enables kinetic monitoring of the at least one stem cell-derived autonomously bioluminescent cell's viability in addition to cell population size.

In some embodiments, the method may comprise measuring the cell viability over two or more points in time. The measurement may be taken at two or more time points. Advantageously, as the autobioluminescent signal is fully self-generated and self-directed by the at least one stem cell-derived autonomously luminescent cell in real-time, measuring the cell viability over time may produce an accurate longitudinal representation of proliferation or death of the at least one stem cell-derived autonomously luminescent cell.

The disclosed methods of measuring cell population and viability are the first methods for using a continuous, exogenous substrate independent, self-generated bioluminescent signal in a stem cell-derived autonomously bioluminescent cell to report cell population size and viability.

2. Measuring an Effect of an Agent

A method for measuring an effect of an agent using at least one stem cell-derived autonomously bioluminescent cell is disclosed. The method may comprise contacting the at least one stem cell-derived autonomously bioluminescent cell with an agent. In some embodiments, the agent may be a compound with known toxicity. For example, in said embodiments, the agent may comprise a chemotherapeutic agent, an antibiotic, an insecticide, a pesticide, an herbicide, a fertilizer, or any other compound. In other embodiments, the agent may be a compound with a known therapeutic effect. The at least one stem cell-derived autonomously bioluminescent cell may be contacted with the agent by any suitable mechanism. For example, the at least one stem cell-derived autonomously bioluminescent cell may be exposed to the agent in a dish, a flask, or a culture plate.

In some embodiments, the method comprises detecting, measuring, and/or quantifying the autobioluminescent signal emitted from the at least one stem cell-derived autonomously luminescent cell after contact with the agent by any device disclosed herein for detecting, measuring, and/or quantifying the bioluminescent signal. The detection, measurement, and/or quantification may occur at one or more time points.

Figure 19A:
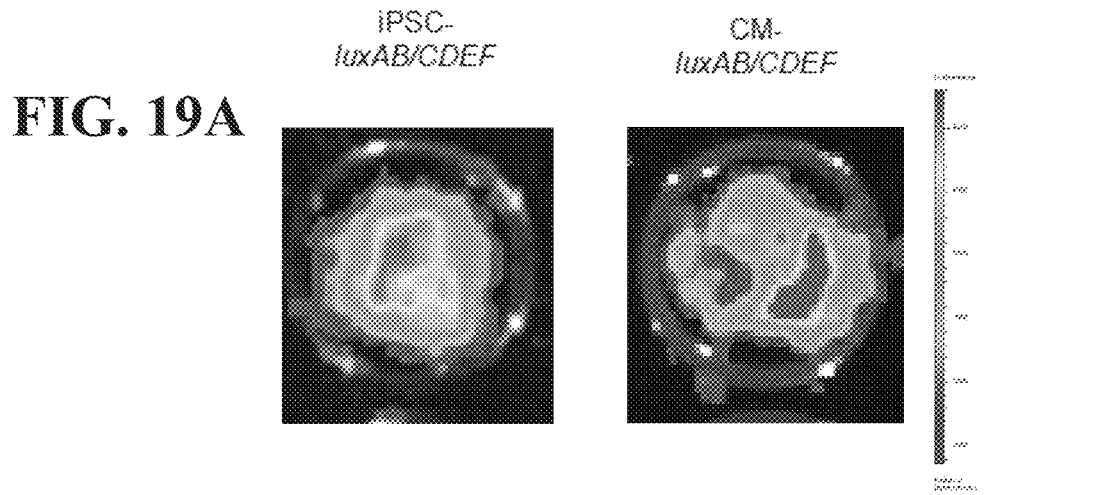
FIGS. 19A-19C. Human induced pluripotent stem cells (iPSCs) bearing the luxAB/CDEF operon maintain the autobioluminescent phenotype when differentiated into cardiomyocytes, according to an embodiment of the disclosure.
Figure 19B:
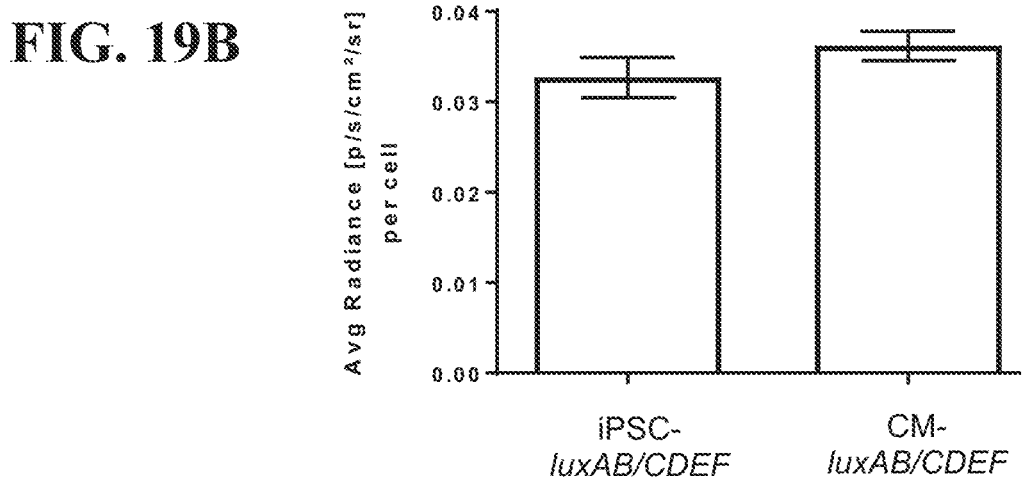
Figure 19C:
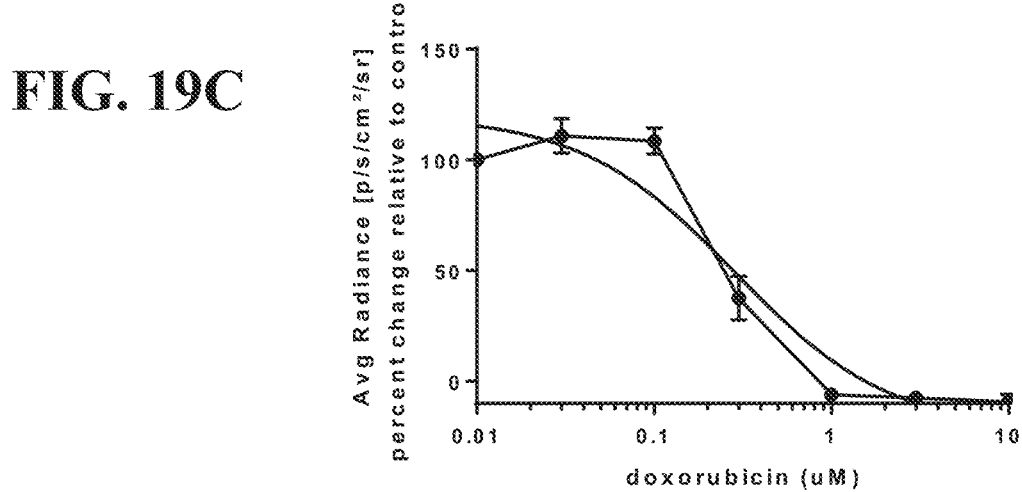

In some embodiments, the method may comprise assessing the cell viability of the at least one stem cell-derived autonomously luminescent cell based on the detection, measurement, and/or quantification of the autobioluminescent signal. Advantageously, a stem cell-derived autonomously bioluminescent cell is capable of reporting changes in cellular viability resulting from contact with an agent as the autonomous bioluminescent signal changes in response to positive and/or negative cell health. Specifically, the constitutive bioluminescent signal emitted from the at least one stem cell strongly correlates to the cell viability of the at least one stem cell (FIG. 19C). Consequently, the post-contact measurement of the autobioluminescent signal emitted from the at least one stem cell-derived autonomously luminescent cell may be used to accurately assess cellular viability.

In some embodiments, the method may comprise producing a control population comprising at least one control stem cell-derived autonomously luminescent cell. The control population is not contacted with the agent, but is otherwise treated similarly, or substantially similarly, to the at least one stem cell-derived autonomously luminescent cell that is contacted with the agent.

In said embodiments, the method may comprise comparing the measurement of the constitutive bioluminescent signal emitted from the at least one stem cell-derived autonomously luminescent cell to a constitutive bioluminescent signal emitted from the control population. The control population may increase the ease and accuracy of determining a negative and/or positive change in cell viability.

In such embodiments, the method may comprise determining that a decrease in the measured constitutive bioluminescent signal emitted from the at least one stem cell-derived autonomously luminescent cell relative to the constitutive bioluminescent signal emitted from the control population is indicative of a negative change in the cell viability of the at least one stem cell-derived autonomously luminescent cell resulting from contact with the agent. In embodiments, the method may comprise determining that the effect of the agent is cytotoxic. The method may comprise determining that the agent is fatal to the at least one stem cell-derived autonomously luminescent cell when the at least one stem cell-derived autonomously luminescent cell ceases production of the constitutive bioluminescent signal. In some embodiments, the method may comprise determining that the agent is not fatal to the at least one stem cell-derived autonomously luminescent cell when the at least one stem cell-derived autonomously luminescent cell does not cease production of the constitutive bioluminescent signal. Advantageously, this method allows for a valuable assessment of the cytotoxic effects of the agent.

The method may comprise determining that an increase in the measured constitutive bioluminescent signal emitted from the at least one stem cell-derived autonomously luminescent cell relative to the constitutive bioluminescent signal emitted from the control population is indicative of a positive change in the cell viability of the at least one stem cell-derived autonomously luminescent cell resulting from contact with the agent. In said embodiments, the method may comprise determining that the effect of the agent is therapeutic. Thus, this method results in a valuable assessment of the beneficial effect of the agent on the at least one stem cell-derived autonomously luminescent cell.

In some embodiments, the method may comprise subjecting the at least one stem cell-derived autonomously luminescent cell to a range of concentrations of the agent. This is advantageous in that a range of concentrations may allow for an assessment of dose dependent changes in the at least one stem cell-derived autonomously luminescent cell. A charting of the dose dependent changes is valuable in that it is a necessary part of understanding the relationship between agent exposure and cell viability. For example, when the agent is cytotoxic, the dose dependent changes may elucidate the agent's toxicity (e.g., determining $EC_{50}$, $IC_{50}$, $LD_{50}$, $LC_{50}$, and other similar measures of cytotoxicity).

In some embodiments, the method may comprise assessing the effect of the agent in real time. Advantageously, as there is no delay for the synthesis, excretion, and extracellular collection of a reporter protein, direct evidence of the agent's effect may be assessed in real-time.

In some embodiments, the method may comprise assessing the effect of the agent over two or more points in time. Advantageously, the at least one stem cell-derived autonomously bioluminescent cell may be immediately interrogated after contacting it with the agent to determine the agent's effect across any timescale from minutes to days. Further, because the stem cell-derived autonomously bioluminescent cell autonomously bioluminesces and said bioluminescence correlates with cell viability, the effect of an agent may be continuously monitored based on the cell viability, which provides valuable information regarding the onset of the effect of the agent as well as the duration of said effect. Greater knowledge of the agent's effect, such as when it the effect stabilizes, may enable a more confident assessment of the toxicity and/or therapeutic capability of the agent.

In some embodiments, the method may comprise assessing an agent for drug discovery based on assessing the effect of the agent. Assessing the cytotoxic and/or therapeutic effect of an agent is particularly valuable for drug discovery. Said assessment may advantageously contribute to ranking agents for consideration in drug discovery and to predict their fate after administration into the human body.

The methods disclosed herein for measuring the effect of an agent in at least one stem cell-derived autonomously bioluminescent cell are highly advantageous for therapeutic development as well as non-therapeutic chemical risk assessment. For example, screens testing cardiotoxicity increasingly utilize iPSC-derived cardiomyocytes coupled with an end-point style assay that is typically cell destructive (e.g., MTT, ATP based luciferase-luciferin assay), thus yielding a single measurement at one time point. Continuous cell monitoring is possible (e.g., impedance plates); however, equipment and consumable costs are high. In these formats, orchestrating replicates to capture kinetic toxicity data becomes expensive and introduces experimental variation even with modest increases in scale.

To address these problems, autonomously bioluminescent cardiomyocytes derived from autobioluminescent stem cells may be used to monitor cardiotoxicity. Said cardiomyocytes may provide real time, continuous cardiotoxicity monitoring over an extended time. Moreover, costs would be low, and there would be less risk of experimental variation. Thus, the methods disclosed herein may lead to a better contextual understanding of cytotoxic and/or therapeutic effects as well as greater clinical utility.

WORKING EXAMPLES

Working Example 1—Development of a Continuously Autobioluminescent Human iPSC Line In order to traverse the limitations imposed by the present techniques for examining, for example, stem cell viability, migration, location, and fate, experiments were undertaken to implement autonomous bioluminescent reporter genes into stem cells to enable substrate-free autobioluminescent imaging of stem cells under in vitro and/or in vivo modalities. Specifically, it was sought to implement luxC, luxD, luxA, luxB, luxE, and frp (luxCDABEfrp) genes into stem cells in order to engineer stem cells to emit constitutive autobioluminescence.

In attempting to develop said cell line, it was determined that simply expressing luxCDABEfrp genes in a cell line is not sufficient for practical purposes. In fact, it was discovered that the straightforward expression of the genes, as one would expect from any routine transfection procedure, does not produce sufficient autonomous luminescent output in the vast majority of cell lines, nor is it capable of producing any autonomous luminescent output in some cell types, such as stem cells. Indeed, expression of this cassette in induced pluripotent stem cells (iPSCs) failed to produce clonal lines exhibiting measurable autonomous luminescence despite qPCR-based analysis confirming genomic integration of the luxCDABEfrp genes. Therefore, merely expressing luxCDABEfrp genes in stem cells is insufficient for producing a functional level of autonomous luminescence in stem cells.

Development of CBA-luxCDEFAB

Therefore, it was sought to identify a promoter capable of driving the expression of the lux genes simultaneously. However, not all promoters are capable of driving the expression of multiple lux genes simultaneously. Working in immortalized cell lines, a variety of published promoter sequences were evaluated, and it was determined that there was no correlation between autonomous luminescent output and the published activity of promoters for driving single-gene reporter systems (i.e., firefly luciferase or GFP). This problem became especially evident when it was attempted to transition the synthetic lux operon to stem cells. For instance, the following promoters were surprisingly discovered to be incapable of supporting autonomous luminescent output in iPSCs, even when using an empirically-determined ideal gene expression ratio (discussed below): CMV, EF1a, Ubc, PGK1, DNMT3, Nanog, Oct4, ActB, SV40. Moreover, unexpectedly, none of the synthetic promoters previously developed by the Ellis lab (described in PubMed: 19404254) specifically for strong expression in iPSCs were capable of supporting autonomous luminescent output in iPSCs.

Figure 3A:
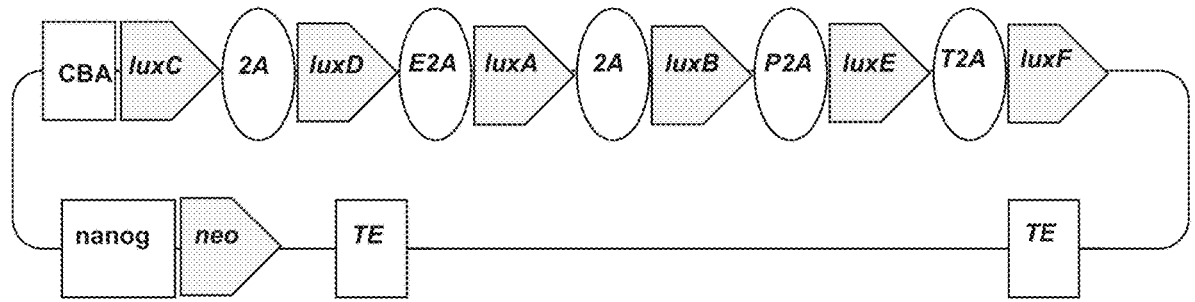
FIGS. 3A-3C. Schematics of the lux operon configurations used to produce autobioluminescence in human induced pluripotent stem cells (iPSCs), according to embodiments of the disclosure.

Ultimately, contrary to the published activity of the tested promoters, this work unexpectedly revealed that it is necessary to carefully pair the genes with a promoter that not only imparts strong transcriptional activity, but is also capable of driving expression of long transcriptional units to obtain a functional level of autonomous luminescence in stem cells. Accordingly, it was empirically determined that the chicken beta-actin (CBA) promoter results in a functional level of autonomous luminescence and remains functional across a variety of cell types. FIG. 3A illustrates this new construct, CBA-luxCDEFAB, wherein viral 2A elements (2A) were employed as linker regions between each of the luxCDABEfrp genes to increased transcriptional efficiency. Moreover, a nanog promoter drives the neomycin selection marker (FIG. 3A). Presently, the CBA promoter is employed as the default promoter for the lux system when moving into new cell types. Then, alternative promoter activity is screened for on a line-by-line basis.

Development of Two Vector Lux System

Transfection of CBA-luxCDEFAB resulted in weak, but measurable autonomous luminescent output (data not shown). Nonetheless, it still failed to support efficient clonal selection and could not maintain the autonomous luminescent phenotype for more than twenty-four (24)-seventy-two (72) hours. Such data suggested that lux operon expression in iPSCs is capable of supporting autonomous luminescence; however, some or all of the lux system components were not sufficiently expressed to support efficient autonomous luminescent production. It is suspected that the genes distal to the promoter in the CBA-luxCDEFAB construct may have decreased transcriptional activity.

Figure 3B:
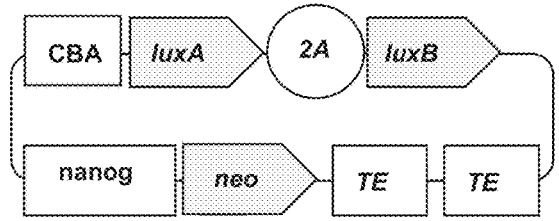
Figure 3C:
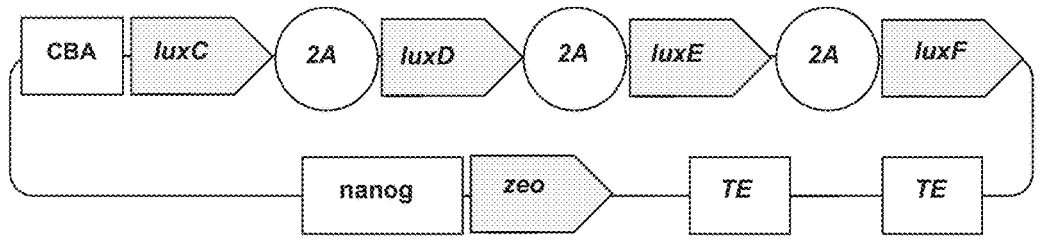

Therefore, in an attempt to ensure that all of the system components were sufficiently expressed, the lux operon was broken into its component subsections, the luciferase generating luxAB genes and the luxCDEfrp luciferin generation genes, as illustrated in FIGS. 3B-3C, respectively. The components were separated onto two vectors in order to decrease the distance between certain genes and the promoter as compared to placing the entire lux system under the operation of a single promoter.

The components were then transiently co-expressed from two independent vectors (FIGS. 3B-3C) at a variety of molar ratios in iPSCs, ranging from a molar ratio of 1:1 luxCDEF:luxAB to 40:1 luxCDEF:luxAB—a vast overexpression of the luciferin generation genes relative to the luciferase generating genes. As illustrated in FIG. 2A, the average radiance emitted (p/s/cm$^2$/sr) from iPSCs and hADMSCs transiently expressing the split lux operon (nanog-neo-CBA-luxAB and nanog-zeo-CBA-luxCDEF) at a 1:1 molar ratio was charted as compared to identical cells expressing the same amount of luxAB and an increasing amount of luxCDEF.

As illustrated in FIG. 2A, the molar ratios of 1:1, 5:1, 10:1, 20:1, 30:1, and 40:1 of luxCDEF:luxAB were tested. The luminescent output peaked (approximately $6 \times 10^3$ p/s/cm$^2$/sr) at a molar ratio of 20:1 luxCDEF:luxAB. Below the 20:1 ratio, there was little to no luminescent output observed. Specifically, the 10:1 ratio resulted in approximately half the output as the 20:1 ratio, and there was little to no luminescent output observed at the molar ratios of 1:1 and 5:1. Above the 20:1 ratio, luminescent output remained robust. Both 30:1 and 40:1 resulted in considerable luminescent output of approximately $4 \times 10^3$ p/s/cm$^2$/sr and $5 \times 10^3$ p/s/cm$^2$/sr, respectively.

To determine whether these results hold true in other cell lines, the two vector lux system was then implemented into human adipose derived mesenchymal stem cells (hADMSCs), the LN229 cell line, and the U87 cell line at varying molar ratios of luxCDEF:luxAB. For hADMSCs, the trend remained largely true. In this cell line, the molar ratios of 1:1, 10:1, 20:1, 30:1, and 40:1 of luxCDEF:luxAB were tested. As illustrated in FIG. 2B, the luminescent output peaked (approximately $9 \times 10^3$ p/s/cm$^2$/sr) at a molar ratio of 30:1 luxCDEF:luxAB. The 20:1 and 40:1 ratios produced similarly robust output of approximately $8 \times 10^3$ p/s/cm$^2$/sr and $6 \times 10^3$ p/s/cm$^2$/sr, respectively. Little to no output was observed in connection with the 1:1 and 10:1 ratios.

Figure 2C:
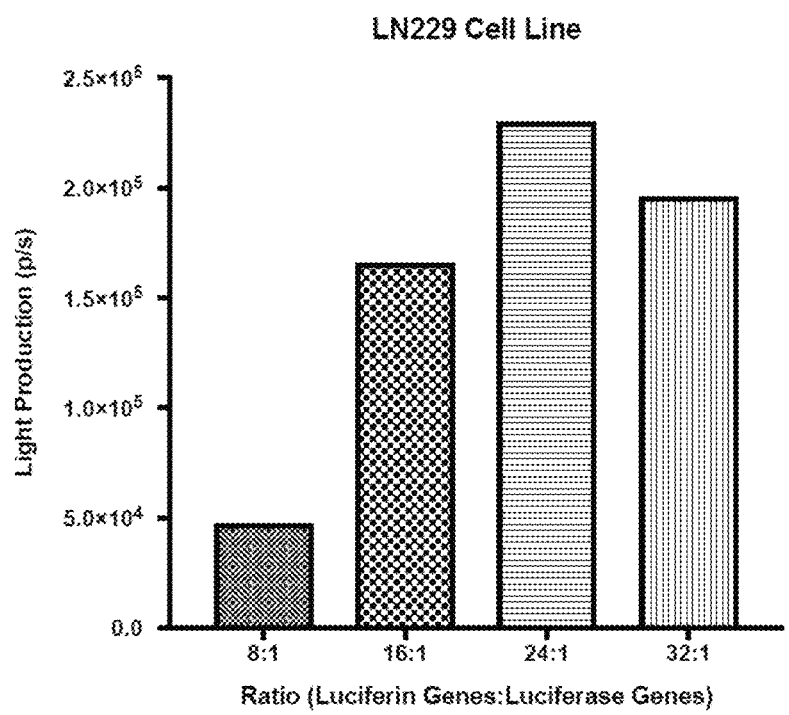
Figure 2D:
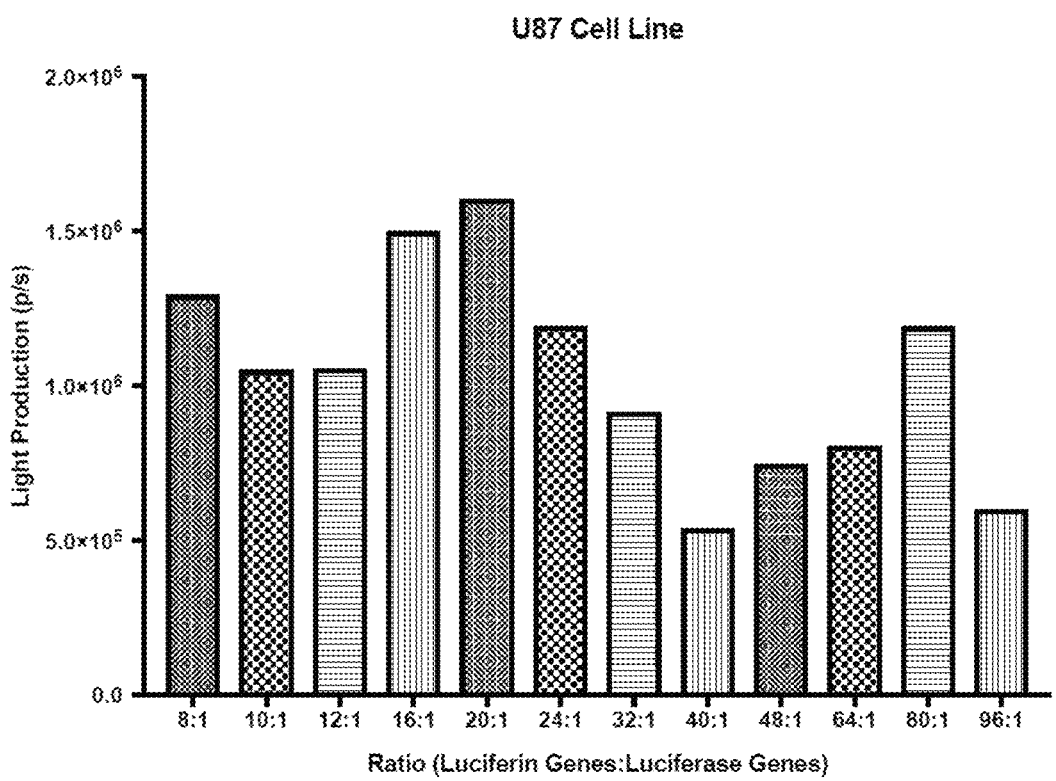

Similar results were obtained for the LN229 cell line and the U87 cell line. The resulting light production (p/s) generated from varying ratios was measured for both cell lines. Similar to the results obtained for iPSCs and hADMSCs, an overexpression of approximately 16:1 to 30:1 of luxCDEF:luxAB resulted in the most robust bioluminescent output, as illustrated in FIGS. 2C and 2D. In the U87 cell line, light production was unexpectedly found to increase at ratios between 48:1-96:1. However, unlike the increased light production that occurred at the 16:1 to 24:1 ratios, these higher ratios resulted in cell morbidity such that light production was not sustainable for the cell line.

Pursuant to these unexpected discoveries regarding an overexpression of the luciferin generation genes relative to the luciferase generating genes, a stable, autoluminescent iPSC line was generated by co-transfecting the luxCDEfrp and luxAB vectors at a 20:1 ratio to generate a robust autobioluminescent phenotype. Antibiotic-resistant clonal lines were selected, and then, the lineage that produced the greatest amount of continuous autonomous luminescent signal was selected. This lineage was denoted as iPSC-luxAB/CDEF.

Figure 4:
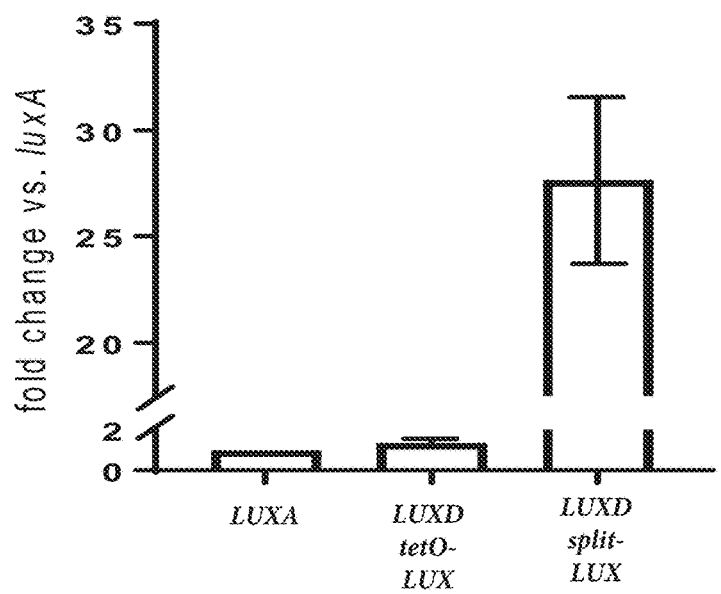
FIG. 4. qPCR confirms lux operon gene ratios in iPSC-AB/CDEF genomic DNA following extended time in culture. Genomic DNA from passage 11 (approximately 3 months in culture) human induced pluripotent stem cells (iPSCs) lines bearing the split lux operon (nanog-neomycin-CBA-luxAB and nanog-zeocin-CBA-luxCDEF) and the polycistronic tetracycline repressible lux operon (nanog-neomycin-tetO-luxCDABEF and nanog-zeocin-CBA-tTA) was probed by qPCR for luxA and luxD to determine whether the genes occurred in an approximately 1:1 or greater ratio.
Figure 5A:
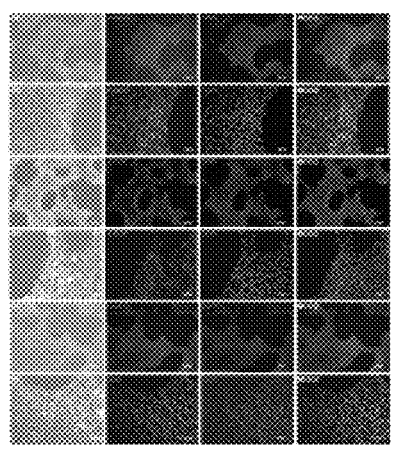
FIGS. 5A-5C. Lux operon-expressing human induced pluripotent stem cell (iPSC) lines, according to an embodiment of the disclosure, maintain protein markers associated with pluripotency.
Figure 5B:
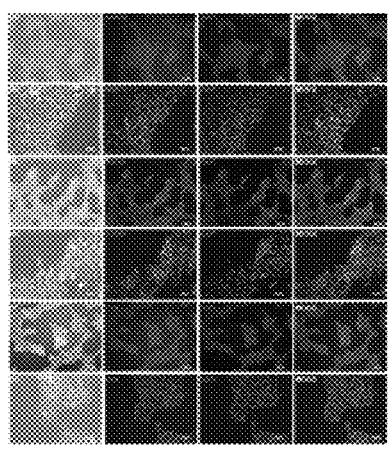
Figure 6A:
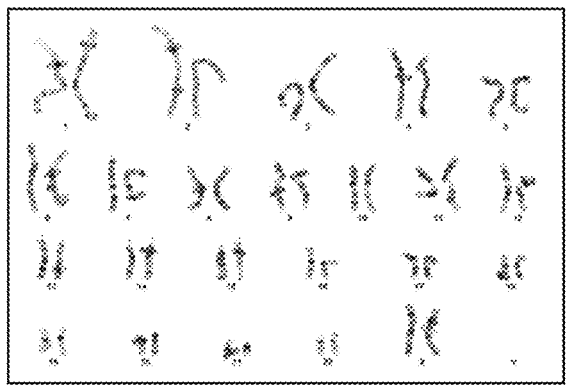
FIGS. 6A-6B. Lux operon-expressing human induced pluripotent stem cell (iPSC) lines, according to an embodiment of the disclosure, retain normal karyotypes following extended time in culture.

Genomic qPCR-based analysis confirmed the 20:1 target ratio of the luxCDEF and luxAB components, as illustrated in FIG. 4. Long-term culture of this lineage (>3 months) did not reveal any impact on growth rate relative to the wild type parent line (not shown) and the cells retained both their wild type pluripotency markers (FIG. 5B) and karyotype (FIG. 6A) throughout this time, suggesting that integration of the split lux operon did not perturb pluripotency.

Thus, continuous, exogenous substrate-independent, self-generated bioluminescent light in human iPSCs was developed through implementation of the luxCDABEfrp genes into iPSCs. The cell line's autobioluminescence is emitted in real-time to bioindicate cellular and molecular mechanisms coupled to bioluminescent outputs. Moreover, due to the autobioluminescent phenotype, the stem cells may be continuously interrogated without investigator interaction to initiate bioluminescence, thus allowing for the assessment of both signal duration and intensity dynamics from a single sample. Further, the autobioluminescent phenotype of the stem cells may enable non-invasive continuous optical imaging in a variety of applications, including but not limited to, real-time, non-invasive, continuous, and substrate-free tracking, identifying, and/or measuring the stem cells' viability, migration, fate, and/or lineage-specific differentiation. Thus, the iPSC-luxAB/CDEF line may effectively remedy many of the significant impediments hindering the implementation of stem cell-based therapies in clinical practice and would be a significant asset to the regenerative medicine field.

Discussion of Overexpression of Luciferin Generation Genes

Ultimately, in developing the iPSC-luxAB/CDEF line, it was highly unexpected that an overexpression of the luciferin production portion of the bacterial luciferase gene cassette (the luxCDEfrp genes) relative to the luciferase production portion (the luxAB genes) produced the most robust autobioluminescent signal. In fact, this overexpression is in notably different from the molar ratios of all previous autonomously luminescent cell lines—all of which have employed a 1:1 ratio of luxCDEfrp to luxAB.

Indeed, this result is counterintuitive and unexpected for at least two reasons. First, the luciferin compound produced by the system is a long chain aldehyde that is cytotoxic at elevated levels. An overexpression of the luciferin production portion of the lux cassette may result in an accumulation of the long chain aldehyde, thereby increasing the risk of cytotoxic effects. These effects would be expected, in turn, to negatively impact the health of the stem cell, which would cause a reduction of autobioluminescence.

Second, these genes re-route metabolites from both metabolic and oxidation/reduction processes within the cell. Therefore, it would be expected that an overexpression of luxCDEfrp relative to luxAB would negatively impact cellular health, growth, and physiology due to either cytotoxicity resulting from an accumulation of the long chain aldehyde and/or interference with metabolic activity. Reduced cellular health would then in turn result in reduced autonomous luminescent output. Therefore, there is no reason to expect that an overexpression of luxCDEfrp genes would produce the most robust bioluminescent output. Surprisingly, however, the results in this study unexpectedly revealed that iPSC cells demonstrating overexpression of luxCDEfrp emitted increased autonomous luminescence while continuing to present normal physiology and metabolic activity levels.

These surprising results led to an additional unexpected finding. That is, independent of the cell line serving as a host, there is a common ratio of luxCDEfrp to luxAB that consistently produced the highest level of autonomous luminescent output. For all cell types tested, an approximate 20:1-30:1 ratio resulted in the highest expression (FIGS. 2A-2D). Such a result is surprising and unexpected given the differences in the physiology and metabolic activity between cell types. It would be expected that this ratio would necessarily greatly differ for every cell type, given that each cell type has different basal oxidation states and availability to the metabolic resources required for luciferin generation.

Thus, this study produced at least two highly unexpected conclusions. The first being that an overexpression of the luciferin generation genes produces an unexpectedly great autobioluminescent signal in all cell lines tested, including stem cells. The second being that a 20:1-30:1 ratio resulted in the highest expression in all cell lines tested.

Development of Six Vector Lux System

After development of the iPSC-luxAB/CDEF line, experiments were undertaken to assess whether expression of the lux genes from individual plasmids would result in high levels of bioluminescence. To make this assessment, each of luxABCDEF were synthesized and cloned separately into six different expression vectors. The six expression vectors were then co-transfected into HEK 293 cells. In assessing bioluminescent output, it was unexpectedly discovered that expressing each of the lux genes independently from unique plasmids results in a significant increase in light production as compared to either expressing multiple lux genes from a single plasmid or multiple lux genes from a single promoter when the full set of lux genes are expressed across multiple plasmids. In fact, this approach resulted in bioluminescent levels similar to the widely used firefly luciferase.

Figures 7A, 7B:
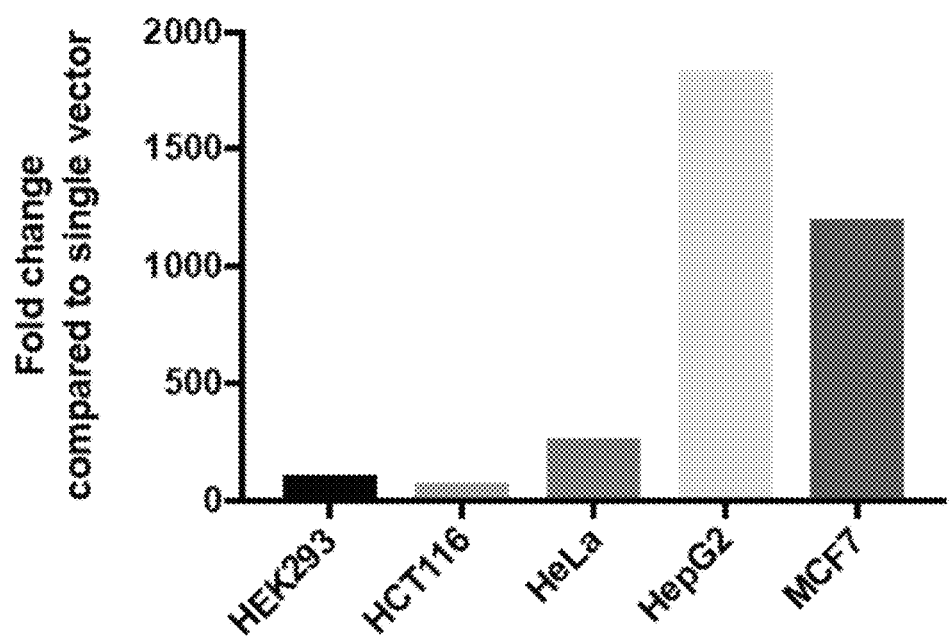
FIGS. 7A-7B. HEK293, HCT116, HeLa, MepG2, and MCF7 cells were transfected with either a single vector expressing 2A-linked bacterial luciferase genes or six individual vectors each expressing one of the six bacterial luciferase genes. Light output from each cell type was measured 48 h after transfection.

The six vector expression approach was subsequently validated across multiple cell types. Specifically, HEK293, HCT116, HeLa, HepG2, and MCF7 cells were transfected with either a single vector expressing 2A-linked bacterial luciferase genes or six individual vectors each expressing one of the six bacterial luciferase genes. Light output from each of the foregoing cell types was then measured 48 hours post-transfection (performed in triplicate). As illustrated in FIGS. 7A and 7B, the six vector expression approach resulted in increased light output in all cell types tested, ranging from a 78 fold change in light output for the HCT116 cells to a 1838 fold change in light output from the HepG2 cells.

Figure 8:
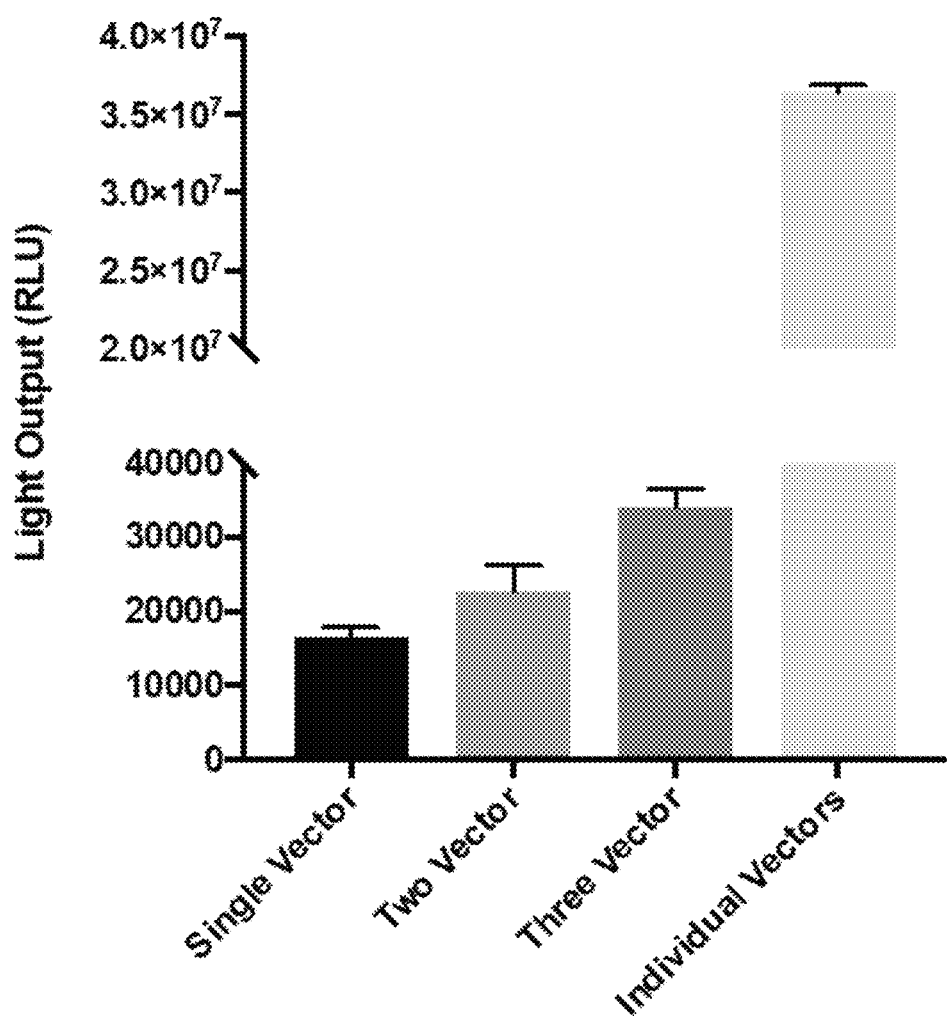
FIG. 8. HEK293 cells were transfected with either (1) a single vector expressing all six 2A-linked bacterial luciferase genes; (2) two vectors with one expressing luxAB and the other expressing luxCDEfrp; (3) three vectors with one expressing luxAB, the second expressing luxCDE, and the third expressing frp; or (4) six individual vectors each expressing one of the six bacterial luciferase genes. Light output was measured 48 h after transfection with the cells held at 37° C.

Furthermore, this six vector expression approach also improves the thermostability of the bioluminescent signal. Specifically, HEK293 cells were transfected with either (1) a single vector expressing all six 2A-linked bacterial luciferase genes; (2) two vectors with one expressing luxAB and the other expressing luxCDEfrp; (3) three vectors with one expressing luxAB, the second expressing luxCDE, and the third expressing frp; or (4) six individual vectors each expressing one of the six bacterial luciferase genes. Light output was measured 48 hours after transfection with the cells held at 37° C. (performed in triplicate). As illustrated in FIG. 8, the six vector expression approach resulted in increased light output (approximately $3.5 \times 10^7$ RLU) as compared to the other approaches (producing light outputs ranging from approximately 15,000 RLU to 35,000 RLU). Thus, the six vector expression approach significantly improved the thermostability of the bioluminescent signal as compared to other expression approaches utilizing a lesser number of vectors.

Finally, it was further confirmed that the aforementioned overexpression of the luciferin generation genes relative to the luciferase generating genes produced the most robust autobioluminescent phenotype for the six vector system. Specifically, the ratios of the transfected plasmids were varied such that there was an increased amount of luxCDEfrp relative to luxAB. It was determined that light output increased with an overabundance of the fatty acid reductase components.

Thus, through the aforementioned research, it was surprisingly discovered that the expression of lux genes from individual plasmids in certain unexpected ratios (such that luxCDEfrp are overexpressed relative to luxAB) result in robust thermostable autobioluminescence across multiple cell types. Advantageously, the increase in light production resulting from gene expression on individual plasmids enables new capabilities for the eukaryotic bacterial luciferase system, such as single cell imaging (see C. Gregor et al., Autonomous bioluminescence imaging of single mammalian cells with the bacterial bioluminescence system, PNAS, Vol 116, No. 52, 2019), organelle tagging, use of bioluminescence for sorting cells using flow cytometery, and visualizing smaller numbers of cells in animal models.

Working Example 2—Autobioluminescent Measurement of iPSC Cell Population Size and Viability After development of the iPSC-luxAB/CDEF line, experiments were undertaken to assess whether said cell line is capable of reporting cell population size. First, to assess whether the luminescent signal emitted by a population of iPSC-luxAB/CDEF cells is proportional to the total cell number of the population, iPSC-luxAB/CDEF cells in a volume of medium were seeded in a well plate at a range of determined cell densities. Identical platings of untransfected cells were made along with platings of medium to serve as positive and negative controls. The cells were incubated under standard growth conditions for twenty four (24) hours. After this time period, the plate was imaged for luminescent output, as illustrated in FIG. 9A. Bioluminescent readings were obtained using an IVIS Lumina imaging system (PerkinElmer). This process was repeated six times to obtain six biological replicates. For all measurements, the background values derived from the medium only controls were subtracted to provide background corrected averages. Luminescent output was averaged, and the average values were used to determine standard errors of the mean for each assay.

The fold change in the resulting average radiant luminescence ($p/s/cm^2/sr$) relative to the background was plotted against the initial seeding cell density. It was determined that the average radiant luminescence ($p/s/cm^2/sr$) emitted from the iPSC-luxAB/CDEF cells correlate strongly with the number of plated cells ($R^2=0.93$), as illustrated in FIG. 9B. This result determined that the average luminescent signal emitted by a population of iPSC-luxAB/CDEF cells is proportional and correlates to the total cell number, thereby enabling quantification of the cell population size based on the average emitted signal.

Furthermore, experiments were undertaken to assess whether said cell line is capable of reporting cell viability. First, iPSC-luxAB/CDEF cells in a volume of medium were seeded in a well plate at a range of determined cell densities. Identical platings of untransfected cells were made along with platings of medium to serve as positive and negative controls. The cells were incubated under standard growth conditions for twenty four (24) hours. After this time period, the plate was imaged for luminescent output. Bioluminescent readings were obtained using a IVIS Lumina imaging system (PerkinElmer).

Following this reading, the plate was subjected to viability analysis using the CellTiter 96 Non-Radioactive Cell Proliferation Assay (MTT) according to the manufacturer's instructions. MTT assay values were obtained as absorbance values at 570 nm using a Synergyll plate reader (Biotek) and reported as percentage of absorbance relative to untreated control cells. For all measurements, the background absorbance values derived from the medium only controls were subtracted to provide background corrected averages. This process was repeated six times to obtain six biological replicates. Absorbance values were averaged, and the average values were used to determine standard errors of the mean for each assay.

Figure 9C:
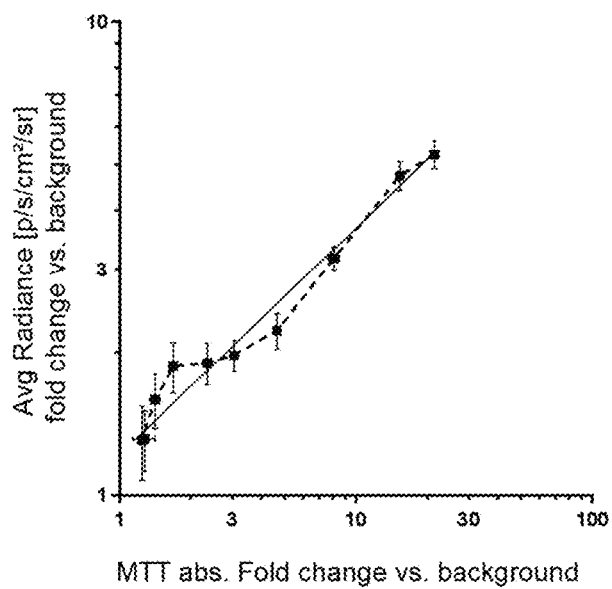

The fold change in the resulting average radiant luminescence (p/s/cm²/sr) relative to the background was plotted against the fold change in MTT absorbance (570 nm) relative to background. The resulting correlation was high ($R^2=0.98$) suggesting the lux operon accurately reports cell viability in the iPSC-luxAB/CDEF line (FIG. 9C).

Thus, this study verified that the average emitted autobioluminescent output from iPSC-luxAB/CDEF cells strongly correlates to the number of cells and accurately reports cell viability. The correlation stems from the lux system link to endogenous cell metabolism. In combination, these data demonstrate continuous, exogenous substrate independent, self-generated bioluminescent light in human iPSCs that is, furthermore, capable of reporting cell population size and viability on par with an established assay.

Working Example 3—Tracking Compound Toxicity with Autonomous Luminescent Output

As detailed above, the autonomous luminescent output from iPSC-luxAB/CDEF cells faithfully reports both cell population size and viability. Therefore, experimentation was undertaken to determine whether the iPSC-luxAB/CDEF line could report changes in cell viability in response to treatment with compounds of known toxicity.

First, iPSC-luxAB/CDEF cells were seeded in a volume of medium in two separate multi-well plates. Identical platings of untransfected cells were made along with platings of medium to serve as positive and negative controls. For the first plate, the cells were subjected to increasing concentrations of the cytotoxic compound doxorubin. For the second plate, the cells were subjected to increasing concentrations of the cytotoxic compound rotenone. The cells were then incubated under standard growth conditions for twenty four (24) hours. After this time period, the plates was imaged for luminescent output. Bioluminescent readings were obtained using a SynergyII plate reader (BioTek).

Following this reading, the plates were subjected to viability analysis using the MTT assay according to the manufacturer's instructions. MTT assay values were obtained as absorbance values at 570 nm using a SynergyII plate reader (BioTek) and reported as percentage of absorbance relative to untreated control cells. For all measurements, the background absorbance values derived from the medium only controls were subtracted to provide background corrected averages. Absorbance values from each treatment level were averaged, and the average values for each of the plates were used to determine standard errors of the mean for each assay.

Treatment of the iPSC-luxAB/CDEF line with a range of doxorubicin concentrations resulted in dose dependent changes to the autonomous luminescent signal output indicative of changing cellular viabilities that also correlated strongly ($R^2=0.99$) with measurements made by MTT (FIG. 10).

In sum, these data illustrate that the iPSC-luxAB/CDEF line is capable of reporting changes in cellular viability resulting from compound exposure and that the autonomous luminescent signal changes in response to cell stress and death.

Working Example 4—In Vivo Imaging of Autonomous Luminescent hADMSCs

Having established the iPSC-luxAB/CDEF cell line, experiments were undertaken to engineer multipotent mesenchymal stem cells that autonomously produced a luminescence signal using the same lux operon vectors developed for iPSCs, that is, CBA-luxCDEF and CBA-luxAB.

Figure 11:
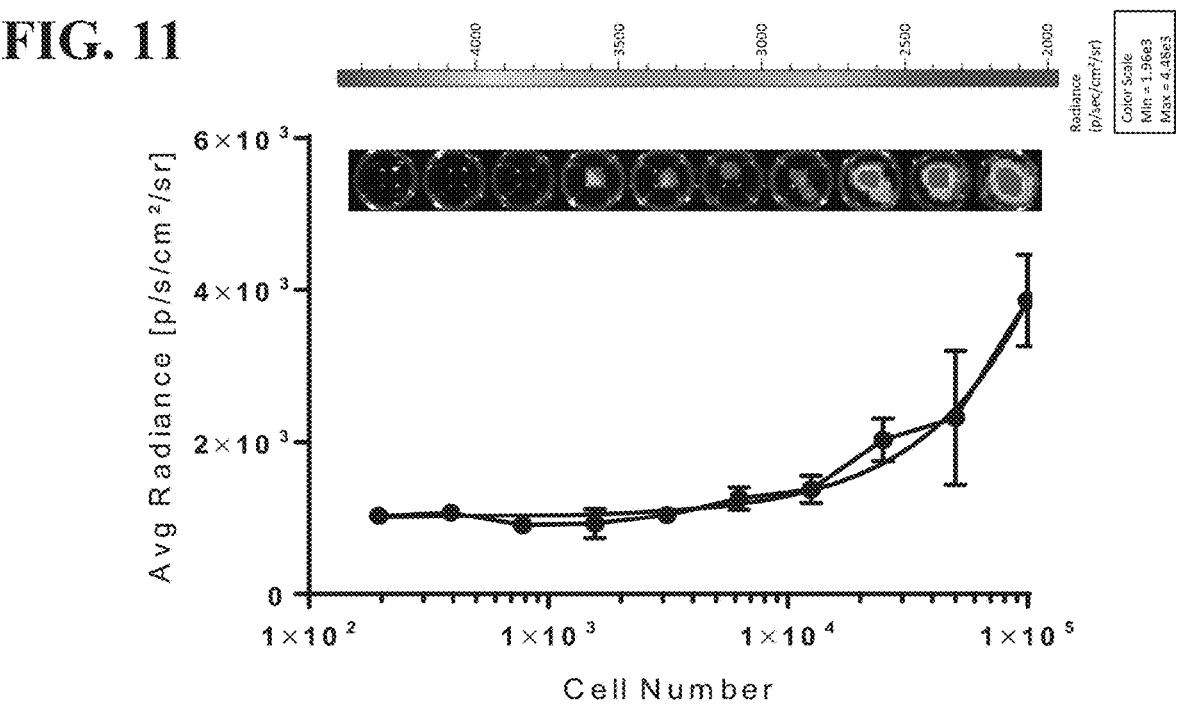
FIG. 11. Genomic integration of CBA-luxCDEF and CBA-luxAB produced stable mesenchymal stem cell (MSC) clonal lines expressing autonomous luminescence that strongly correlates with cell number, according to an embodiment of the disclosure.

First, as detailed in Working Example 1 above, various molar ratios of 1:1, 10:1, 20:1, 30:1, and 40:1 of luxCDEF:luxAB were tested in hADMSC cells. As illustrated in FIG. 2B, the luminescent output peaked at a molar ratio of 20:1-30:1, which is approximately the same as that observed for iPSCs (see FIG. 2A for comparison). Similar to the iPSC-luxAB/CDEF cell line, genomic integration of CBA-luxCDEF to CBA-luxAB at this ratio produced stable MSC clonal lines expressing autonomous luminescence. Using similar methods as described in Working Example 2 to assess the correlation of iPSC-luxAB/CDEF line autobioluminescent output with population size, it was likewise determined that the signal emitted by the autobioluminescent hADMSC cell line likewise strongly correlates ($R^2=0.98$) with cell number, as illustrated in FIG. 11. Thus, these results demonstrate the development of a continuous, exogenous substrate independent, self-generated bioluminescent light in hADMSCs that is capable of reporting cell population size.

Next, experimentation was undertaken to determine whether the MSCs expressing autonomous luminescence can be imaged in vivo. First, three different total amounts of autonomously luminescent MSCs were prepared. These preparations were injected intraperitoneally (IP) into FVB inbred mice at the locations indicated by the circles in FIG. 12A. The mice were then imaged under anesthesia. The fold change in the resulting average radiant luminescence (p/s/cm²/sr) was plotted against the total cell number injected (FIG. 12B). It was determined that the average radiant luminescence (p/s/cm²/sr) emitted from the MSCs correlated strongly with the injected cell number ($R^2=0.99$), as seen in (FIG. 12B).

This result has significant implications. First, it demonstrates that MSC-based autonomous luminescence can be used for in vivo cell imaging. Second, it demonstrates that MSC-based autonomous luminescence can be used to monitor total cell number in vivo. Accordingly, this reagent-free in vivo imaging in a mouse model removes concerns over stress responses and injection site inflammation by allowing for data acquisition without repetitive needle sticks. Further, this cell line allows for non-invasive optical imaging to occur continuously over the lifetime of the animal.

Next, experimentation was undertaken to assess whether the in vivo cell migration of autonomously bioluminescent MSCs could be tracked. First, two (2) million autonomously luminescent MSCs were delivered via tail injection into FVB mice. At one (1) hour post-injection, the dorsal aspect was then imaged for autonomous luminescent output. No autonomous luminescent signal was observed (FIG. 13A).

Nonetheless, cellular accumulation of autonomously luminescent MSCs in the lungs was readily detectable following sacrifice and dissection (FIG. 13B). This result suggests that despite not producing a sufficiently strong signal to penetrate from a deep tissue in vivo (i.e., the lungs), the autonomously luminescent MSCs survived transit through the circulatory system and revealed accumulation in the lungs, thereby demonstrating that in vivo cell migration of autonomously luminescent MSCs can be tracked.

Working Example 5—Gene Expression Monitoring in iPSCs and Cardiomyocytes with the Lux Operon Expression of the lux operon is genetically controlled by a promoter whose activity has a direct influence on the overall autobioluminescent output. This trait has previously been leveraged to produce lux-based bioreporters signaling the presence of various compounds, such as estrogen. Accordingly, after verification that the lux operon could be constitutively expressed in iPSCs, experiments were undertaken to develop reporter-based genetic configurations capable of reporting changes in gene expression as opposed to cell viability.

Nonetheless, the previous methods for developing lux-based bioreporters proved to be insufficient for adoption of the lux expression system to serve as a reporter for gene activation events in stem cells. That is, the available promoter options that would commonly be used for reporter-based genetic configurations did not result in significant autobioluminescent output. Indeed, using the available promoter options resulted in little to no autobioluminescent output following induction.

Figure 14:
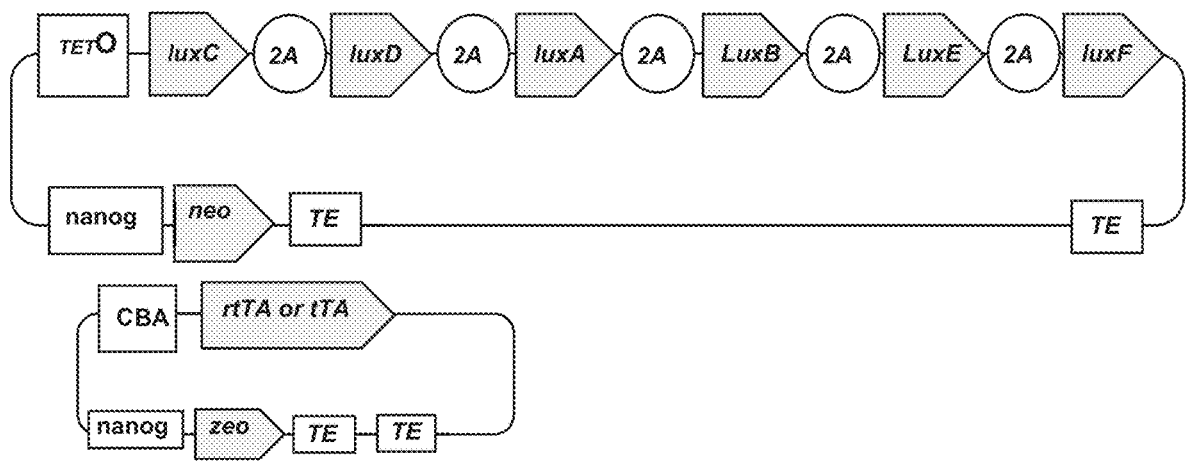
FIG. 14. Schematic of the lux operon configuration used to produce inducible or repressible autobioluminescence in human induced pluripotent stem cells (iPSCs), according to embodiments of the disclosure. The viral 2A segmented, polycistronic lux operon is driven by a modified tetracycline response element ($TET^O$) and flanked by sequence elements to facilitate transposon mediated genomic integration (TE). The nanog promoter (nanog) drives the neomycin resistance gene (neo) to provide G418 selection following integration. The transactivator (tTA) or the reverse transactivator (rtTA) is driven by a chicken beta-actin promoter (CBA). The CBA-driven transactivator (tTA) provides constitutive lux expression that is turned off in the presence of tetracycline or one of its analogs. In contrast, the CBA-driven reverse transactivator (rtTA) expresses lux in the presence of tetracycline or one of its analogs.

This unexpected issue was overcome by developing synthetic gene amplification circuits to control autobioluminescent gene expression in stem cells. To develop this synthetic gene amplification circuit, a tetracycline promoter (doxycycline-responsive) was cloned upstream of the polycistronic luxCDABEF operon (referred to as tet-luxCDABEF) and genomically co-integrated it into iPSCs with either a vector carrying a CBA-driven transactivator (tTA) or a vector carrying a CBA-driven reverse transactivator (rtTA) (FIG. 14).

Figure 15A:
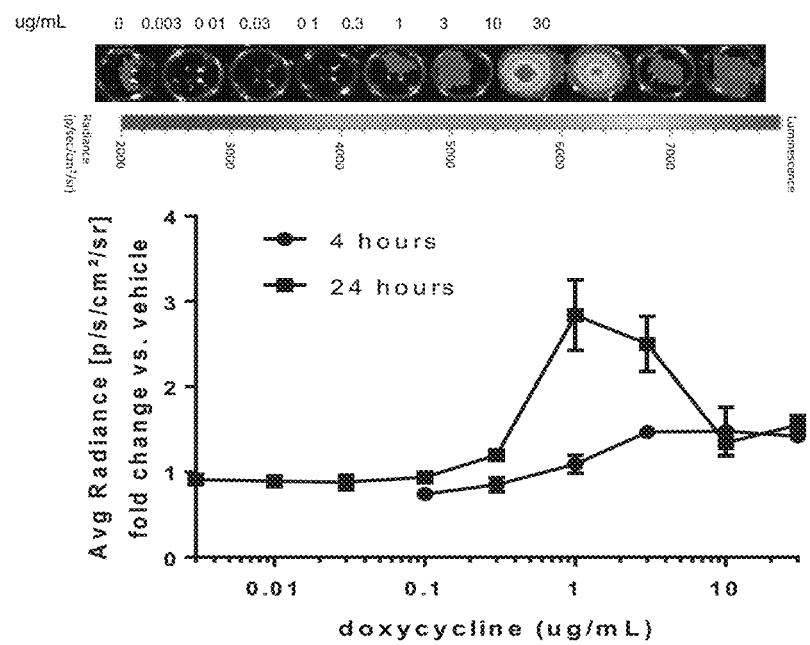
FIGS. 15A-15B. The lux operon functions as a reporter of gene expression.

Tet-luxCDABEF IPSCs with genomically integrated rtTA (doxycycline inducible) were exposed to increasing amounts of doxycycline for four (4) hours and twenty (24) hours. Bioluminescence measurements were obtained using an IVIS Lumina imaging system. The fold change in the resulting average radiant luminescence (p/s/cm$^2$/sr) relative to the background was plotted against the corresponding dose of doxycycline. As shown in FIG. 15A, the cell line showed a clear pattern of autobioluminescent induction in response to doxycycline, thus verifying the development of a lux-based stem cell bioreporter capable of monitoring gene expression.

Figure 15B:
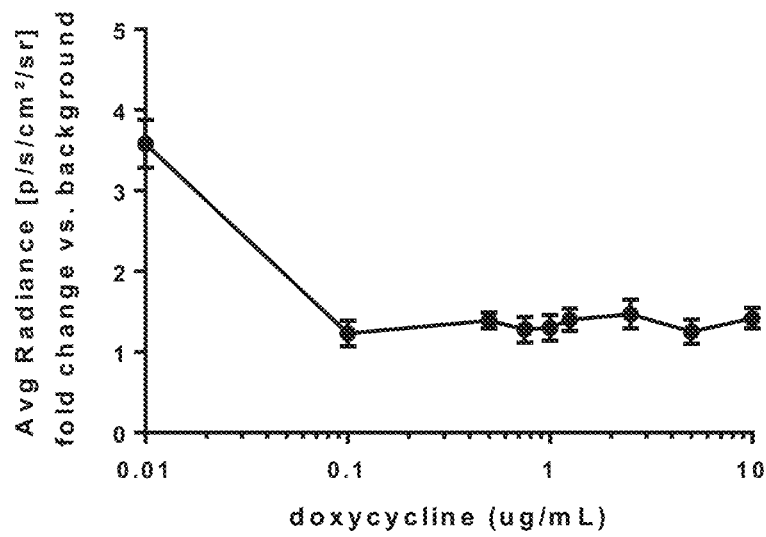

In contrast, Tet-luxCDABEF IPSCs with genomically integrated tTA (doxycycline repressible) were likewise exposed to increasing amounts of doxycycline. Bioluminescence measurements were obtained using an IVIS Lumina imaging system. The fold change in the resulting average radiant luminescence (p/s/cm$^2$/sr) relative to the background was plotted against the corresponding dose of doxycycline. The resulting data showed that the cell line's continuous autobioluminescence was shut off after exposure to doxycycline (FIG. 15B).

Further, like the iPSC-luxAB/CDEF line, amplification of the luciferin production portion (luxCDEfrp) leads to robust autobioluminescent output. Again, this result is wholly unexpected as it would be expected that overproduction of the aldehyde luciferin component would have cytotoxic effects or adversely interfere with cellular metabolism, as described above.

Figure 5C:
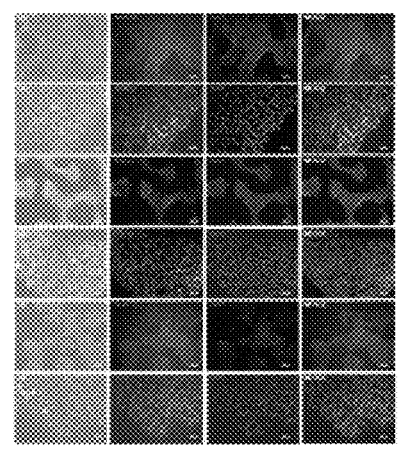
Figure 6B:
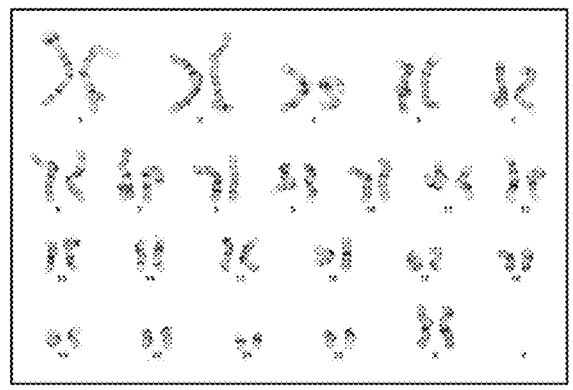

Moreover, long-term culture of the tetracycline repressible cell line (>3 months) did not reveal any impact on growth rate relative to the wild type parent line (not shown) and the cells retained both their wild type pluripotency markers (FIG. 5C) and karyotype (FIG. 6B) throughout this time, suggesting that integration of the split lux operon did not perturb pluripotency.

Figure 16:
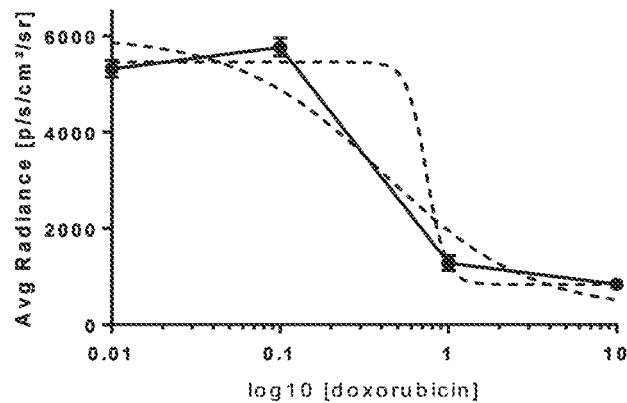
FIG. 16. Human induced pluripotent stem cells (iPSCs) bearing genomically integrated polycistronic lux operon (luxCDABEF) under control of the tetracycline responsive promoter (tet-luxCDABEF) and a separately integrated CBA-driven transactivator (tTA) were differentiated into cardiomyocytes (CMs). After maturation for approximately 1.5 weeks, the CMs were subjected to doxorubicin exposure. CMs were exposed to doxorubicin at the indicated range of concentrations for 18 hours prior to imaging. The estimated $EC_{50}$ is 0.41-0.74 uM.

These data show polycistronic lux-based autobioluminescence is possible in iPSCs but requires strong genetic induction. These results also demonstrate that the lux operon can be used to monitor gene expression where autobioluminescence serves as a proxy for genetic activation. Finally, as illustrated in FIG. 16, both tet-responsive iPSC lines were capable of autobioluminescent expression when differentiated into cardiomyocytes that were able to report cardiotoxicity.

This is a highly advantageous development as these bioreporters can be continuously monitored in an automated fashion to determine the onset of signal initiation. Moreover, unlike reporter systems that require the additional of luciferin, signal generation herein is fully self-generated. That is, the bioreporter can be continuously monitored without the need for interaction. Thus, signal duration and intensity can be determined from a single sample without concern as to any influential effects of a luciferin treatment.

Working Example 6—Cardiac Specific Lux Operon Expression

After verification that the lux operon could report gene activation events, experimentation was undertaken to determine whether the expression system could serve as a reporter for tissue-specific expression. Specifically, it was sought to develop iPSC-derived cardiomyocytes engineered to express tissue specific autobioluminescence.

First, the autobioluminescent output was linked to the TNNT2 promoter to enable cardiac tissue specific expression. The TNNT2 promoter is established as a cardiomyocyte specific promoter capable of driving a variety of optical imaging and resistance markers.

Next, wild type iPSCs and iPSC-derived cardiomyocytes were transiently transfected with CBA-luxCDEfrp and either CBA-luxAB (constitutive) or TNNT2-luxAB (cardiac specific) at 20:1 ratio. The 20:1 ratio was observed in order to adhere to the unexpected optimal ratio of luxAB to luxCDEfrp, as detailed above. After twenty-four (24) hours, autobioluminescent output was measured.

Figure 17:
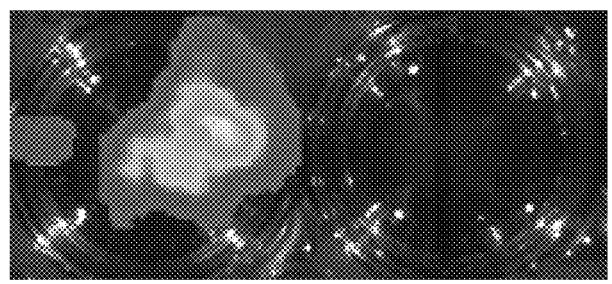
FIG. 17. iPSC-derived cardiomyocytes expressing tissue specific autobioluminescence according to an embodiment of the disclosure. Wild type iPSCs and iPSC derived cardiomyocytes were transiently transfected with CBA-luxCDEF and either CBA-luxAB (constitutive) or TNNT2-luxAB (cardiac specific) at 20:1 and measured 24 hours later for autobioluminescent output. Autobioluminescence was observed in both wild type iPSCs and iPSC-derived cardiomyocytes co-expressing CBA-luxCDEfrp and CBA-luxAB (constitutive). Moreover, when cardiac specific TNNT2-luxAB was co-expressed with CBA-luxCDEfrp in transiently transfected wild type iPSC-derived cardiomyocytes, autobioluminescent expression was observed; however, no such autobioluminescent expression was observed when transfected into iPSCs.
Figure 17:
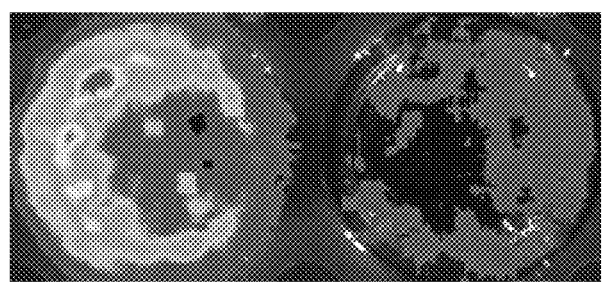

Ultimately, autobioluminescence was observed in both wild type iPSCs and iPSC-derived cardiomyocytes co-expressing CBA-luxCDEfrp and CBA-luxAB (constitutive) (FIG. 17). Moreover, when TNNT2 was cloned upstream of luxAB and co-expressed with CBA-luxCDEfrp in transiently transfected wild type iPSC-derived cardiomyocytes, autobioluminescent expression was observed; however no such autobioluminescent expression was observed when transfected into iPSCs, as illustrated in FIG. 17. The TNNT2-driven autobioluminescence was approximately 2.5 (±0.5) times less than the CBA-driven autobioluminescence, suggesting the TNNT2 promoter is not activated to same extent as CBA in cardiomyocytes. Nonetheless, these data still demonstrate tissue specific autobioluminescent expression.

Working Example 7—Differentiation Reporting Using the Tissue-Specific Autobioluminescent Construct To determine whether tissue specific autobioluminescent constructs are capable of differentiation reporting, a version of the cassette was constructed that used a two-module synthetic amplification circuit to control autobioluminescent expression. The first module uses the human adipose-tissue-specific promoter, hAP2, to control the expression of a Gal4ff fusion gene consisting of the Gal4 DNA binding domain and two transcriptional motifs of the herpes simplex virus VP16 transcription factor. The second module harbors the luxCDABEF genes under the regulation of five tandem repeats of the yeast upstream activating sequence (UAS) and a minimal promoter. This two-module circuit was transfected into mesenchymal stem cells (MSCs) and stably selected. Cells expressing this version of the cassette should be capable of self-initiating autobioluminescent production only upon differentiation into adipose tissue.

To verify this, the parental MSC line was differentiated into adipocyte, chondrocyte, and osteocyte lineages and autobioluminescent output was measured both before and after differentiation. The measured autobioluminescent signal from the parental MSC line before differentiation was similar to background light detection (FIG. 18). Following differentiation, autobioluminescent production from the target adipocyte cell line was 5.59× greater than background, indicating initiation of the autobioluminescent phenotype. No autobioluminescent signal was present from the chondrocyte or osteocyte differentiated cell line (1.31× and 1.35× relative to background, respectively) (FIG. 18).

These data demonstrate using autobioluminescence to track targeted MSC to adipocyte differentiation and its use to indicate differentiation tracking without the need to perturb the samples under study.

Working Example 8—IPSC-luxABICDEF Derived Cardiomyocytes Maintain the Autobioluminescent Phenotype Experimentation was undertaken to determine whether specialized cells differentiated from the iPSC-luxAB/CDEF line preserve the autobioluminescent phenotype. Small molecule targeted cardiac differentiation of the iPSC-luxAB/CDEF line was performed via temporal modulation of Wnt signaling using CHIR99021 and IWP-2/4 as described previously (pubmed ID 22645348). This resulted in the production of autobioluminescent CBA-driven luxAB/CDEF cardiomyocytes (FIG. 19A). This lineage was denoted as CM-luxAB/CDEF.

Then, the normalized average autobioluminescent radiance (p/s/cm²/sr) per plated cell was determined for both iPSC-luxAB/CDEF and CM-luxAB/CDEF. As illustrated in FIG. 19B, the autobioluminescent iPSC-luxAB/CDEF derived cardiomyocytes were observed to produce approximately similar levels of autobioluminescent light as the iPSC-luxAB/CDEF line.

These results show that iPSC-luxAB/CDEF line was differentiated into cardiomyocytes that preserve the autobioluminescent phenotype. The data demonstrates that the autobioluminescent phenotype is not radically altered by the change in cell type. This data demonstrates that the lux operon can be used to produce reagent-free bioluminescence in iPSC-derived cardiomyocytes.

Working Example 9—Continuous Cardiotoxicity Monitoring with Autobioluminescent iPSC-Derived Cardiomyocytes To address the limitations of current cardiotoxicity screening (e.g., high costs, need for destructive end-point style assays, etc.), experimentation was undertaken to verify the utility of the CBA-driven luxAB/CDEF cardiomyocytes to report cardiotoxicity in response to doxorubicin and, relatedly, the use of said cells to provide real time, continuous cardiotoxicity monitoring in response to doxorubicin treatment over an extended time.

First, it was assessed whether the CM-luxAB/CDEF line can report cardiotoxicity in response to doxorubicin, a known cardiotoxic compound. The CM-luxAB/CDEF line was treated with a range of doxorubicin concentrations, and the autobioluminescent output was measured after twenty-four (24) hours of treatment. The percent change in average radiance (p/s/cm²/sr) relative to control was plotted against the corresponding doxorubicin (uM) treatment. The results demonstrated that the autobioluminescence from the cardiomyocytes exhibited a decrease in strength correlated with dose (FIG. 19C). These data yielded an $IC_{50}$ of 0.29 uM doxorubicin that is similar to that reported previously for iPSC-derived cardiomyocytes exposed to doxorubicin (PubmedID 28202772). Thus, the CBA-driven luxAB/CDEF cardiomyocytes faithfully reported cardiotoxicity in response to doxorubicin Second, it was assessed whether the CM-luxAB/CDEF line can provide real time, continuous cardiotoxicity monitoring in response to doxorubicin treatment over an extended time. CM-luxAB/CDEF cardiomyocytes were continuously monitored for thirty hours, with autobioluminescence being measured every ten (10) minutes. For the first five (5) hours, autobioluminescence was monitored in the absence of treatment to establish a baseline signal. Then, at five (5) hours, a subset of the cardiomyocytes were challenged with increasing doses of the cardiotoxicant doxorubicin (white arrow in FIG. 20A). Autobioluminescent output was continuously measured for the next 25 hours.

Figure 20A:
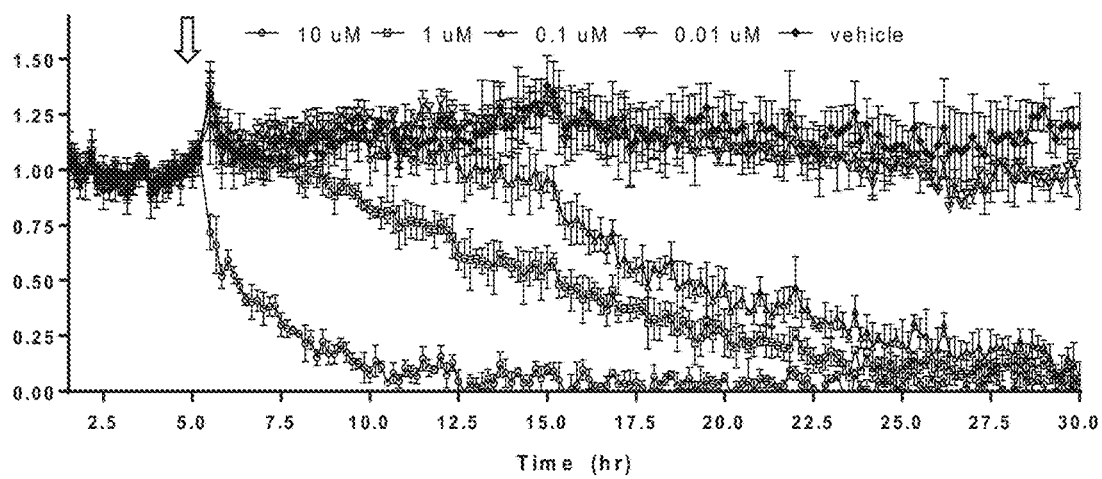
FIGS. 20A-20C. Autobioluminescent cardiomyocytes enabled continuous doxorubicin toxicity monitoring over 30 hours.
Figure 20B:
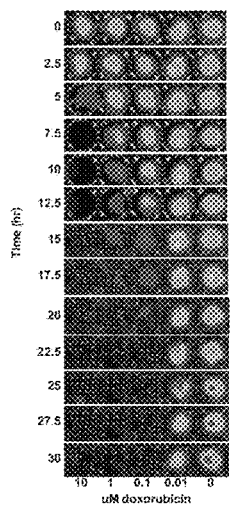

The data showed that increasing concentrations of doxorubicin resulted in decreasing autobioluminescent output, which was revealed in real time (FIG. 20A). The continuous data show a clear trend whereby higher concentrations of doxorubicin exert toxic effects faster than lower doses despite the different concentrations resolving to approximately the same level of cellular autobioluminescent output after thirty (30) hours. This trend is clear even when two and a half (2.5) hour intervals over the same time period are examined (FIG. 20B).

Figure 20C:
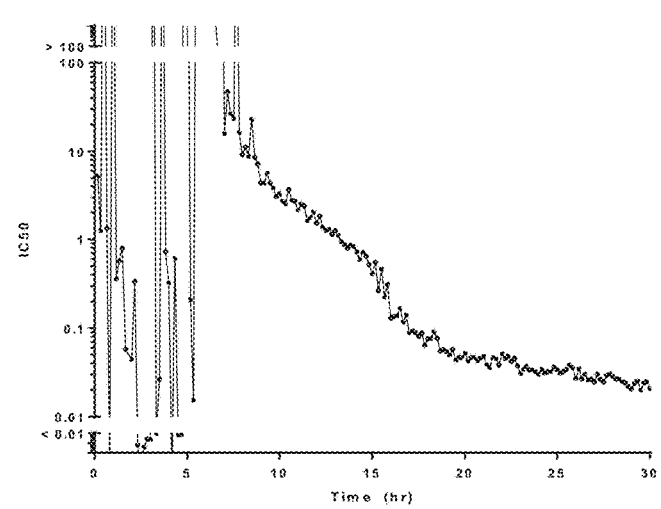

The $IC_{50}$ values were calculated over the experimental time course and plotted against time. A clear reduction in $IC_{50}$ concentration was observed over the time course (FIG. 20C). Such a result is expected for a known cardiotoxic compound like doxorubicin; however, the kinetic $IC_{50}$ values provide context for any single time point measurement. Accordingly, this data enables determination of when a compound's effect, as measured by its $IC_{50}$, stabilizes, thus enabling a more confident assessment of toxicity. For doxorubicin, this appeared to occur near 30 hours of exposure. This data demonstrates that continuously autobioluminescent iPSC-derived cardiomyocytes can offer real-time, long-term toxicity tracking.

LISTING OF EXEMPLARY EMBODIMENTS

Embodiment 1

A stem cell comprising an autobioluminescent phenotype comprising a luminescent signal in the absence of an exogenous luminescent stimulator.

Embodiment 2

The stem cell of embodiment 1, further comprising luxA, luxB, luxC, luxD, luxE, and flavin reductase.

Embodiment 3

1. The stem cell of any one of embodiments 1-2, further comprising nucleic acids encoding each of luxA, luxB, luxC, luxD, luxE, and flavin reductase.

Embodiment 4

1. The stem cell of any one of embodiments 1-3, wherein the luminescent signal is constitutively emitted.

Embodiment 5

1. The stem cell of embodiment 4, wherein at least one of the luxA nucleic acid, the luxB nucleic acid, the luxC nucleic acid, the luxD nucleic acid, the luxE nucleic acid, and the flavin reductase nucleic acid is operatively linked to at least one constitutive promoter.

Embodiment 6

The stem cell of embodiment 5, wherein the luxA nucleic acid, the luxB nucleic acid, the luxC nucleic acid, the luxD nucleic acid, the luxE nucleic acid, and the flavin reductase nucleic acid are each operatively linked to a constitutive promoter.

Embodiment 7

The stem cell of embodiment 5, wherein the luxA nucleic acid and the luxB nucleic acid are operatively linked to a first constitutive promoter.

Embodiment 8

The stem cell of embodiment 7, wherein the luxC nucleic acid, the luxD nucleic acid, the luxE nucleic acid, and the flavin reductase nucleic acid are operatively linked to a second constitutive promoter.

Embodiment 9

A kit for producing a stem cell having an autonomous luminescent phenotype, comprising:
at least one vector comprising at least one of a luxA nucleic acid, a luxB nucleic acid, a luxC nucleic acid, a luxD nucleic acid, a luxE nucleic acid, nucleic acid, and a flavin-reductase nucleic acid.

Embodiment 10

A method for producing a stem cell having autonomous and constitutive luminescence, comprising:
providing a stem cell; and
transfecting the stem cell with at least one vector comprising at least one of a luxA nucleic acid, a luxB nucleic acid, a luxC nucleic acid, a luxD nucleic acid, a luxE nucleic acid, nucleic acid, and a flavin-reductase nucleic acid.

Embodiment 11

Any one of embodiments 9 or 10, wherein the at least one vector comprises:
a first vector comprising a luxA nucleic acid;
a second vector comprising a luxB nucleic acid;
a third vector comprising a luxC nucleic acid;
a fourth vector comprising a luxD nucleic acid;
a fifth vector comprising a luxE nucleic acid; and
a sixth vector comprising a flavin-reductase nucleic acid, wherein one or more of the luxA nucleic acid, the luxB nucleic acid, the luxC nucleic acid, the luxD nucleic acid, the luxE nucleic acid, and the flavin-reductase nucleic acid are operatively linked to a constitutive promoter.

Embodiment 12

Any one of embodiments 9 or 10, wherein the at least one vector comprises:
a first vector comprising:
a luxA nucleic acid and a luxB nucleic acid, wherein the luxA nucleic acid and the luxB nucleic acid are operatively linked to a first constitutive promoter; and
a second vector comprising:
a luxC nucleic acid, a luxD nucleic acid, a luxE nucleic acid, nucleic acid, and a flavin-reductase nucleic acid, and wherein the luxC nucleic acid, luxD nucleic acid, luxE nucleic acid, and flavin reductase nucleic acid are operatively linked to a second constitutive promoter.

Embodiment 13

The embodiment of any one of embodiments 10-12, wherein after the stem cell is transfected with the at least one vector, the stem cell expresses luxA, luxB, luxC, luxD, luxE, and flavin reductase.

Embodiment 14

A method of real-time monitoring of cell population size of at least one stem cell, comprising:
engineering the at least one stem cell to produce a constitutive luminescent signal;
measuring the constitutive luminescent signal emitted from the at least one stem; and
assessing the cell population size of the at least one stem cell based on the measured constitutive luminescent signal.

Embodiment 15

The method of embodiment 14, further comprising tracking the cell population size over two or more points in time.

Embodiment 16

A method of real-time monitoring of cell viability of at least one stem cell, comprising:
engineering the at least one stem cell to produce a constitutive luminescent signal;
measuring the constitutive luminescent signal emitted from the at least one stem cell; and
assessing the cell viability of the at least one stem cell based on the measured constitutive luminescent signal.

Embodiment 17

The method of embodiment 16, further comprising tracking the cell viability of the at least one stem cell over two or more points in time.

Embodiment 18

The method of any one of embodiments 14-17, wherein the measurement of the constitutive luminescent signal emitted from the at least one stem cell correlates with the cell viability of the at least one stem cell.

Embodiment 19

A method for measuring an effect of an agent on at least one stem cell, comprising:
engineering the at least one stem cell to produce a constitutive luminescent signal;
contacting the at least one stem cell with an agent;
measuring the constitutive luminescent signal emitted from the at least one stem cell after the at least one stem cell is contacted with the agent; and
determining the effect of the agent based on the measured constitutive luminescent signal.

Embodiment 20

The method of embodiment 19, further comprising tracking the effect of the agent over two or more points in time.

Embodiment 21

The method of any one of embodiments 19 or 20, wherein when the at least one stem cell ceases production of a constitutive luminescent signal, determining that the agent is fatal to the at least one stem cell.

Embodiment 22

The method of any one of embodiments 14-21, further comprising comparing the measurement of the constitutive luminescent signal emitted from the at least one stem cell to a constitutive luminescent signal emitted from a control population.

Embodiment 23

The methods of embodiment 22, wherein a decrease in the measured constitutive luminescent signal emitted from the at least one stem cell relative to the constitutive luminescent signal emitted from the control population is indicative of a negative change in cell viability of the at least one stem cell.

Embodiment 24

The method of embodiment 23, determining that the effect of the agent is cytotoxic.

Embodiment 25

The method of embodiment 22, wherein an increase in the measured constitutive luminescent signal emitted from the at least one stem cell relative to the constitutive luminescent signal emitted from the control population is indicative of a positive change in cell viability of the at least one stem cell.

Embodiment 26

The method of embodiment 25, determining that the effect of the agent is therapeutic.

Embodiment 27

The method of any one of embodiments 19-26, wherein the agent is assessed for drug discovery.

Embodiment 28

Any one of the methods of any one of the embodiments 14-27, wherein the method is performed in high-throughput.

Embodiment 29

A method for reagent-free in vivo imaging of at least one stem cell, comprising:
engineering the at least one stem cell to produce a constitutive luminescent signal in the absence of an exogenously added substrate;
injecting the at least one stem cell into an organism; and
imaging the constitutive luminescent signal emitted from the at least one stem cell in the organism.

Embodiment 30

The method of embodiment 29, further comprising measuring the constitutive luminescent signal, and determining a total number of the at least one stem cell present in vivo based on the measured constitutive luminescent signal.

Embodiment 31

The method of any one of embodiments 29 or 30, wherein the organism comprises an animal, and wherein the at least one stem cell is injected intravenously, intradermally, or subcutaneously in the organism.

Embodiment 32

The method of embodiment 31, further comprising, after the at least one stem cell is injected into the animal, tracking movement of the at least one stem cell within the animal.

Embodiment 33

The method of any one of embodiments 29-32, wherein the exogenously added substrate comprises an aldehyde functional group.

Embodiment 34

The method of any one of embodiments 14-33, wherein the at least one stem cell comprises:
a first vector comprising:
a luxA nucleic acid and a luxB nucleic acid, wherein the luxA nucleic acid and the luxB nucleic acid are operatively linked to a first constitutive promoter, and a second vector comprising:
a luxC nucleic acid, a luxD nucleic acid, a luxE nucleic acid, and a flavin reductase nucleic acid, and wherein the luxC nucleic acid, luxD nucleic acid, luxE nucleic acid, and flavin reductase nucleic acid are operatively linked to a second constitutive promoter.

Embodiment 35

The method of any one of embodiments 14-33, wherein the at least one stem cell comprises:
a first vector comprising a luxA nucleic acid;
a second vector comprising a luxB nucleic acid;
a third vector comprising a luxC nucleic acid;
a fourth vector comprising a luxD nucleic acid;
a fifth vector comprising a luxE nucleic acid; and
a sixth vector comprising a flavin-reductase nucleic acid, wherein one or more of the luxA nucleic acid, the luxB nucleic acid, the luxC nucleic acid, the luxD nucleic acid, the luxE nucleic acid, and the flavin-reductase nucleic acid are operatively linked to a constitutive promoter.

Embodiment 36

The stem cell of any one of embodiments 1-3, wherein the luminescent signal is tissue-specific.

Embodiment 37

The stem cell of embodiment 36, comprising: at least one vector comprising a luxA nucleic acid, a luxB nucleic acid, a luxC nucleic acid, a luxD nucleic acid, a luxE nucleic acid, nucleic acid, and a flavin-reductase nucleic acid, wherein at least one of the nucleic acids is operatively linked to a tissue-specific promoter.

Embodiment 38

A method for producing a stem cell comprising an autonomous luminescent phenotype comprising a tissue-specific signal, comprising:
providing a stem cell; and
transfecting the stem cell with at least one vector comprising at least one of a luxA nucleic acid, a luxB nucleic acid, a luxC nucleic acid, a luxD nucleic acid, a luxE nucleic acid, nucleic acid, and a flavin-reductase nucleic acid, wherein at least one of the nucleic acids is operatively linked to a tissue-specific promoter.

Embodiment 39

The stem cell of any one of embodiments 36-38, wherein if the stem cell is differentiated to a tissue cell expressing the tissue-specific promoter, the tissue cell expresses luxA, luxB, luxC, luxD, luxE, and flavin reductase and emits an autonomous luminescent signal.

Embodiment 40

A method of real-time differentiation reporting using at least one stem cell comprising an autonomous luminescent phenotype comprising a tissue-specific signal, comprising:
providing the least one stem cell comprising:
at least one vector comprising at least one of a luxA nucleic acid, a luxB nucleic acid, a luxC nucleic acid, a luxD nucleic acid, a luxE nucleic acid, nucleic acid, and a flavin-reductase nucleic acid, wherein at least one of the nucleic acids is operatively linked to a tissue-specific promoter, and wherein if the at least one stem cell is differentiated to at least one tissue cell in which the tissue-specific promoter is expressed, the at least one tissue cell emits a luminescent signal; and
when the luminescent signal is emitted, measuring the luminescent signal emitted from the tissue cell to track differentiation of the at least one stem cell to the at least one tissue cell.

Embodiment 41

The method of embodiment 40, further comprising tracking the differentiation of the at least one stem cell to the at least one tissue cell over two or more points in time.

Embodiment 42

The method of any one of embodiments 40 or 41, wherein an emission of the luminescent signal reports an onset of the differentiation of the at least one stem cell to the at least one tissue cell.

Embodiment 43

The method of any one of embodiments 40-42, further comprising assessing a total number of the at least one tissue cell based on the measurement of the luminescent signal.

Embodiment 44

The method of any one of embodiments 40-43, further comprising determining the at least one stem cell differentiated to the at least one tissue cell based on the measurement of the luminescent signal.

Embodiment 45

A kit for producing a stem cell comprising an autonomous luminescent phenotype comprising a tissue-specific signal, comprising:
at least one vector comprising at least one of a luxA nucleic acid, a luxB nucleic acid, a luxC nucleic acid, a luxD nucleic acid, a luxE nucleic acid, nucleic acid, and a flavin-reductase nucleic acid, wherein at least one of the nucleic acids is operatively linked to a tissue-specific promoter.

Embodiment 46

The stem cell or kit of any one of embodiments 37-45, wherein the at least one vector comprises:
a first vector comprising:
a luxA nucleic acid and a luxB nucleic acid, wherein the luxA nucleic acid and the luxB nucleic acid are operatively linked to a tissue-specific promoter; and
a second vector comprising:
a luxC nucleic acid, a luxD nucleic acid, a luxE nucleic acid, nucleic acid, and a flavin-reductase nucleic acid, wherein the luxC nucleic acid, luxD nucleic acid, luxE nucleic acid, and flavin reductase nucleic acid are operatively linked to a first constitutive promoter.

Embodiment 47

The stem cell or kit of any one of embodiments 37-45, wherein the at least one vector comprises:
a first vector comprising a luxA nucleic acid;
a second vector comprising a luxB nucleic acid;
a third vector comprising a luxC nucleic acid;
a fourth vector comprising a luxD nucleic acid;
a fifth vector comprising a luxE nucleic acid; and
a sixth vector comprising a flavin-reductase nucleic acid,
wherein one or more of the luxA nucleic acid, the luxB nucleic acid, the luxC nucleic acid, the luxD nucleic acid, the luxE nucleic acid, and the flavin-reductase nucleic acid are operatively linked to a tissue-specific promoter.

Embodiment 48

Any one of embodiments 37-47, wherein the tissue-specific promoter comprises a TNNT2 promoter.

Embodiment 49

Any one of embodiments 39-48, wherein the tissue cell or the at least one tissue cell comprises a cardiomyocyte.

Embodiment 50

Any one of embodiments 11-49, wherein a total amount of transfected vector comprising the luxC nucleic acid, the luxD nucleic acid, the luxE nucleic acid, and the flavin-reductase nucleic is present at an amount of from ten to forty times greater than a total amount of transfected vector comprising the luxA nucleic acid and the luxB nucleic acid.

Embodiment 51

Any one of embodiments 11-49, wherein a total amount of transfected vector comprising the luxC nucleic acid, the luxD nucleic acid, the luxE nucleic acid, and the flavin-reductase nucleic is present at an amount of from twenty to thirty times greater than a total amount of transfected vector comprising the luxA nucleic acid and the luxB nucleic acid.

Embodiment 52

Any one of embodiments 11-49, wherein a total amount of vector comprising the luxC nucleic acid, the luxD nucleic acid, the luxE nucleic acid, and the flavin-reductase nucleic is transfected at an amount of from ten to forty times greater than a total amount of vector comprising the luxA nucleic acid and the luxB nucleic acid.

Embodiment 53

Any one of embodiments 11-49, wherein a total amount of vector comprising the luxC nucleic acid, the luxD nucleic acid, the luxE nucleic acid, and the flavin-reductase nucleic acid are transfected at an amount of from twenty to thirty times greater than a total amount of vector comprising the luxA nucleic acid and the luxB nucleic acid.

Embodiment 54

The stem cell of any one of embodiments 1-3, wherein the luminescent signal is responsive to an analyte.

Embodiment 55

The stem cell of embodiment 54, comprising: a luxA nucleic acid, a luxB nucleic acid, a luxC nucleic acid, a luxD nucleic acid, a luxE nucleic acid, and a flavin reductase nucleic acid, and wherein at least one of the luxA nucleic acid, the luxB nucleic acid, the luxC nucleic acid, the luxD nucleic acid, the luxE nucleic acid, and the flavin reductase nucleic acid are operatively linked to at least one analyte-responsive response element.

Embodiment 56

The stem cell of embodiment 55, wherein the stem cell further comprises at least one analyte-responsive reverse transactivator that, when exposed to the analyte, activates the at least one analyte-responsive response element, wherein activation of the at least one analyte-responsive response element causes transcription of the at least one of the luxA nucleic acid, the luxB nucleic acid, the luxC nucleic acid, the luxD nucleic acid, the luxE nucleic acid, and the flavin reductase nucleic acid that is operatively linked to at least one analyte-responsive response element.

Embodiment 57

The stem cell of embodiment 55, wherein the stem cell further comprises at least one analyte-responsive transactivator that, when exposed to the analyte, does not activate the at least one analyte-responsive response element, wherein lack of activation of the at least one analyte-responsive response element results in no transcription of the at least one of the luxA nucleic acid, the luxB nucleic acid, the luxC nucleic acid, the luxD nucleic acid, the luxE nucleic acid, and the flavin reductase nucleic acid that is operatively linked to at least one analyte-responsive response element.

Embodiment 58

A method of constructing a stem cell configured to emit an autonomous inducible luminescent signal in the presence of an analyte, comprising:
   providing a stem cell;
   co-transfecting the stem with at least one vector comprising a luxA nucleic acid, a luxB nucleic acid, a luxC nucleic acid, a luxD nucleic acid, a luxE nucleic acid, and a flavin reductase nucleic acid, and wherein at least one of the luxA nucleic acid, the luxB nucleic acid, the luxC nucleic acid, the luxD nucleic acid, the luxE nucleic acid, and the flavin reductase nucleic acid are operatively linked to at least one analyte-responsive response element; and
   co-transfecting the stem cell with a second vector comprising at least one analyte-responsive reverse transactivator that that, when exposed to the analyte, activates the at least one analyte-responsive response element,
   wherein activation of the at least one analyte-responsive response element initiates transcription of the at least one of the luxA nucleic acid, the luxB nucleic acid, the luxC nucleic acid, the luxD nucleic acid, the luxE nucleic acid, and the flavin reductase nucleic acid that is operatively linked to the at least one analyte-responsive response element.

Embodiment 59

A method of constructing a stem cell configured to emit an autonomous repressible luminescent signal in the presence of an analyte, comprising:
   providing a stem cell;
   co-transfecting the stem cell with at least one vector comprising a luxA nucleic acid, a luxB nucleic acid, a luxC nucleic acid, a luxD nucleic acid, a luxE nucleic acid, and a flavin reductase nucleic acid, and wherein at least one of the luxA nucleic acid, the luxB nucleic acid, the luxC nucleic acid, the luxD nucleic acid, the luxE nucleic acid, and the flavin reductase nucleic acid are operatively linked to at least one analyte-responsive response element; and
   co-transfecting the stem cell with a second vector comprising at least one analyte-responsive transactivator that, when exposed to the analyte, does not activate the at least one analyte-responsive response element,
   wherein no activation of the at least one analyte-responsive response element prevents transcription of the at least one of the luxA nucleic acid, the luxB nucleic acid, the luxC nucleic acid, the luxD nucleic acid, the luxE nucleic acid, and the flavin reductase nucleic acid that is operatively linked to the at least one analyte-responsive response element.

Embodiment 60

A method of monitoring gene expression in at least one stem cell, comprising:
producing at least one of the stem cell of any one of embodiments 54, 55, 56, or 57;
contacting the at least one stem cell with the analyte; and
measuring the luminescent signal emitted from the at least one stem cell after contacting the at least one stem cell with the analyte to monitor expression of the luxA nucleic acid, the luxB nucleic acid, the luxC nucleic acid, the luxD nucleic acid, the luxE nucleic acid, and the flavin reductase nucleic acid.

Embodiment 61

The method of embodiment 60, further comprising measuring the luminescent signal emitted from the at least one stem cell over two or more points in time.

Embodiment 62

The method of any one of embodiments 60 or 61, further comprising assessing gene expression by comparing the measurement of the luminescent signal emitted from the at least one stem to a luminescent signal emitted from a control population.

Embodiment 63

A method of determining a presence of an analyte in a sample, comprising:
producing at least one of the stem cell of any one of embodiments 54, 55, 56, or 57;
contacting the at least one stem cell with the sample;
measuring the luminescent signal emitted from the at least one stem cell after contacting the at least one stem cell with the analyte to monitor expression of the luxA nucleic acid, the luxB nucleic acid, the luxC nucleic acid, the luxD nucleic acid, the luxE nucleic acid, and the flavin reductase nucleic acid; and assessing the presence of the analyte in the sample based on the measurement of the luminescent signal.

Embodiment 64

The method of embodiment 63, further comprising comparing the measurement of the luminescent signal emitted from the at least one stem to a luminescent signal emitted from a control population.

Embodiment 65

A kit for producing a stem cell emitting an autonomous luminescent signal inducible by an analyte, comprising:
at least one vector comprising a luxA nucleic acid, a luxB nucleic acid, a luxC nucleic acid, a luxD nucleic acid, a luxE nucleic acid, and a flavin reductase nucleic acid, and wherein at least one of the luxA nucleic acid, the luxB nucleic acid, the luxC nucleic acid, the luxD nucleic acid, the luxE nucleic acid, and the flavin reductase nucleic acid are operatively linked to at least one analyte-responsive response element; and
a second vector comprising at least one analyte-responsive reverse transactivator that, when exposed to the analyte, activates the at least one analyte-responsive response element.

Embodiment 66

A kit for producing a stem cell emitting an autonomous luminescent signal repressible by an analyte, comprising:
at least one vector comprising a luxA nucleic acid, a luxB nucleic acid, a luxC nucleic acid, a luxD nucleic acid, a luxE nucleic acid, and a flavin reductase nucleic acid, and wherein at least one of the luxA nucleic acid, the luxB nucleic acid, the luxC nucleic acid, the luxD nucleic acid, the luxE nucleic acid, and the flavin reductase nucleic acid are operatively linked to at least one analyte-responsive response element; and
a second vector comprising at least one analyte-responsive transactivator that, when exposed to the analyte, does not activate the at least one analyte-responsive response element.

Embodiment 67

Any one of embodiments 55-66, wherein the at least one analyte-responsive response element comprises a tetracycline response element, preferably wherein the analyte comprises tetracycline or an analog of tetracycline.

Embodiment 68

Any one of embodiments 55-67, wherein the at least one analyte-responsive transactivator or the at least one analyte-responsive reverse transactivator is operatively linked to a constitutive promoter, preferably wherein the constitutive promoter is a chicken beta-actin promoter.

Embodiment 69

Any one of embodiments 55-68, wherein the at least one of the luxA nucleic acid, the luxB nucleic acid, the luxC nucleic acid, the luxD nucleic acid, the luxE nucleic acid, and the flavin reductase nucleic acid that is not operatively linked to at least one analyte-responsive response element is operatively linked to a constitutive promoter.

Embodiment 70

A stem cell-derived autonomously luminescent cell, comprising:
an autonomously luminescent eukaryotic cell differentiated from an autonomously luminescent stem cell, wherein the differentiated autonomously luminescent eukaryotic cell and the autonomously luminescent stem cell both express a constitutive luminescent signal in the absence of an exogenous luminescent stimulator.

Embodiment 71

A method for producing a stem cell-derived autonomously luminescent cell from an autonomously luminescent stem cell, comprising:
constructing an autonomously luminescent stem cell, and
differentiating the autonomously luminescent stem cell into the stem cell-derived autonomously luminescent cell, wherein the stem cell-derived autonomously luminescent cell emits a luminescent signal in the absence of an exogenous luminescent stimulator.

Embodiment 72

The method of embodiment 71, wherein the differentiating is performed by small molecule method.

Embodiment 73

A method of real-time monitoring of cell viability of at least one stem cell-derived autonomously luminescent cell, comprising:
providing at least one stem cell-derived autonomously luminescent cell;
measuring the constitutive luminescent signal emitted from the at least one stem cell-derived autonomously luminescent cell; and
assessing the cell viability of the at least one stem cell-derived autonomously luminescent cell based on the measured constitutive luminescent signal.

Embodiment 74

The method of embodiment 73, further comprising tracking the cell viability of the at least one stem cell-derived autonomously luminescent cell over two or more points in time.

Embodiment 75

The method of any one of embodiments 73 or 74, wherein the measurement of the constitutive luminescent signal correlates with the cell viability of the at least one stem cell-derived autonomously luminescent cell.

Embodiment 76

A method for determining an effect of an agent in at least one stem cell-derived autonomously luminescent cell, comprising:
engineering the at least one stem cell-derived autonomously luminescent cell to produce a constitutive luminescent signal;
contacting the at least one stem cell-derived autonomously luminescent cell with an agent;
measuring the constitutive luminescent signal emitted from the at least one stem cell-derived autonomously luminescent cell after the at least one stem cell-derived autonomously luminescent cell is exposed to the agent; and
determining the effect of the agent based on the measured constitutive luminescent signal.

Embodiment 77

The method of embodiment 76, further comprising tracking the effect of the agent over two or more points in time.

Embodiment 78

The method of embodiment 77, further comprising determining a time point at which the effect of the agent stabilizes.

Embodiment 79

The method of any one of embodiments 76-78, wherein when the at least one stem cell-derived autonomously luminescent cell ceases production of a constitutive luminescent signal, determining that the agent is fatal to the at least one stem cell-derived autonomously luminescent cell.

Embodiment 80

The method of any one of embodiments 73-79, further comprising comparing the measurement of the constitutive luminescent signal emitted from the at least one stem cell-derived autonomously luminescent cell to the constitutive luminescent signal emitted from a control population.

Embodiment 81

The method of embodiment 80, wherein a decrease in the measured constitutive luminescent signal emitted from the at least one stem cell-derived autonomously luminescent cell relative to the constitutive luminescent signal emitted from the control population is indicative of a negative change in the cell viability of the at least one stem cell-derived autonomously luminescent cell resulting from exposure to the agent.

Embodiment 82

The method of embodiment 81, determining that the effect of the agent is cytotoxic.

Embodiment 83

The method of embodiment 80, wherein an increase in the measured constitutive luminescent signal emitted from the at least one stem cell-derived autonomously luminescent cell relative to the constitutive luminescent signal emitted from the control population is indicative of a positive change in the cell viability of the at least one stem cell-derived autonomously luminescent cell resulting from exposure to the agent.

Embodiment 84

The method of embodiment 83, determining that the effect of the agent is therapeutic.

Embodiment 85

Any one of embodiments 70-83, wherein the autonomously luminescent stem cell comprises: at least one vector comprising at least one of a luxA nucleic acid, a luxB nucleic acid, a luxC nucleic acid, a luxD nucleic acid, a luxE nucleic acid, nucleic acid, and a flavin-reductase nucleic acid, wherein the luxA nucleic acid, a luxB nucleic acid, luxC nucleic acid, luxD nucleic acid, luxE nucleic acid, and flavin-reductase nucleic acid are operatively linked to at least one constitutive promoter, and wherein the autonomously luminescent stem cell expresses luxA, luxB, luxC, luxD, luxE, and flavin reductase.

Embodiment 86

The preceding embodiment 85, wherein the at least one vector comprises:
a first vector comprising:
a luxA nucleic acid and a luxB nucleic acid, wherein the luxA nucleic acid and the luxB nucleic acid are operatively linked to a first constitutive promoter, and a second vector comprising:
a luxC nucleic acid, a luxD nucleic acid, a luxE nucleic acid, and a flavin reductase nucleic acid, and wherein the luxC nucleic acid, luxD nucleic acid, luxE nucleic acid, and flavin reductase nucleic acid are operatively linked to a second constitutive promoter.

Embodiment 87

The preceding embodiment 85, wherein the at least one vector comprises:
a first vector comprising a luxA nucleic acid;
a second vector comprising a luxB nucleic acid;
a third vector comprising a luxC nucleic acid;
a fourth vector comprising a luxD nucleic acid;
a fifth vector comprising a luxE nucleic acid; and
a sixth vector comprising a flavin-reductase nucleic acid,
wherein one or more of the luxA nucleic acid, the luxB nucleic acid, the luxC nucleic acid, the luxD nucleic acid, the luxE nucleic acid, and the flavin-reductase nucleic acid are operatively linked to a constitutive promoter.

Embodiment 88

Any one of the preceding embodiments, wherein the stem cell-derived autonomously luminescent cell expresses luxA, luxB, luxC, luxD, luxE, and flavin reductase, such that the stem cell-derived autonomously luminescent cell luminesces in the absence of an exogenous luminescent stimulator.

Embodiment 89

Any one of the preceding embodiments, wherein a combined production level of luxC, luxD, luxE, and flavin reductase ranges from ten to forty times greater than a combined production level of luxA and luxB.

Embodiment 90

Any one of the preceding embodiments, wherein a combined production level of luxC, luxD, luxE, and flavin reductase ranges from twenty to thirty times greater than a combined production level of luxA and luxB.

Embodiment 91

Any one of the preceding embodiments, wherein one or more of the nucleic acids encoding each of luxA, luxB, luxC, luxD, luxE has a greater than 80% sequence identity with the corresponding nucleic acid in *Photorhabdus luminescens*.

Embodiment 92

Any one of the preceding embodiments, wherein one or more of the nucleic acids encoding each of luxA, luxB, luxC, luxD, luxE has a 100% sequence identity with the corresponding nucleic acid in *Photorhabdus luminescens*.

Embodiment 93

Any one of the preceding embodiments, wherein the stem cell emits the luminescent signal through transcription of the luxA nucleic acid, the luxB nucleic acid, the luxC nucleic acid, the luxD nucleic acid, the luxE nucleic acid, and the flavin reductase nucleic acid.

Embodiment 94

Any one of the preceding embodiments, wherein transcription levels of the luxC nucleic acid, the luxD nucleic acid, the luxE nucleic acid, and the flavin reductase nucleic acid range from ten to forty times greater than transcription levels of the luxA nucleic acid and the luxB nucleic acid.

Embodiment 95

Any one of the preceding embodiments, wherein transcription levels of the luxC nucleic acid, the luxD nucleic acid, the luxE nucleic acid, and the flavin reductase nucleic acid range from twenty to thirty times greater than transcription levels of the luxA nucleic acid and the luxB nucleic acid.

Embodiment 96

Any one of the preceding embodiments, wherein the nucleic acids encoding each of luxC, luxD, luxE, and flavin reductase are present in a combined level of from ten times to forty times a combined level of nucleic acids encoding luxA and luxB.

Embodiment 97

Any one of the preceding embodiments, wherein the nucleic acids encoding each of luxC, luxD, luxE, and flavin reductase are present in a combined level of from twenty times to thirty times a combined level of nucleic acids encoding luxA and luxB.

Embodiment 98

Any one of the preceding embodiments, wherein the stem cell or the at least one stem cell further comprises luxA, luxB, luxC, luxD, luxE, and flavin reductase.

Embodiment 99

Any one of the preceding embodiments, wherein the stem cell or the at least one stem cell expresses luxA, luxB, luxC, luxD, luxE, and flavin reductase.

Embodiment 100

Any one of the preceding embodiments, wherein a combined production level of luxC, luxD, luxE, and flavin reductase ranges from ten to forty times greater than a combined production level of luxA and luxB.

Embodiment 101

Any one of the preceding embodiments, wherein a combined production level of luxC, luxD, luxE, and flavin reductase ranges from twenty to thirty times greater than a combined production level of luxA and luxB.

Embodiment 102

Any one of the preceding embodiments, wherein at least one of luxC, luxD, luxE, and flavin reductase is present at a level greater than a level of at least one of luxA and luxB.

Embodiment 103

Any one of the preceding embodiments, wherein luxC, luxD, luxE, and flavin reductase are present at a combined level of from ten times to forty times greater than a combined level of luxA and luxB.

Embodiment 104

Any one of the preceding embodiments, wherein luxC, luxD, luxE, and flavin reductase are present at a combined level of from twenty times to thirty times greater than a combined level of luxA and luxB.

Embodiment 105

Any one of the preceding embodiments, wherein the stem cell or the at least one stem cell comprising luxA, luxB, luxC, luxD, luxE, and flavin reductase autonomously luminesces in the absence of an exogenous luminescent stimulator.

Embodiment 106

Any one of the preceding embodiments, wherein the constitutive promoter is a chicken beta-actin promoter.

Embodiment 107

Any one of the preceding embodiments, wherein the first constitutive promoter and the second constitutive promoter is a chicken beta-actin promoter.

Embodiment 108

Any one of the preceding embodiments, wherein at least one of the luxA nucleic acid, the luxB nucleic acid, the luxC nucleic acid, the luxD nucleic acid, the luxE nucleic acid, and the flavin reductase nucleic acid is operatively linked to at least one linker region.

Embodiment 109

Any one of the preceding embodiments, wherein the at least one linker region comprises a viral 2A peptide.

Embodiment 110

Any one of the preceding embodiments, wherein the agent comprises a chemotherapeutic agent, an antibiotic, an insecticide, a pesticide, an herbicide, or a fertilizer.

Embodiment 111

Any one of the preceding embodiments, wherein the stem cell or the at least one stem cell is an induced pluripotent stem cell, a mesenchymal stem cell, or a non-embryonic stem cell.

Embodiment 112

Any one of the preceding embodiments, wherein the exogenous luminescent stimulator is a fluorescent stimulation signal.

Embodiment 113

Any one of the preceding embodiments, wherein the exogenous luminescent stimulator is a chemical luminescent activator, and preferably wherein the chemical luminescent activator comprises an aldehyde functional group.

The foregoing description illustrates and describes the processes, manufactures, compositions of matter, and other teachings of the present disclosure. Additionally, the disclosure shows and describes only certain embodiments of the processes, manufactures, compositions of matter, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, manufactures, compositions of matter, and other teachings of the present disclosure and to enable others skilled in the art to utilize the teachings of the present disclosure in such, or other, embodiments and with the various modifications required by the particular applications or uses. Accordingly, the processes, manufactures, compositions of matter, and other teachings of the present disclosure are not intended to limit the exact embodiments and examples disclosed herein. Any section headings herein are provided only for consistency with the suggestions of 37 C.F.R. § 1.77, or otherwise to provide organizational queues. These headings shall not limit or characterize the invention(s) set forth herein.

What is claimed is:

1. A stem cell comprising an autobioluminescent phenotype including a luminescent signal in the absence of an exogenous luminescence stimulator, and wherein the stem cell further comprises:
   a first vector comprising a luxA nucleic acid and a luxB nucleic acid, and
   a second vector comprising a luxC nucleic acid, a luxD nucleic acid, a luxE nucleic acid, and a flavin reductase nucleic acid,
   and wherein at least one of the luxC, luxD, luxE, or flavin reductase nucleic acids is expressed in a molar ratio of at least ten times greater than at least one of the luxA or luxB nucleic acids.

2. The stem cell of claim 1, wherein the luxC, luxD, and luxE nucleic acids are expressed in a molar ratio of from ten to forty times greater than the luxA and luxB nucleic acids.

3. A stem cell comprising an autobioluminescent phenotype including a luminescent signal in the absence of an exogenous luminescence stimulator, the stem cell further comprising:
   a first vector comprising a luxA nucleic acid driven by a promoter having strong transcriptional activity;
   a second vector comprising a luxB nucleic acid driven by a promoter having strong transcriptional activity;
   a third vector comprising a luxC nucleic acid;
   a fourth vector comprising a luxD nucleic acid;
   a fifth vector comprising a luxE nucleic acid; and
   a sixth vector comprising a flavin-reductase nucleic acid.

4. The stem cell of claim 3, wherein at least one of luxC, luxD, luxE, or flavin reductase is expressed at a level greater than a level of at least one of luxA or luxB.

5. A cell comprising an autobioluminescent phenotype including a luminescent signal in the absence of an exogenous luminescence stimulator, wherein the cell expresses luxA, luxB, luxC, luxD, luxE, and flavin reductase, and wherein at least one of luxC, luxD, luxE, or flavin reductase is expressed in a molar ratio of at least ten times greater than at least one of luxA or luxB.

6. The cell of claim 5, wherein luxC, luxD, and luxE are expressed in a molar ratio of from ten to forty times greater than luxA and luxB.

7. The cell of claim 5, further comprising at least one vector having at least one of a luxA nucleic acid, a luxB nucleic acid, a luxC nucleic acid, a luxD nucleic acid, a luxE nucleic acid, or a flavin reductase nucleic acid.

8. The cell of claim 7, wherein the luminescent signal is inducible, and wherein at least one of the luxA nucleic acid, the luxB nucleic acid, the luxC nucleic acid, the luxD nucleic acid, the luxE nucleic acid, or the flavin reductase nucleic acid is operatively linked to an inducible promoter.

9. The cell of claim 7, wherein the luminescent signal is constitutively emitted, and wherein the luxA nucleic acid, the luxB nucleic acid, the luxC nucleic acid, the luxD nucleic acid, the luxE nucleic acid, and the flavin reductase nucleic acid are operatively linked to at least one constitutive promoter.

10. A cell comprising an autobioluminescent phenotype including a luminescent signal in the absence of an exogenous luminescence stimulator, wherein the cell comprises at least two vectors having at least one of a luxA nucleic acid, a luxB nucleic acid, a luxC nucleic acid, a luxD nucleic acid, a luxE nucleic acid, or a flavin reductase nucleic acid, and wherein the luxA nucleic acid and the luxB nucleic acid are on different of the at least two vectors and are driven by one or more promoters having strong transcriptional activity.

11. The cell of claim 10, wherein the at least two vectors comprise:
a first vector comprising a luxA nucleic acid;
a second vector comprising a luxB nucleic acid;
a third vector comprising a luxC nucleic acid;
a fourth vector comprising a luxD nucleic acid;
a fifth vector comprising a luxE nucleic acid; and
a sixth vector comprising a flavin reductase nucleic acid.

12. The cell of claim 10, wherein at least one of luxC, luxD, luxE, or flavin reductase are expressed at a level greater than a level of expression of at least one luxA or luxB.

13. The cell of claim 10, wherein the luminescent signal is inducible, and wherein at least one of the luxA nucleic acid, the luxB nucleic acid, the luxC nucleic acid, the luxD nucleic acid, the luxE nucleic acid, or the flavin reductase nucleic acid is operatively linked to an inducible promoter.

14. The cell of claim 10, wherein the luminescent signal is constitutively emitted, and wherein the luxA nucleic acid, the luxB nucleic acid, the luxC nucleic acid, the luxD nucleic acid, the luxE nucleic acid, and the flavin reductase nucleic acid are operatively linked to at least one constitutive promoter.

15. A method of real-time monitoring of cell viability of the cell of claim 9, comprising:
measuring the constitutive luminescent signal emitted from the cell; and
determining cell viability of the cell based on the measured constitutive luminescent signal, wherein the measured constitutive luminescent signal emitted from the cell correlates with the cell viability of the cell.

16. The method of claim 15, further comprising comparing the measured constitutive luminescent signal to a measured constitutive luminescent signal emitted from a control population having an autobioluminescent phenotype.

17. The method of claim 16, wherein a decrease in the measured constitutive luminescent signal emitted from the cell relative to the measured constitutive luminescent signal emitted from the control population is indicative of a negative change in cell viability of the cell, and wherein an increase in the measured constitutive luminescent signal emitted from the cell relative to the measured constitutive luminescent signal emitted from the control population is indicative of a positive change in cell viability of the cell.

18. A method of monitoring gene expression in the cell of claim 8, wherein the luminescent signal is responsive to an analyte, comprising:
contacting the cell with the analyte; and
measuring the luminescent signal emitted from the cell after contacting the cell with the analyte to monitor expression of at least one of the luxA nucleic acid, the luxB nucleic acid, the luxC nucleic acid, the luxD nucleic acid, the luxE nucleic acid, or the flavin reductase nucleic acid.

19. The method of claim 18, further comprising monitoring gene expression by comparing the measured luminescent signal emitted from the cell to a measured luminescent signal emitted from a control population having an autobioluminescent phenotype.

20. The method of claim 19, wherein a decrease in the measured constitutive luminescent signal emitted from the cell relative to the measured constitutive luminescent signal emitted from the control population is indicative of downregulation in expression of at least one the luxA nucleic acid, the luxB nucleic acid, the luxC nucleic acid, the luxD nucleic acid, the luxE nucleic acid, or the flavin reductase nucleic acid, and wherein an increase in the measured constitutive luminescent signal emitted from the cell relative to the measured constitutive luminescent signal emitted from the control population is indicative of upregulation in expression of at least one the luxA nucleic acid, the luxB nucleic acid, the luxC nucleic acid, the luxD nucleic acid, the luxE nucleic acid, or the flavin reductase nucleic acid.

21. The stem cell of claim 3, wherein the promoters have strong transcriptional activity in at least one of the stem cell or a cell differentiated from the stem cell.

22. The stem cell of claim 3, wherein the promotor driving the luxA nucleic acid and the promotor driving the luxB nucleic acid comprise a chicken beta-actin promotor.

23. The stem cell of claim 3, wherein luxC, luxD, luxE, and flavin reductase are expressed at a level of from three times to forty times greater than a level of expression of luxA and luxB.

24. The stem cell of claim 4, wherein at least one of luxC, luxD, luxE, or flavin reductase are expressed at a level of at least three times greater than a level of expression of at least one luxA or luxB.

25. The stem cell of claim 24, wherein the promotor driving the luxA nucleic acid and the promotor driving the luxB nucleic acid comprise a chicken beta-actin promotor.

26. The cell of claim 5, wherein the cell comprises a eukaryotic cell.

27. The cell of claim 10, wherein the cell comprises a eukaryotic cell.

28. The cell of claim 10, wherein the one or more promoters have strong transcriptional activity in at least one of the cell or a cell differentiated from the cell.

29. The cell of claim 27, wherein the promotor driving the luxA nucleic acid and the promotor driving the luxB nucleic acid comprise a chicken beta-actin promotor.

30. The cell of claim 10, wherein the one or more promotors having strong transcriptional activity comprise a chicken beta-actin promotor.

31. The cell of claim 10, wherein at least one of luxC, luxD, luxE, or flavin reductase are expressed at a level of at least three times greater than a level of expression of at least one luxA or luxB.

32. The cell of claim 10, wherein luxC, luxD, luxE, and flavin reductase are expressed at a level of from three times to forty times greater than a level of expression of luxA and luxB.

\* \* \* \* \*

SEQUENCE LISTING

```
<160> NUMBER OF SEQ ID NOS: 12

<210> SEQ ID NO 1
<211> LENGTH: 1083
<212> TYPE: DNA
<213> ORGANISM: Photorhabdus luminescens

<400> SEQUENCE: 1
atgaaatttg gaaactttt  gcttacatac caaccccccc aatttctca  aacagaggta      60 atgaaacggt tggttaaatt aggtcgcatc tctgaggaat gcggttttga taccgtatgg     120
ttacttgagc atcatttcac ggagtttggt ttgcttggta acccttatgt ggctgctgct     180
tatttacttg gcgcaaccaa gaaattgaat gtagggactg cggctattgt tctccccacc     240
gctcatccag ttcgccagct tgaagaggtg aatttgttgg atcaaatgtc aaaaggacga     300
tttcgatttg gtatttgtcg ggggctttac aataaagatt ttcgcgtatt tggcacagat     360
```

```
atgaataaca gtcgtgcctt aatggagtgt tggtataagt tgatacgaaa tggaatgact    420
gagggatata tggaagctga caacgaacat attaagttcc ataaggtaaa agtgctgccg    480
acggcatata gtcaaggtgg tgcacctatt tatgtcgttg ctgaatccgc ttccacgact    540
gaatgggccg ctcaacatgg tttaccgatg attttaagtt ggattataaa tactaacgaa    600
aagaaagcac aaattgagct ttataacgag gtcgctcaag aatatggaca cgatattcat    660
aatatcgacc attgcttatc atatataaca tcggtagacc atgactcaat gaaagcgaaa    720
gaaatttgcc ggaattttct ggggcattgg tatgattcct atgttaatgc cacaaccatt    780
tttgatgatt cagacaaaac aaagggctat gatttcaata aggacaatg gcgcgacttt     840 gtcttaaaag gacataaaaa tactaatcgt cgcgttgatt acagttacga atcaatccg     900 gtgggaaccc cgcaggaatg tattgatata attcaaacag acattgacgc cacaggaata    960
tcaaatattt gttgtgggtt tgaagctaat ggaacagtag atgaaattat ctcttccatg   1020
aagctcttcc agtctgatgt aatgccgttt cttaaagaaa acaacgttc gctattatat    1080 tag                                                                 1083

<210> SEQ ID NO 2
<211> LENGTH: 975
<212> TYPE: DNA
<213> ORGANISM: Photorhabdus luminescens

<400> SEQUENCE: 2
atgaaatttg gcttgttctt ccttaacttt atcaattcaa caactattca agagcaaagt     60
atagctcgca tgcaggaaat aacagaatat gtcgacaaat tgaattttga gcagattttg    120
gtgtgtgaaa tcatttttc agataatggt gttgtcggcg ctcctttgac tgtttctggt    180
tttttacttg gcctaacaga aaaattaaa attggttcat tgaatcatgt cattacaact    240
catcatcctg tccgcatagc ggaagaagcg tgcttattgg atcagttaag cgaaggaaga    300
tttattttag gatttagtga ttgcgagaga aaggatgaaa tgcatttttt caatcgccct    360
gaacaatacc agcagcaatt atttgaagaa tgctatgaca ttattaacga tgctttaaca    420
acaggctatt gtaatccaaa tggcgatttt tataatttcc ccaaaatatc cgtgaatccc    480
catgcttata cgcaaaacgg gcctcggaaa tatgtaacag caacaagttg tcatgttgtt    540
gagtgggctg ctaaaaaagg cattcctcta atctttaagt gggatgattc caatgaagtt    600
aaacatgaat atgcgaaaag atatcaagcc atagcaggtg aatatggtgt tgacctggca    660
gagatagatc atcagttaat gatattggtt aactatagtg aagacagtga gaaagctaaa    720
gaggaaacgc gtgcatttat aagtgattat attcttgcaa tgcaccctaa tgaaaatttc    780
gaaaagaaac ttgaagaaat aatcacgaaa aactccgtcg gagattatat ggaatgtaca    840
actgcggcta aattggcaat ggagaaatgt ggtgcaaaag gtatattatt gtcctttgaa    900
tcaatgagtg attttacaca tcaaataaac gcaattgata ttgtcaatga ataatattaaa   960 aagtatcaca tgtaa                                                    975

<210> SEQ ID NO 3
<211> LENGTH: 1443
<212> TYPE: DNA
<213> ORGANISM: Photorhabdus luminescens

<400> SEQUENCE: 3
atgaacaaaa aaatttcatt cattattaac ggtcgagttg aaatatttcc tgaaagtgat     60
```

```
gatttagtgc aatccattaa ttttggtgat aatagtgttc atttgccagt attgaatgat     120
tctcaagtaa aaacattat tgattataat gaaataatg aattgcaatt cataacatt       180 atcaactttc tctatacggt agggcaacga tggaaaaatg aagaatattc aagacgcagg    240
acatatattc gtgatctaaa agatatatg ggatattcag aagaaatggc taagctagag     300
gccaactgga tatctatgat tttgtgctct aaaggtggcc tttatgatct tgtaaaaaat    360
gaacttggtt ctcgccatat tatggatgaa tggctacctc aggatgaaag ttatattaga   420
gcttttccga aggaaaatc cgtacatctg ttgacgggta atgtgccatt atctggtgtg    480
ctgtctatat tgcgtgcaat tttaacaaag aatcaatgca ttataaaaac ctcatcaact   540 gatccttta ccgctaatgc attagcgcta agttttatcg atgtggaccc tcatcatccg    600
gtaacgcgtt ctttgtcagt cgtatattgg caacatcaag gcgatatatc actcgcaaaa   660
gagattatgc aacatgcgga tgtcgttgtt gcttggggag gggaagatgc gattaattgg   720
gctgtaaagc atgcaccacc cgatattgac gtgatgaagt ttggtcctaa aaagagttt    780 tgtattattg ataaccctgt tgatttagta tccgcagcta caggggcggc tcatgatgtt   840
tgtttttacg atcagcaagc ttgttttttcc acccaaaata tatattacat gggaagtcat   900
tatgaagagt ttaagctagc gttgataaga aaattgaact tatatgcgca tatattacca   960
aacaccaaaa aagatttga tgaaaaggcg gcctattcct tagttcaaaa agaatgttta   1020
tttgctggat taaaagtaga ggttgatgtt catcagcgct ggatggttat tgagtcaaat   1080
gcgggtgtag aactaaatca accacttggc agatgtgtgt atcttcatca cgtcgataat  1140
attgagcaaa tattgcctta tgtgcgaaaa aataaaacgc aaaccatatc tgttttcct   1200 tgggaggccg cgcttaagta tcgagactta ttagcattaa aggtgcaga aaggattgta    1260 gaagcaggaa tgaataatat atttcgggtt ggtggtgctc atgatggaat gagaccttta  1320
caacgattgg tgacatatat ttcccatgaa agaccatccc actatactgc taaagatgtt  1380
gcggtcgaaa tagaacagac tcgattcctg gaagaagata agttcctggt atttgtccca  1440
taa                                                                   1443
```

<210> SEQ ID NO 4
<211> LENGTH: 924
<212> TYPE: DNA
<213> ORGANISM: Photorhabdus luminescens

<400> SEQUENCE: 4

```
atggaaaata atccagata taaaaccatc gaccatgtta tttgtgttga agaaaataga      60
aaaattcatg tctgggagac gctgccaaaa gaaaatagtc caaagagaaa aaataccctt    120
attattgcgt cgggttttgc ccgcaggatg gatcattttg ccggtctggc agagtatttg    180
tcgcagaatg gatttcatgt gatccgctat gattctcttc accacgttgg attgagttca    240
gggacaattg atgaatttac aatgtccata ggaaaacaga gtttattagc agtggttgat    300 tggttaaaata cacgaaaaat aaataacctc ggtatgctgg cttcaagctt atctgcgcgg   360
atagcttatg caagtctatc tgaaattaat gtctcgtttt taattaccgc agtcggtgtg   420
gttaacttaa gatatactct cgaaagagct ttaggatttg attatctcag cttacctatt   480
gatgaattgc cagataattt agattttgaa ggtcataaat tgggtgctga ggttttttgcg  540 agagattgct tgattctggg ctgggaagat ttaacttcta caattaatag tatgatgcat    600
cttgatatac cgttttattgc ttttactgca aataatgacg attgggtaaa gcaagatgaa  660
gttattacat tactatcaag catccgtagt catcaatgta agatatattc tttactagga   720
```

```
agctcacatg atttgggtga gaacttagtg gtcctgcgca attttttatca atcggttacg    780 aaagccgcta tcgcgatgga taatggttgt ctggatattg atgtcgatat tattgagccg    840
tcattcgaac atttaaccat tgcggcagtc aatgaacgcc gaatgaaaat tgagattgaa    900
aatcaagtga tttcgctgtc ttaa                                            924

<210> SEQ ID NO 5
<211> LENGTH: 1113
<212> TYPE: DNA
<213> ORGANISM: Photorhabdus luminescens

<400> SEQUENCE: 5
atgacttcat atgttgataa acaagaaatc acagcaagtt cagaaattga tgatttgatt     60
ttttcgagtg atccattagt ctggtcttac gacgaacagg aaaagattag aaaaaaactt    120
gtgcttgatg cgtttcgtca tcactataaa cattgtcaag aataccgtca ctactgtcag    180
gcacataaag tagatgacaa tattacggaa attgatgata tacctgtatt cccaacatca    240
gtgtttaagt ttactcgctt attaacttct aatgagaacg aaattgaaag ttggtttacc    300
agtagtggca caaatggctt aaaaagtcag gtaccacgtg acagactaag tattgagagg    360
ctcttaggct ctgtaagtta tggtatgaaa tatattggta gttggttcga tcatcaaatg    420
gaattggtca acctgggacc agatagattt aatgctcata atatttggtt taaatatgtt    480
atgagcttgg tagagttatt atatcctacg tcattcaccg taacagaaga acacatagat    540
ttcgttcaga cattaaatag tcttgagcga ataaaacatc aagggaaaga tatttgtctt    600
attggttcgc catactttat ttatttgctc tgccgttata tgaaagataa aaatatctca    660
ttttctggag ataaaagtct ttatattata acggggggag gctggaaaag ttacgaaaaa    720
gaatctttga agcgtaatga tttcaatcat ctttttattcg acactttcaa cctcagtaat    780
attaaccaga tccgtgatat atttaatcaa gttgaactca cacttgtttt ctttgaggat    840
gaaatgcaac gtaaacatgt tccgccgtgg gtatatgcgc gagcacttga tcctgaaaca    900
ttgaaaccgg tacctgatgg gatgcctggt ttgatgagtt atatggatgc atcatcaacg    960
agttatccgg catttattgt taccgatgat atcggaataa ttagcagaga atatggtcaa   1020
tatcctggtg tattggttga aattttacgt cgcgttaata cgaggaaaca aaaaggttgt   1080
gctttaagct taactgaagc atttggtagt tga                                1113

<210> SEQ ID NO 6
<211> LENGTH: 723
<212> TYPE: DNA
<213> ORGANISM: Vibrio harveyi

<400> SEQUENCE: 6
atgaacaata cgattgaaac cattcttgct catcgctcta tccgaaaatt caccgcagtt     60
cctattactg atgaacaaag acaaaccatc attcaagcag gtttagctgc gtcttcttct    120
agtatgcttc aagtcgtctc aatcgttcga gtgactgact ctgaaaagcg taacgaattg    180
gctcaatttg ctggtaacca agcttatgtt gaaagtgcgg ctgagttctt agtgttttgt    240
attgattatc agcgccatgc aaccatcaat cctgatgtac aggcagactt tacagaacta    300
actctgattg gagcagtaga ttctggaatc atggcacaaa actgcttgct tgcagccgag    360
tctatgggat taggtggcgt atatattgga ggactaagga atagcgcagc tcaagttgat    420
gagctattgg gcttaccgga aaatagcgcg gtgttgtttg gtatgtgctt agggcatccc    480
```

```
gatcaaaatc cgaagtaaa gccacgccta cctgcacatg tggttgttca tgaaaatcaa    540
taccaagagc taaatttaga tgatattcag agctacgatc aaactatgca agcgtattat    600
gcgagccgta caagcaatca aaaactgagt acatggtcgc aagaagtcac tgggaagctt    660
gctggtgagt cgcgacctca tattctgccg tacttgaaca gtaaggggct agcaaaacgc    720
taa                                                                  723

<210> SEQ ID NO 7
<211> LENGTH: 1083
<212> TYPE: DNA
<213> ORGANISM: Photorhabdus luminescens

<400> SEQUENCE: 7
atgaagttcg gcaacttcct gctgacctac cagcccccc  agttcagcca gaccgaagtg     60
atgaagagac tggtcaaact gggccggatc agcgaggaat gcggcttcga caccgtgtgg    120
ctgctggaac accacttcac cgagttcggc ctgctgggaa accctacgt ggccgctgcc    180 tacctgctgg gcgccaccaa gaaactgaac gtgggcaccg ccgccatcgt gctgcctaca    240
gctcaccctg tgcggcagct ggaagatgtg aacctgctcg accagatgtc taagggccgg    300
ttcagattcg gcatctgcag aggcctgtac aacaaggact tccgggtgtt cggcaccgac    360
atgaacaact ccagagccct ggccgaatgt tggtacggcc tgatcaagaa cggcatgacc    420
gagggctaca tggaagccga caacgagcac atcaagttcc acaaagtgaa agtgaaccct    480
gccgcctaca gcagaggcgg agccctgtg tacgtggtgg ccgagagcgc cagcaccaca    540
gagtgggccc tcagtttgg cctgcccatg atcctgagct ggatcatcaa caccaacgag    600
aagaaggccc agctggaact gtacaacgag gtggcccagg aatacggcca cgacatccac    660
aacatcgacc actgcctgag ctacatcacc agcgtggacc acgacagcat caaggccaaa    720
gagatctgcc ggaagttcct gggccattgg tacgactcct acgtgaacgc caccaccatc    780
ttcgacgaca cgaccagac ccggggctac gacttcaaca agggccagtg gcgggacttc    840
gtgctgaagg acacaagga caccaaccgg cggatcgact acagctacga gatcaaccct    900
gtgggcaccc cccaggaatg catcgacatc atccagaaag acatcgacgc caccggcatc    960
agcaacatct gctgcggctt tgaggccaac ggcaccgtgg acgagattat cgccagcatg   1020
aagctgttcc agagcgacgt gatgcccttc ctgaaagaga agcagcggag cctgctgtac   1080
cag                                                                 1083

<210> SEQ ID NO 8
<211> LENGTH: 972
<212> TYPE: DNA
<213> ORGANISM: Photorhabdus luminescens

<400> SEQUENCE: 8
atgaagttcg gcctgttctt cctgaacttc atcaacagta ccaccgtgca ggaacagagc     60
atcgtccgga tgcaggaaat caccgagtac gttgacaagc tgaacttcga gcagatcctg    120
gtgtacgaga accacttcag cggcaacggc gtggtcggag cccctctgac cgtgtctggc    180
ttcctgctgg gcctgaccga gaagatcaag atcggcagcc tgaaccacat catcaccacc    240 caccacccg tgcggatcgc cgaggaagcc tgcctgctgg atcagctgag cgagggccgg    300
ttcatcctgg gcttcagcga ctgcgagaag aaagacgaga tgcggctgtt caaccggccc    360
gtggaatacc agcagcagct gttcgaggaa tgctacgaga tcatcaacga cgccctgacc    420
accggctact gcaaccccga caacgacttc tacagcttcc ccaagatcag cgtgaacccc    480
```

```
cacgcctaca cccagggcgg acccagacgg tacatcaccg ccaccagcca ccacatcgtg    540
gaatgggccg ccaagaaggg catcccsctg atcttcaagt gggacgacag caacgacgtg    600
cgctacgagt acgccgagcg gtacaaggcc gtggccgata agtacggcat cgacctgagc    660
gccatcgacc accagctgat ggtgctggtg aactacaacg aggacagcca aaggctaag    720 caggaaaccc gggccttcat ccgggactac gtgctggaaa tgtaccccaa cgagaacctg    780
gaaaacaagc tggaagagat catcaccgag aacgccgtgg cgactacac cgagtgtatc    840 gccgctgcca agctggccat cgagaagtgc ggcgccaagc gggtgctgct gagcttcgag    900
cccatgaacg acctgatgca ccagaaaaac gtgatcaaca tcgtggacga caacatcaag    960
aaataccata tg                                                       972

<210> SEQ ID NO 9
<211> LENGTH: 1443
<212> TYPE: DNA
<213> ORGANISM: Photorhabdus luminescens

<400> SEQUENCE: 9
atgggcacca agaagatcag cttcatcatc aacggccagg tggaaatctt ccccgagagc     60
gacgacctgg tgcagagcat caacttcggc gacaacagcg tgtacctgcc catcctgaac    120
gacagccacg tgaagaacat catcgactgc aacggcaaca acgagctgcg gctgcacaac    180
atcgtgaact ttctgtacac cgtgggccag cggtggaaga cgaagagta cagccggcgg    240 agaacctaca tccgggacct gaaaaagtac atgggctaca gcgaggaaat ggccaagctg    300
gaagccaact ggatcagcat gatcctgtgc agcaagggcg gcctgtacga cgtggtggaa    360
aacgagctgg gcagccggca catcatggac gagtggctgc cccaggacga gagctacgtg    420
cgggccttcc ccaagggcaa gtccgtgcat ctgctggccg gcaatgtgcc cctgagcggc    480
atcatgagca tcctgcgggc catcctgacc aagaaccagt gcatcatcaa gaccagcagc    540
accgacccct tcaccgccaa tgccctggcc ctgagcttca tcgacgtgga ccccaaccac    600
cccatcaccc ggtccctgag cgtgatctac tggccccacc agggcgacac cagcctggcc    660
aaagaaatca tgcggcacgc cgacgtgatc gtggcctggg gaggccccga cgccatcaat    720
tgggccgtgg aacacgcccc cagctacgcc gatgtgatca gttcggcag caagaaaagc    780 ctgtgcatca tcgacaaccc cgtggacctg accagcgccg ccacaggcgc cgctcacgac    840
gtgtgcttct acgaccagcg ggcctgcttc agcgcccaga acatctacta catgggcaac    900
cactacgagg aattcaagct ggccctgatc gagaagctga acctgtacgc ccacatcctg    960
cccaacgcca agaaggactt cgacgagaag gccgcctact ctctggtgca gaaagagagc   1020
ctgttcgccg gcctgaaggt ggaagtggac atccaccaga gatggatgat catcgagagc   1080
aacgccggcg tggaattcaa ccagcccctg gcagatgtg tgtacctgca ccacgtggac   1140
aacatcgagc agattctgcc ctacgtgcag aagaacaaga cccagaccat cagcatcttc   1200
ccttgggaat cctccttcaa ataccgggac gccctggctc tgaagggcgc cgagagaatc   1260
gtggaagctg gcatgaacaa catcttcaga gtgggcggca gccacgacgg catgaggcct   1320
ctgcagcggc tggtcacata tatcagccac gagcggccca gcaactacac cgccaaggac   1380
gtggccgtgg aaatcgagca gacccggttc ctggaagagg acaagttcct ggtgttcgtg   1440
ccc                                                                1443

<210> SEQ ID NO 10
```

```
<211> LENGTH: 921
<212> TYPE: DNA
<213> ORGANISM: Photorhabdus luminescens

<400> SEQUENCE: 10
atggaaaatg agagcaagta caagaccatc gaccacgtga tctgcgtgga aggcaacaag      60
aaaatccacg tgtgggagac actgcccgag gaaaacagcc ccaagcggaa gaacgccatc     120
atcattgcca gcggcttcgc cagacggatg gaccactttg ccggcctggc cgagtacctg     180
agccggaacg gcttccacgt gatcagatac gacagcctgc accatgtggg cctgagcagc     240
ggcaccatcg acgagttcac catgagcatc ggcaagcagt tctgctggc cgtggtggac      300 tggctgacca cccggaagat caacaacttc ggcatgctgg cctctagcct gagcgccaga     360
atcgcctacg ccagcctgtc cgagatcaac gccagcttcc tgatcaccgc cgtgggcgtg     420
gtcaacctgc ggtacagcct ggaacgggcc ctgggcttcg actacctgag cctgcccatc     480
aatgagctgc ccgacaacct ggacttcgag ggccacaagc tgggcgccga ggtgttcgcc     540
cgggactgcc tggatttcgg ctgggaggac ctggccagca ccatcaacaa tatgatgtac     600
ctggacatcc cctttatcgc ctttaccgcc aacaacgaca actgggtcaa acaggacgaa     660
gtgatcaccc tgctgagcaa catccggtcc aaccggtgca gatctacag cctgctgggc      720 agctcccacg acctgagcga gaacctggtg gtgctgcgga acttctacca gagcgtgacc     780
aaggccgcca ttgctatgga caacgaccac ctggacattg acgtggacat caccgagccc     840
agcttcgagc acctgacaat cgccaccgtg aacgagcggc ggatgcggat cgagatcgag     900
aaccaggcca tcagcctgtc c                                               921

<210> SEQ ID NO 11
<211> LENGTH: 1110
<212> TYPE: DNA
<213> ORGANISM: Photorhabdus luminescens

<400> SEQUENCE: 11
atgaccagct acgtggacaa gcaggaaatt accgccagca gcgagatcga cgatctgatc      60
ttcagcagcg accccctggt ctggtcctac gacgagcagg aaaagatccg gaagaaactg     120
gtgctggacg ccttccggaa ccactacaag cactgcagag agtaccggca ctactgccag     180
gcccacaagg tggacgataa tatcaccgag atcgatgaca tccccgtgtt ccccaccagc     240
gtgttcaagt tcacccggct gctgaccagc caggaaaacg agatcgagtc ctggttcacc     300
agctccggca ccaacggcct gaagtcccag gtggcccggg accggctgag catcgagaga     360
ctgctgggct ccgtgtccta cggcatgaag tacgtgggca gttggttcga tcaccagatc     420
gagctggtca acctgggacc cgaccggttc aacgcccaca tatctggtt caaatacgtg      480 atgagcctgg tggaactgct gtaccccacc accttcaccg tgaccgagga acggatcgac     540
ttcgtgaaaa ccctgaactc cctggaacgg atcaagaacc agggcaagga cctgtgcctg     600
atcggctccc cctacttcat ctacctgctg tgccactaca tgaaggacaa agagatctcc     660
ttcagcggcg acaagtccct gtacatcatc acaggcggcg gatggaagtc ctacgagaaa     720
gagtccctga gcgggacga cttcaatcat ctgctgttcg acaccttcaa cctgagcgac     780
atctcccaga tccgggacat cttcaaccag gtggaactga atacctgctt cttcgaggac     840
gagatgcagc ggaagcacgt gcccccctgg gtgtacgcta gagccctgga ccccgagaca     900
ctgaagcccg tgcctgatgg caccccctgg ctgatgagct acatggacgc cagcgccacc     960
agctaccccg cctttatcgt gaccgacgac gtgggcatca tcagccgcga gtacggcaag    1020
```

```
tacccggcg tgctggtgga aatcctgcgg agagtgaaca cccggaccca gaagggctgc    1080
gccctgagcc tgacagaggc cttcgacagc                                    1110

<210> SEQ ID NO 12
<211> LENGTH: 723
<212> TYPE: DNA
<213> ORGANISM: Vibrio harveyi

<400> SEQUENCE: 12
atgaacaaca ccatcgagac aatcctggcc caccggtcca tccggaagtt taccgccgtg     60
cccatcaccg acgagcagag acagaccatc atccaggccg gactggctgc cagctccagc    120
tctatgctgc aggtggtgtc catcgtgcgc gtgaccgaca gcgagaagcg gaatgagctg    180
gcccagttcg ccggcaacca ggcctacgtg aatctgccg ccgagtttct ggtgttctgc     240
atcgactacc agcggcacgc cacaatcaac cccgacgtgc aggccgattt caccgagctg    300
acactgatcg gcgccgtgga ctccggcatc atggcccaga attgcctgct ggctgccgag    360
tctatgggcc tgggcggcgt gtacatcggc ggcctgagaa actctgccgc ccaggtggac    420
gagctgctgg ggctgcctga aacagcgcc gtgctgttcg gcatgtgcct gggccacccc     480
gaccagaacc ccgaagtgaa gcccagactg cccgcccacg tggtggtgca cgagaatcag    540
taccaggaac tgaacctgga cgacatccag agctacgacc agaccatgca ggcctactac    600
gccagcagaa ccagcaacca gaagctgagc acctggtccc aggaagtcac cggcaagctc    660
gctggcgaga gcagaccca cattctgccc tacctgaaca gcaagggcct ggccaagaga    720
taa                                                                  723
```